United States Patent
Shinohara et al.

(10) Patent No.: US 12,391,674 B2
(45) Date of Patent: Aug. 19, 2025

(54) HETEROCYCLIC COMPOUNDS FOR THE TREATMENT OF EPILEPSY

(71) Applicant: OTSUKA PHARMACEUTICAL CO., LTD., Tokyo (JP)

(72) Inventors: Tomoichi Shinohara, Osaka (JP); Shin Iwata, Osaka (JP); Masaki Suzuki, Osaka (JP); Kenta Arai, Osaka (JP); Nobuaki Ito, Osaka (JP); Takuya Chiba, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 1075 days.

(21) Appl. No.: 17/292,528

(22) PCT Filed: Nov. 29, 2019

(86) PCT No.: PCT/JP2019/046879
§ 371 (c)(1),
(2) Date: May 10, 2021

(87) PCT Pub. No.: WO2020/111263
PCT Pub. Date: Jun. 4, 2020

(65) Prior Publication Data
US 2021/0403456 A1   Dec. 30, 2021

(30) Foreign Application Priority Data

Nov. 30, 2018 (JP) .................. 2018-224724

(51) Int. Cl.
| | |
|---|---|
| *C07D 403/04* | (2006.01) |
| *A61P 25/08* | (2006.01) |
| *C07D 239/34* | (2006.01) |
| *C07D 239/47* | (2006.01) |
| *C07D 239/54* | (2006.01) |
| *C07D 401/04* | (2006.01) |
| *C07D 401/12* | (2006.01) |
| *C07D 405/04* | (2006.01) |
| *C07D 413/04* | (2006.01) |
| *C07D 417/04* | (2006.01) |
| *C07D 471/04* | (2006.01) |
| *C07D 487/04* | (2006.01) |

(52) U.S. Cl.
CPC ............ *C07D 403/04* (2013.01); *A61P 25/08* (2018.01); *C07D 239/34* (2013.01); *C07D 239/47* (2013.01); *C07D 239/54* (2013.01); *C07D 401/04* (2013.01); *C07D 401/12* (2013.01); *C07D 405/04* (2013.01); *C07D 413/04* (2013.01); *C07D 417/04* (2013.01); *C07D 471/04* (2013.01); *C07D 487/04* (2013.01)

(58) Field of Classification Search
CPC .. C07D 403/04; C07D 239/34; C07D 239/47; C07D 239/54; C07D 401/04; C07D 401/12; C07D 405/04; C07D 413/04; C07D 417/04; C07D 471/04; C07D 487/04; A61P 25/08

See application file for complete search history.

(56) References Cited

U.S. PATENT DOCUMENTS

| | | | |
|---|---|---|---|
| 4,239,888 A | 12/1980 | Miller | |
| 6,872,729 B2 * | 3/2005 | Shibata | A01N 43/54 544/320 |
| 10,647,675 B2 | 5/2020 | Watanabe et al. | |
| 10,800,758 B2 | 10/2020 | Shinohara et al. | |
| 2012/0202806 A1 * | 8/2012 | Durrenberger | A61P 35/00 514/235.8 |
| 2019/0055199 A1 | 2/2019 | Watanabe et al. | |
| 2020/0017476 A1 | 1/2020 | Shinohara et al. | |
| 2020/0399245 A1 | 12/2020 | Shinohara et al. | |

FOREIGN PATENT DOCUMENTS

| | | |
|---|---|---|
| GB | 1 456 964 A | 12/1976 |
| JP | 2002-193710 A | 7/2002 |
| JP | 2013-513564 A | 4/2013 |
| JP | 2013-518046 A | 5/2013 |
| JP | 2014-521651 A | 8/2014 |
| JP | 2018-145180 A | 9/2018 |

(Continued)

OTHER PUBLICATIONS

Mickevicius et al. (Chemistry of Heterocyclic Compounds. 2004: 40(6); 781-787). (Year: 2004).*
International Search Report dated Mar. 5, 2020 issued in No. PCT/JP2019/046879.
International Preliminary Report on Patentability and Translation of Written Opinion of the International Searching Authority for PCT/JP2019/046879 dated May 25, 2021.

(Continued)

*Primary Examiner* — Daniel R Carcanague
*Assistant Examiner* — Jerica Katlynn Wilson
(74) *Attorney, Agent, or Firm* — Sughrue Mion, PLLC

(57) ABSTRACT

The present invention provides a novel heterocyclic compound represented by Formula [I] and a salt thereof:

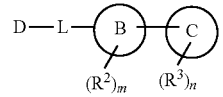

[Formula I]

wherein the symbols are as defined in the specification, which is useful for treating, preventing and/or diagnosing seizure and the like in disease involving epileptic seizure or convulsive seizure (including multiple drug resistant seizure, refractory seizure, acute symptomatic seizure, febrile seizure and status epilepticus), as well as a medical use therefor.

17 Claims, No Drawings

(56) References Cited

FOREIGN PATENT DOCUMENTS

| | | |
|---|---|---|
| JP | 6870064 B2 | 4/2021 |
| JP | 2021-187859 A | 12/2021 |
| WO | 2004/009559 A2 | 1/2004 |
| WO | 2004/029204 A2 | 4/2004 |
| WO | 2011/069951 A1 | 6/2011 |
| WO | 2011/091153 A1 | 7/2011 |
| WO | 2012/076877 A1 | 6/2012 |
| WO | 2012/168710 A1 | 12/2012 |
| WO | 2013/016488 A1 | 1/2013 |
| WO | 2013/083994 A1 | 6/2013 |
| WO | 2013/175215 A1 | 11/2013 |
| WO | 2017/047602 A1 | 3/2017 |
| WO | 2017/098254 A1 | 6/2017 |
| WO | 2018/169360 A1 | 9/2018 |
| WO | 2018/221667 A1 | 12/2018 |

OTHER PUBLICATIONS

Nilsen et al., "Discovery, Synthesis, and Optimization of Antimalarial 4(1H)-Quinolone-3-Diarylethers", Journal of Medicinal Chemistry, 2014, vol. 57, No. 9, pp. 3818-3834 (17 pages total).

Mickevicius et al., "Synthesis and Cyclization of N-(4-Phenoxyphenyl)-β-Alanines", Chemistry of Heterocyclic Compounds, 2004, vol. 40, No. 6, pp. 781-787 (7 pages total).

International Preliminary Report on Patentability and Translation of Written Opinion of the International Searching Authority for PCT/JP2017/020322 dated Dec. 3, 2019, a priority application of U.S. Appl. No. 16/471,998 (now U.S. Pat. No. 10,800,758).

International Preliminary Report on Patentability and Written Opinion of the International Searching Authority for PCT/JP2018/020997 dated Dec. 3, 2019, corresponding to U.S. Appl. No. 16/471,998 (now U.S. Pat. No. 10,800,758).

International Search Report dated Aug. 10, 2018 issued in No. PCT/JP2018/020997, corresponding to U.S. Appl. No. 16/471,998 (now U.S. Pat. No. 10,800,758).

International Search Report dated Aug. 22, 2017 issued in No. PCT/JP2017/020322, a priority application of U.S. Appl. No. 16/471,998 (now U.S. Pat. No. 10,800,758).

Japanese Office Action issued in Application No. 2019-535398 dated Apr. 21, 2020, corresponding to U.S. Appl. No. 16/471,998 (now U.S. Pat. No. 10,800,758).

Office Action issued Feb. 28, 2022 in U.S. Appl. No. 17/010,182.

Notice of Allowance issued Oct. 3, 2022 in U.S. Appl. No. 17/010,182.

Simon F. Campbell, et al.,"2,4-Diamino-6,7-dimethoxyquinazolines. 3. 2-(4-Heterocyclylpiperazin-1-yl) Derivatives as $\alpha_1$-Adrenoceptor Antagonists and Antihypertensive Agents", Journal of Medicinal Chemistry, 1987, vol. 30, No. 10, pp. 1794-1798 (5 pages).

Masazumi Ikeda, et al., "Synthesis and Cytoprotective Antiulcer Activity of 2- or 4-(1H-Pyrazol-1-yl) pyrimidine Derivatives Related to Mepirizole and Dulcerozine", Chem. Pharm. Bull., vol. 44, No. 9, 1996, pp. 1700-1706 (7 pages).

Communication dated Aug. 30, 2023 issued by the Eurasian Patent Organization in corresponding Eurasian application No. 202191473.

Peereboom, R., et al., "Ring transformations in reactions of heterocyclic halogeno compounds with nucleophiles (XXXVIII). The influence of leaving group mobility on reactions of 4-X-6-methyl (or phenyl-pyrimidine 1-oxides with liquid ammonia and with potassium amide in liquid ammonia", Recueil, Journal of the Royal Netherlands Chemical Society, Nov. 1974, vol. 93, No. 11, pp. 284-287 (4 pages total).

Database Registry Chemical Abstract Service, US; Retrieved from STN Database accession No. RN 1894376-77-2 Registry Entered STN: Apr. 21, 2016, Compound Name: 5-Phenoxy-2(4-piperidinyl)pyrimidine Supplier: Aurora Fine Chemicals (1 page).

Database Registry Chemical Abstract Service, US, STN Database accession No. RN 1891296-62-0, Apr. 17, 2016, Compound Name: 5-Phenoxy-2-(3-piperidinyl)pyrimidine Supplier: Aurora Fine Chemicals (1 page).

Database Registry Chemical Abstract Service, US; Retrieved from STN Database accession No. RN 1045503-40-9 Registry Entered STN: Sep. 1, 2008 Compound Name: 4-Phenoxy-6-(1-piperidinyl)pyrimidine Supplier: Albany Molecular Research, Inc. (AMRI) (1 page).

Database Registry Chemical Abstract Service, US; Retrieved from STN Database accession No. RN 1894399-87-1 Registry Entered STN: Apr. 21, 2016 Compound Name: 1-(5-Phenoxy-2-pyrimidinyl)-4-piperidinamine Supplier: Aurora Fine Chemicals ( 1 page).

Bardhan, et al., "Heteroaryl Ethers by Oxidative Palladium Catalysis of Pyridotriazol-1-yloxy Pyrimidines with Arylboronic Acids", Organic Letters, 2009, vol. 11, No. 12, pp. 2511-2514 (4 pages).

Huang, H. et al., ACS Medicinal Chemistry Letters. 2012, vol. 3, pp. 1059-1064.

Database Registry Chemical Abstract Service, US; Retrieved from STN Database accession No. RN944776-58-3; STN Entry Date Aug. 16, 2007; Compound Name: 4,5-Dichloro-2-[6-(2,5-dimethylphenoxy)-4-pyrimidinyl]-3(2H)-pyridazinone [5] (1 page).

Database Registry Chemical Abstract Service, US; Retrieved from STN Database accession No. 923551-04-6; STN Entry Date Feb. 27, 2007; Compound Name: 4,5-Dichloro-2-[6-(3,5-dimethylphenoxy)-4-pyrimidinyl]-3(2H)-pyridazinone [5] (1 page).

Database Registry Chemical Abstract Service, US; Retrieved from STN Database accession No. 927639-49-4; STN Entry Date Mar. 20, 2007; Compound Name: 4,5-Dichloro-2-[6-[3-(trifluoromethoxy)phenoxy]-4-pyrimidinyl]-3(2H)-pyridazinone [5] (1 page).

Database Registry Chemical Abstract Service, US; Retrieved from STN Database accession No. 444151-95-5; STN Entry Date Aug. 19, 2002; Compound Name: 5-(2-Methoxyphenoxy)-2,2'-bipyrimidine [5] (1 page).

Database Registry Chemical Abstract Service, US; Retrieved from STN Database accession No. 667895-27-4; STN Entry Date Mar. 26, 2004; Compound Name: Chloro-5-methoxy-2-[6-(4-methylphenoxy)-4-pyrimidinyl]-3(2H)-pyridazinone [5] (1 page).

Database Registry Chemical Abstract Service, US; Retrieved from STN Database accession No. 667895-26-3; STN Entry Date Mar. 26, 2004; Compound Name: 4-Chloro-5-ethoxy-2-[6-(4-methylphenoxy)-4-pyrimidinyl]-3(2H)-pyridazinone [5] (1 page).

Database Registry Chemical Abstract Service, US; Retrieved from STN Database accession No. 724430-57-3; STN Entry Date Aug. 9, 2004; Compound Name: 4-4,5-Dichloro-2-[6-(2-methylphenoxy)-4-pyrimidinyl]-3(2H)-pyridazinone [5] (1 page).

Database Registry Chemical Abstract Service, US; Retrieved from STN Database accession No. 724429-17-8; STN Entry Date Aug. 9, 2004; Compound Name: 4,5-Dichloro-2-[2-(3,4-dimethylphenoxy)-6-methoxy-4-pyrimidinyl]-3(2H)-pyridazinone [5] (1 page).

Database Registry Chemical Abstract Service, US; Retrieved from STN Database accession No. 724430-65-3; STN Entry Date Aug. 9, 2004; Compound Name: 1,5,6,7-Tetrahydro-1-[6-(2-methylphenoxy)-4-pyrimidinyl]-4H-indazol-4-one [5] ] (1 page).

Australian Examination Report dated Jan. 16, 2025 issued by the Australian Government in corresponding Australian application No. 2019390907.

Non-Final Office Action issued Feb. 10, 2025 in U.S. Appl. No. 18/091,790.

\* cited by examiner

HETEROCYCLIC COMPOUNDS FOR THE TREATMENT OF EPILEPSY

CROSS REFERENCE TO RELATED APPLICATIONS

This application is a National Stage of International Application No. PCT/JP2019/046879 filed Nov. 29, 2019, claiming priority to Japanese Patent Application No. 2018-224724 filed Nov. 30, 2018.

TECHNICAL FIELD

The present invention relates to a heterocyclic compound and a salt thereof. The present invention also relates to a medicament having a heterocyclic compound or a salt thereof as an active ingredient and useful for treating, preventing and/or diagnosing seizure and the like in disease involving epileptic seizure or convulsive seizure.

BACKGROUND ART

The prevalence of epilepsy is about 1% of the population. It is considered a common neurological disorder with about 1 million patients in Japan and a lifetime morbidity rate of 3% to 4%, and it is estimated that tens of thousands of people develop epilepsy every year. About 70% of these patients can control their seizure with existing antiepileptic drugs and pursue their everyday lives without problems, but the remaining 30% of epileptic patients are unable to adequately control their seizure, and are anxious that seizure may occur without warning. Most existing antiepileptic drugs are aimed to normalize the excitation/inhibition imbalances in neural activity by suppressing hyper-excitation and excessive synchronization of neuronal activity, but doses above the optimal dose may disturb the equilibrium of neuronal activity, and induce motor dysfunction and epileptic seizure.

PTL 1 discloses compounds having a pyrimidine in its structure as compounds for use in the treatment and the like of diseases or conditions requiring modulators of the Kv3.1 and/or Kv3.2 channel, including epilepsy.

PTL 2 and 3 disclose compounds having a pyrimidine skeleton as kynurenine-3-monooxygenase inhibitors for treating neurodegerenative conditions including epilepsy.

PTL 4 discloses a compound having a structure containing phenoxypyrimidine or pyridyloxypyrimidine as antagonist and/or inverse agonist of cannabinoid-1 receptor, useful for the treatment of diseases including epilepsy.

CITATION LIST

Patent Literature

[PLT1] WO 2011/069951
[PLT2] WO 2013/016488
[PLT3] WO 2011/091153
[PLT4] WO 2004/029204

DISCLOSURE OF INVENTION

Solution to Problem

It is an object of the present invention to provide a novel pyrimidine compound or a salt thereof useful for treating, preventing and/or diagnosing seizure and the like in disease involving epileptic seizure or convulsive seizure, together with a medical use therefor.

It is another object of the present invention to provide a medicament having a wide treatment spectrum in comparison with existing antiepileptic drugs, whereby the balance of neuronal excitation/inhibition can be maintained even at doses that completely suppress epileptic seizure.

As a result of exhaustive research aimed at solving the aforementioned problems, the inventors succeeded in synthesizing a novel pyrimidine compound having a wide treatment spectrum in comparison with existing antiepileptic drugs. The present invention was perfected based on these findings.

This is, the present invention includes the following embodiments.

[1] A compound represented by Formula I:

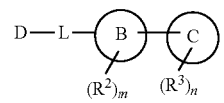

[Formula I]

wherein
D is

or $C_{1-6}$ alkyl optionally substituted with halogen;
ring A is benzene, pyridine, indole or indazole;
ring B is pyrimidine, pyridazine, pyridine, pyrazole, benzene or naphthalene, wherein,
(i) when ring B is pyrimidine, ring C is selected from the group consisting of the following unsaturated rings and their oxides and dioxides (provided that pyrimidine-2,4-dione and dihydropyrimidine-2,4-dione are excluded), and those in which a part or all of unsaturated bonds in these rings are reduced with hydrogen:
  (a) an unsaturated 3- to 8-membered monocyclic heterocycle containing 1 to 4 nitrogen atoms alone as ring-constituting heteroatom,
  (b) an unsaturated 7- to 15-membered bicyclic or tricyclic heterocycle containing 1 to 5 nitrogen atoms alone as ring-constituting heteroatom,
  (c) an unsaturated 7- to 12-membered bicyclic heterocycle containing 1 to 3 oxygen atoms alone as ring-constituting heteroatom,
  (d) an unsaturated 3- to 8-membered monocyclic heterocycle containing 1 to 2 oxygen atoms and 1 to 3 nitrogen atoms as ring-constituting heteroatom,
  (e) an unsaturated 7- to 12-membered bicyclic heterocycle containing 1 or 2 sulfur atoms and 1 to 3 nitrogen atoms as ring-constituting heteroatom, and . . .
  (f) an unsaturated 3- to 8-membered monocyclic hydrocarbon ring;
(ii) when ring B is pyridazine, pyridine, pyrazole, benzene or naphthalene, ring C is pyrimidine-2,4-dione or dihydropyrimidine-2,4-dione;

$R^1$ is halogen, $C_{1-6}$ alkyl optionally substituted with halogen, —O—$C_{1-6}$ alkyl optionally substituted with halogen, —CN or —SF$_5$;

$R^2$ is halogen, $C_{1-6}$ alkyl, or —O—$C_{1-6}$ alkyl;

$R^3$ is halogen, $C_{1-6}$ alkyl optionally substituted with halogen or —O—$C_{1-6}$ alkyl, —O—$C_{1-6}$ alkyl optionally substituted with halogen, —$C_{1-6}$ alkyl-OH, —OH, —CN, —CONH$_2$ or —NH$_2$;

L is bond, $C_{1-6}$ alkylene, —O— or —S—;

k is 0, 1 or 2, and when k is 2, each $R^1$ independently represents the same or different substituent;

m is 0, 1 or 2, and when m is 2, each $R^2$ independently represents the same or different substituent; and n is 0, 1 or 2, and when n is 2, each $R^3$ independently represents the same or different substituent;

or a salt thereof.

[2] The compound according to [1], wherein, in Formula I, D is

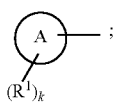

ring A is benzene or pyridine;

ring B is pyrimidine;

ring C is selected from the group consisting of the following unsaturated rings and their oxides and dioxides (provided that pyrimidine-2,4-dione and dihydropyrimidine-2,4-dione are excluded), and those in which a part or all of unsaturated bonds in these rings are reduced with hydrogen:

pyridine,
pyridazine,
pyrimidine,
indole,
pyrrolopyridine,
indazole,
benzimidazole,
pyrazolopyridine,
imidazopyridine,
imidazopyrazine,
imidazopyridazine,
triazolopyridine,
pyrazolopyrimidine,
imidazopyrimidine,
triazolopyrimidine,
quinoline,
isoquinoline,
naphthyridine,
quinazoline,
quinoxaline,
benzodioxole,
oxazine,
oxazepine,
benzothiazole, and
benzene;

$R^1$ is halogen, $C_{1-6}$ alkyl optionally substituted with halogen, —O—$C_{1-6}$ alkyl optionally substituted with halogen or —CN;

$R^2$ is —O—$C_{1-6}$ alkyl;

$R^3$ is halogen, $C_{1-6}$ alkyl optionally substituted with halogen or —O—$C_{1-6}$ alkyl, —O—$C_{1-6}$ alkyl optionally substituted with halogen, —$C_{1-6}$ alkyl-OH, —OH, —CN, —CONH$_2$ or —NH$_2$;

L is —O—; and k is 0, 1 or 2, and when k is 2, each $R^1$ independently represents the same or different substituent;

m is 0 or 1;

n is 0, 1 or 2, and when n is 2, each $R^3$ independently represents the same or different substituent;

or a salt thereof.

[3] The compound according to [2], wherein, in Formula I, ring C is selected from the group consisting of the following unsaturated rings and their oxides, and those in which a part or all of unsaturated bonds in these rings are reduced with hydrogen:

pyridine,
pyridazine,
pyrrolopyridine,
indazole,
pyrazolopyridine,
imidazopyridine,
imidazopyrazine,
imidazopyridazine,
pyrazolopyrimidine,
triazolopyrimidine,
quinoline,
isoquinoline,
naphthyridine,
quinoxaline, and
benzene;

$R^1$ is halogen or $C_{1-6}$ alkyl optionally substituted with halogen;

$R^3$ is $C_{1-6}$ alkyl optionally substituted with halogen, —O—$C_{1-6}$ alkyl optionally substituted with halogen, —OH, —CONH$_2$ or —NH$_2$;

L is —O—;

k and n are 0 or 1; and m is 0;

or a salt thereof.

[4] The compound according to [3], wherein, in Formula I, ring C is selected from the group consisting of the following unsaturated rings and their oxides, and those in which a part or all of unsaturated bonds in these rings are reduced with hydrogen:

pyridine,
pyridazine,
pyrazolopyridine, and
Imidazopyridine;

$R^3$ is —OH or —NH$_2$;

L is —O—;

k and m are 0; and n is 0 or 1;

or a salt thereof.

[5] The compound according to [1], wherein, in Formula I, D is:

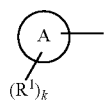

or $C_{1-6}$ alkyl optionally substituted with halogen;

ring A is benzene or pyridine;

ring B is pyridazine, pyridine, pyrazole, benzene, or naphthalene;

ring C is pyrimidine-2,4-dione or dihydropyrimidine-2,4-dione;

$R^1$ is halogen, $C_{1-6}$ alkyl optionally substituted with a halogen, —O—$C_{1-6}$ alkyl optionally substituted with halogen, —CN or —SF$_5$;

$R^2$ is halogen, $C_{1-6}$ alkyl, or —O—$C_{1-6}$ alkyl;

$R^3$ is $C_1$-6 alkyl; L is bond, $C_{1-6}$ alkylene, —O— or —S—;

k is 0, 1 or 2, and when k is 2, each $R^1$ independently represents the same or different substituent;

m is 0, 1 or 2, and when m is 2, each $R^2$ independently represents the same or different substituent; and n is 0, 1 or 2, and when n is 2, each $R^3$ independently represents the same or different substituent;

or a salt thereof.

[6] The compound or salts thereof according to [5], wherein, in Formula I, ring A is benzene;

ring B is benzene, pyridine, or pyridazine;

ring C is dihydropyrimidine-2,4-dione;

$R^1$ is halogen;

L is —O—;

k is 0 or 1; and m and n are 0;

or a salt thereof.

[7] A compound selected from the group consisting of the following compounds:

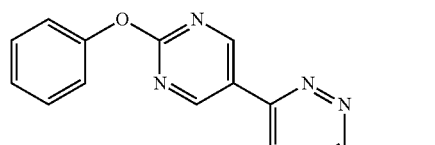

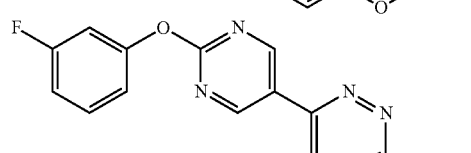

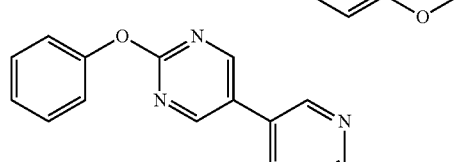

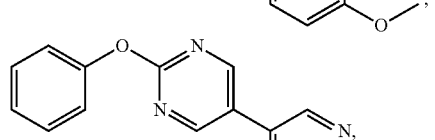

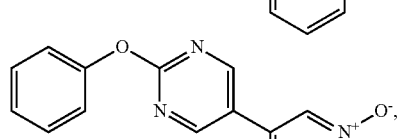

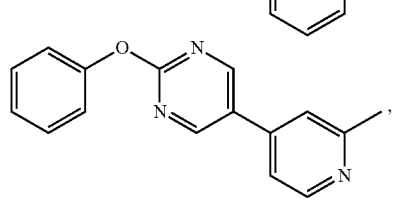

-continued

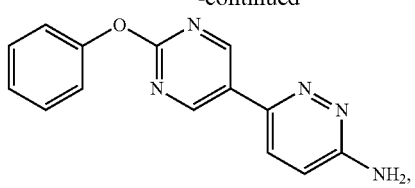

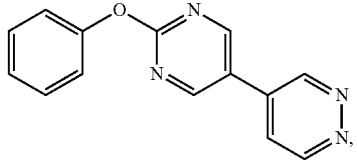

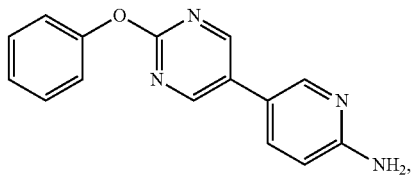

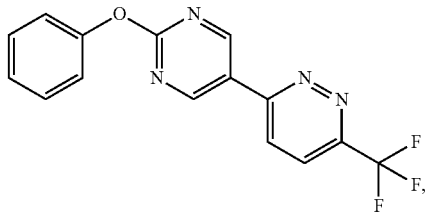

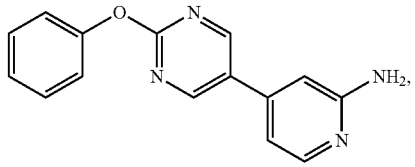

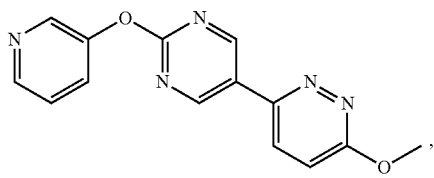

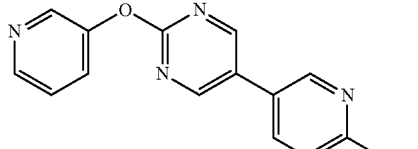

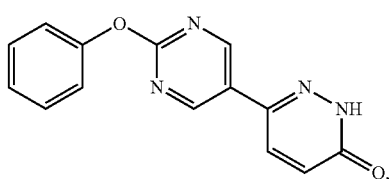

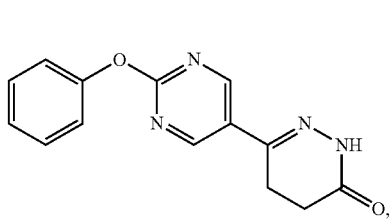

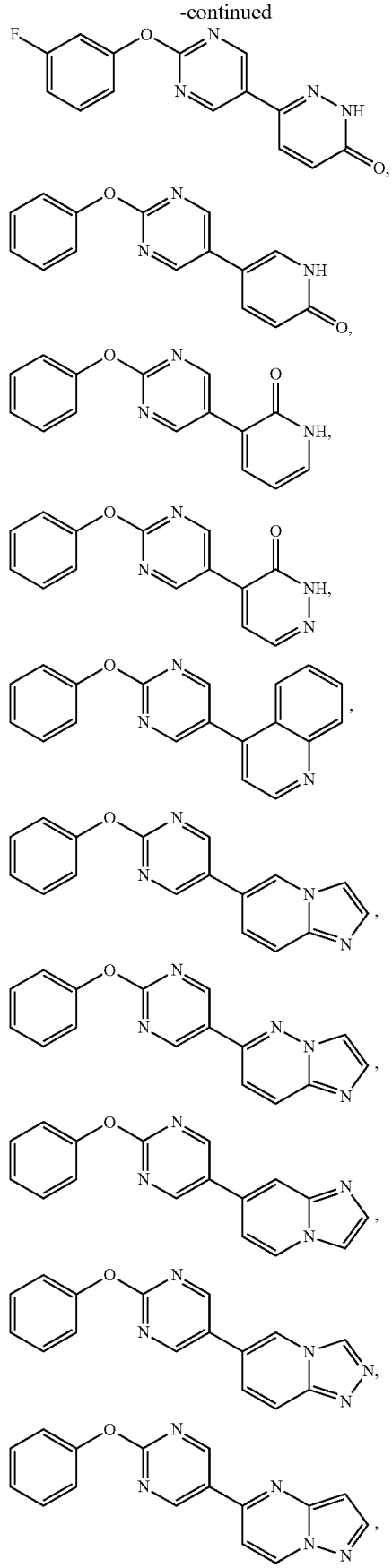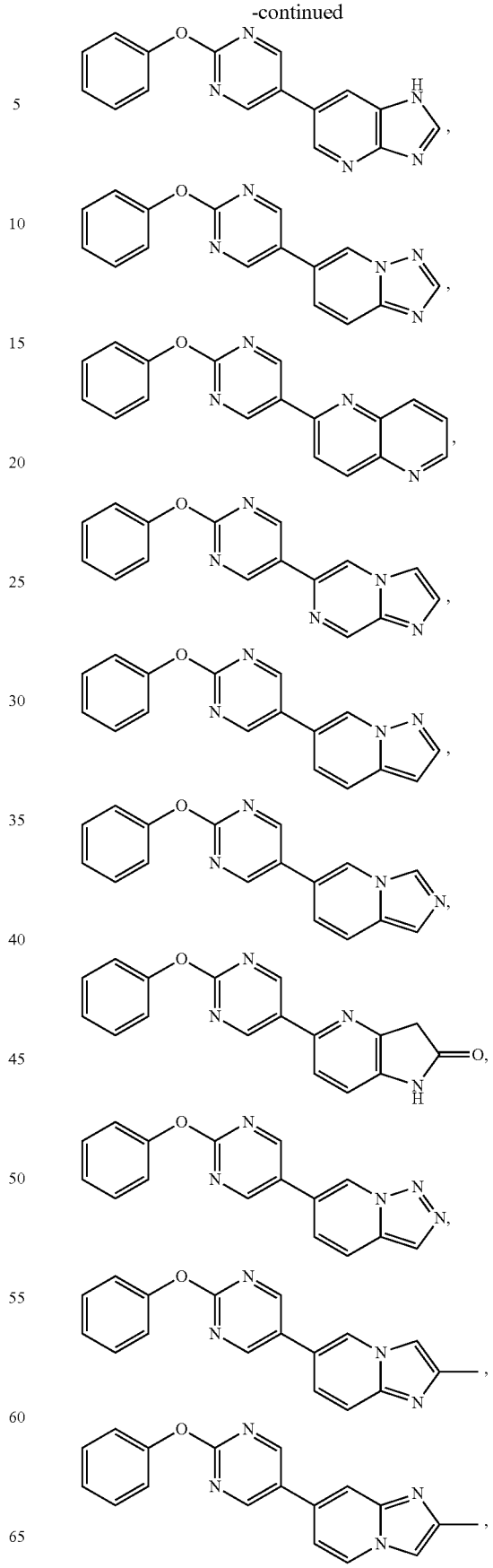

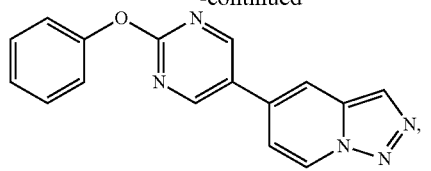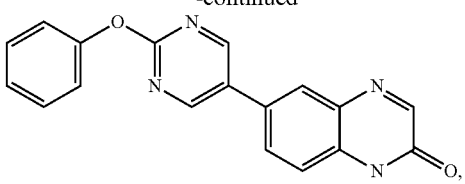
or a salt thereof.

[8] The compound according to [7] selected from the group consisting of the following compounds:

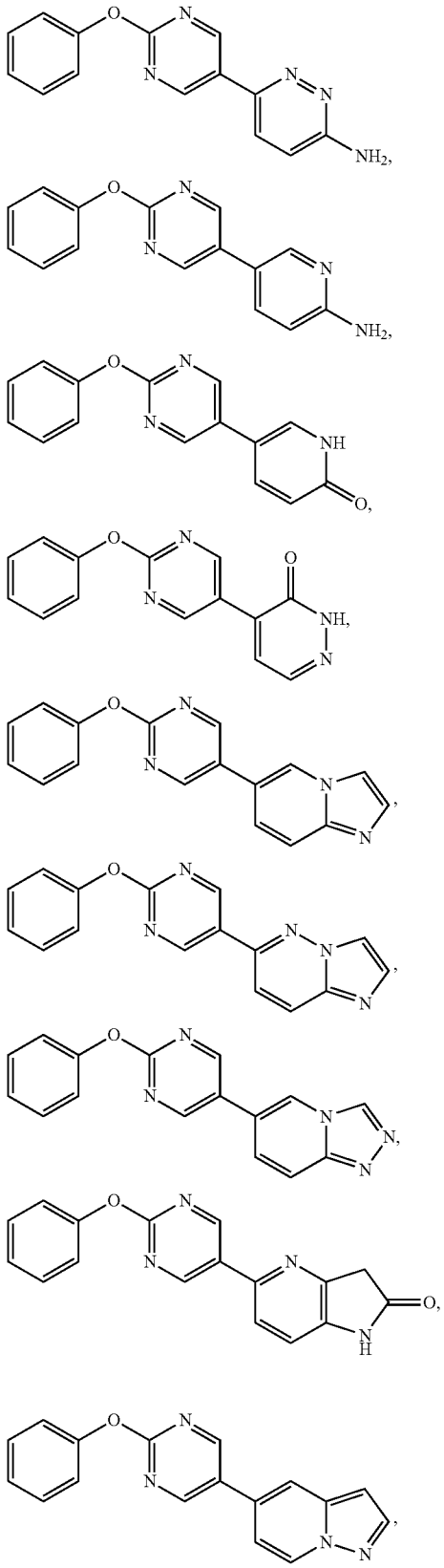

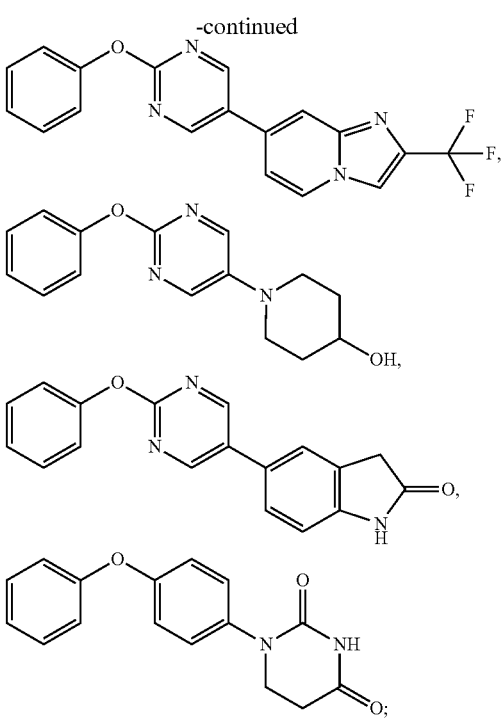

or a salt thereof.

[9] A pharmaceutical composition comprising a compound or a salt thereof according to any of [1] to [8] as an active ingredient and pharmaceutically acceptable carrier or excipient.

[10] A therapeutic, preventative and/or diagnostic agent for seizure in disease involving epileptic seizure or convulsive seizure (including multiple drug resistant seizure, refractory seizure, acute symptomatic seizure, febrile seizure and status epilepticus), comprising a compound or a salt thereof according to any of [1] to [8].

[11] The therapeutic, preventative or diagnostic agent according to wherein the epileptic seizure is selected from focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonic seizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizure of unknown onset including motor seizure (including tonic-clonic seizure and epileptic spasms) and non-motor seizure (including behavior arrest seizure).

[12] The therapeutic, preventative or diagnostic agent according to [10], wherein the disease involving epileptic seizure or convulsive seizure is selected from Dravet syndrome, Lennox-Gastaut syndrome, West syndrome (epilepsia nutans), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.), etc.

[13] A therapeutic, preventative and/or diagnostic pharmaceutical composition for seizure in disease involving epileptic seizure or convulsive seizure (including multiple drug resistant seizure, refractory seizure, acute symptomatic seizure, febrile seizure and status epilepticus), comprising a compound or a salt thereof according to any of [1] to [8]as an active ingredient.

[14] The composition according to [13], wherein the epileptic seizure is selected from focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonic seizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizures of unknown onset including motor seizure (including tonic-clonic seizure and epileptic spasms) and non-motor seizure (including behavior arrest seizure).

[15] The composition according to [13], wherein the disease involving epileptic seizure or convulsive seizure is selected from Dravet syndrome, Lennox-Gastaut syndrome, West syndrome (epilepsia *nutans*), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.), etc.

[16] A method for treating, preventing and/or diagnosing seizure in disease involving epileptic seizure or convulsive seizure (including multiple drug resistant seizure, refractory seizure, acute symptomatic seizure, febrile seizure and status epilepticus), wherein comprising administering to a human in need thereof an effective amount of a compound or a salt thereof according to any of [1] to [8].

[17] The method according to [16], wherein the epileptic seizure is selected from focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonic seizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizure of unknown onset including motor seizure (including tonic-clonic seizure and epileptic spasms) and non-motor seizure (including behavior arrest seizure).

[18] The method according to [16], wherein the disease involving epileptic seizure or convulsive seizure is selected from Dravet syndrome, Lennox-Gastaut syndrome, West syndrome (epilepsia *nutans*), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.), etc.

[19] A compound or a salt thereof according to any of [1] to [8] for use in the treatment, prevention and/or diagnosis of seizure in disease involving epileptic seizure or convulsive seizure (including multiple drug resistant seizure, refractory seizure, acute symptomatic seizure, febrile seizure and status epilepticus).

[20] The compound or a salt thereof according to [19], wherein the epileptic seizure is selected from focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonicseizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizure of unknown onset including motor seizure (including tonic-clonic seizure and epileptic spasms) and non-motor seizure (including behavior arrest seizure).

[21] The compound or a salt thereof according to [19], wherein the disease involving epileptic seizure or convulsive seizure is selected from Dravet syndrome, Lennox-Gastaut syndrome, West syndrome (epilepsia *nutans*), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.), etc.

[22] Use of a compound or a salt thereof according to any of [1] to [8] in the manufacture of a medicament for treating, preventing and/or diagnosing seizure in disease involving epileptic seizure or convulsive seizure (including multiple drug resistant seizure, refractory seizure, acute symptomatic seizure, febrile seizure and status epilepticus).

[23] The use according to [22], wherein the epileptic seizure is selected from focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonic seizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizure of unknown onset including motor seizure (including tonic-clonic seizure and epileptic spasms) and non-motor seizure (including behavior arrest seizure).

[24] The use according to [22], wherein the disease involving epileptic seizure or convulsive seizure is selected from Dravet syndrome, Lennox-Gastaut syndrome, West syndrome (epilepsia nutans), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.), etc.

The compound and a salt thereof of the present invention are highly effective for treating, preventing and/or diagnosing disease and the like involving epileptic seizure, convulsive seizure or the like. Moreover, the compound and a salt thereof of the present invention have excellent feature for use as active ingredient in pharmaceuticals, and for example have excellent feature such as few side effects, tolerability, stability (storage stability, metabolic stability, etc.) and the like. Furthermore, the compound and a salt thereof of the present invention have a wide treatment spectrum in comparison with existing antiepileptic drugs.

DESCRIPTION OF EMBODIMENTS

The phrases and terms used in this specification are explained in detail below.

The "$C_{1-6}$ alkyl" is $C_{1-6}$ linear or branched alkyl, and specific examples include methyl, ethyl, propyl, isopropyl, butyl, isobutyl, sec-butyl, tert-butyl, pentyl, isopentyl, neopentyl, hexyl, isohexyl, 3-methylpentyl and the like.

$C_{1-6}$ alkyl having deuterium atoms substituted for 1 to 3 hydrogen atoms is also included.

The "halogen" is fluorine, chlorine, bromine, or iodine. It is preferably fluorine, chlorine, or bromine, and more preferably fluorine or chlorine.

The "$C_{1-6}$ alkyl optionally substituted with halogen" is linear or branched alkyl having 1 to 6 carbon atoms ($C_{1-6}$) optionally substituted with 1 to 4 halogens, preferably 1 to 3 halogens, and specific examples thereof include methyl, ethyl, n-propyl, isopropyl, n-butyl, isobutyl, tert-butyl, sec-butyl, n-pentyl, isopentyl, neopentyl, n-hexyl, isohexyl, 3-methylpentyl, fluoromethyl, chloromethyl, bromomethyl, iodemethyl, difluoromethyl, dichloromethyl, dibromomethyl, trifluoromethyl, trichloromethyl, 2-fluoroethyl, 2-chloroethyl, 2,2,2-trifluoroethyl, 2,2,2-trichloroethyl, 1,1,2,2-tetrafluoroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dibromohexyl, and the like.

The "$C_{1-6}$ alkylene" is linear or branched alkylene having 1 to 6 carbon atoms ($C_{1-6}$). Specific examples thereof include methylene, ethylene, 1-methylethylene, 2-methylethylene, trimethylene, 2-methyltrimethylene, 2,2-dimethyltrimethylene, 1-methyltrimethylene, methylmethylene, ethylmethylene, dimethylmethylene, tetramethylene, pentamethylene, and hexamethylene.

In addition, "$C_{1-6}$ alkylene" also includes $C_{1-6}$ alkylene in which 1 to 3 hydrogen atoms are substituted with deuterium atoms.

Each of the groups defined in this specification may be bound appropriately to another group via a linker such as —O—, —CO—, —COO—, —S—, —SO—, —SO$_2$—, —Si—, —O—CO— or the like.

The various substituents in the compound represented by General Formula [I] of the present invention (hereafter called "compound [I] of the present invention") are explained below.

D in Compound [I] of the present invention is ring A optionally substituted with ($R^1$) k or $C_{1-6}$ alkyl optionally substituted with halogen.

The ring A in Compound [I] of the present invention is benzene, pyridine, indole or indazole, and is preferably benzene or pyridine.

When ring B is pyrimidine, ring C in Compound [I] of the present invention is selected from the group consisting of the following unsaturated rings and their oxides and dioxides (provided that pyrimidine-2,4-dione and dihydropyrimidine-2,4-dione are excluded), and those in which a part or all of unsaturated bonds in these rings are reduced with hydrogen;

(a) an unsaturated 3- to 8-membered monocyclic heterocycle containing 1 to 4 nitrogen atoms alone as ring-constituting heteroatom, (b) an unsaturated 7- to 15-membered bicyclic or tricyclic heterocycle containing 1 to 5 nitrogen atoms alone as ring-constituting heteroatom, (c) an unsaturated 7- to 12-membered bicyclic heterocycle containing 1 to 3 oxygen atoms alone as ring-constituting heteroatom, (d) an unsaturated 3- to 8-membered monocyclic heterocycle containing 1 to 2 oxygen atoms and 1 to 3 nitrogen atoms as ring-constituting heteroatom, (e) an unsaturated 7- to 12-membered bicyclic heterocycle containing 1 or 2 sulfur atoms and 1 to 3 nitrogen atoms as ring-constituting heteroatom, and (f) an unsaturated 3- to 8-membered monocyclic hydrocarbon ring.

Specific examples of an unsaturated 3- to 8-membered monocyclic heterocycle containing 1 to 4 nitrogen atoms alone as ring-constituting heteroatom in the above (a) and its oxide and dioxide (provided that pyrimidine-2,4-dione and dihydropyrimidine-2,4-dione are excluded), and the heterocycle in which a part or all of unsaturated bonds in its ring are reduced with hydrogen may include pyridine, piperidine, pyridine-1-oxide, pyridine-2 (1H)-one, pyrimidine, tetrahydropyrimidine, tetrahydropyrimidine-2 (1H)-one, pyridazine, pyridazine-3 (2H)-one, 4,5-dihydropyridazine, and 4,5-dihydropyridazine-3 (2H)-one.

Specific examples of an unsaturated 7- to 15-membered bicyclic or tricyclic heterocycle containing 1 to 5 nitrogen atoms alone as ring-constituting heteroatom in the above (b) and its oxide and dioxide, and the heterocycle in which a part or all of unsaturated bonds in its rings are reduced with hydrogen may include indole, indoline, indoline-2-one, indoline-3-one, indoline-2,3-dione, benzimidazole (for example, 1H-benzo[d]imidazole), dihydrobenzimidazole (for example, 2,3-dihydro-1H-benzo[d]imidazole), indazole, dihydroindazole (for example, 2,3-dihydro-1H-indazole), quinoline, quinoline-2 (1H)-one, dihydroquinoline (for example, 1,2-dihydroquinoline, 3,4-dihydroquinoline), 3,4-dihydroquinolin-2 (1H)-one, tetrahydroquinoline (for example, 1,2,3,4-tetrahydroquinoline), isoquinoline, isoquinoline-1 (2H)-one, 1,3-dihydroisoquinoline, 3,4-dihydroisoquinoline, 3,4-dihydroisoquinoline-1 (2H)-one, triazolopyrimidine (for example, [1,2,4]triazolo[1,5-a]pyrimidine), triazolopyridine (for example, [1,2,3]triazolo[1,5-a]pyridine, [1,2,4]triazolo[1,5-a]pyridine, [1,2,4]triazolo[4,3-a]pyridine), imidazopyridine (for example, imidazo[1,5-a]pyridine), imidazopyrazine (for example, imidazo[1,2-a]pyrazine), imidazopyrimidine (for example, imidazo[1,2-a]pyrimidine), imidazopyridazine (for example, imidazo[1,2-b]pyridazine), naphthyridine (for example, 1,5-naphthyridine, 1,8-naphthyridine), quinoxaline, dihydroquinoxaline (for example, 1,2-dihydroquinoxaline), tetrahydroquinoxaline (for example, 1,2,3,4-tetrahydroquinoxaline), quinazoline, quinazoline-4 (3H)-one, dihydroquinazoline (for example, 2,3-dihydroquinazoline), pyrazolopyridine (for example, pyrazolo[1,5-a]pyridine, pyrazolo[3,4-b]pyridine), pyrrolopyridine (for example, pyrrolo[2,3-b]pyridine), pyrrolo[2,3-b]pyridine-2 (3H)-one, and pyrazolopyrimidine (for example, pyrazolo[1,5-a]pyrimidine).

Specific examples of an unsaturated 7- to 12-membered bicyclic heterocycle containing 1 to 3 oxygen atoms alone as ring-constituting heteroatom in the above (c) and its oxide and dioxide, and the heterocycle in which a part or all of unsaturated bonds in its rings are reduced with hydrogen may include benzodioxole (for example, benzo[d][1,3]dioxole, benzo[c][1,2]dioxole).

Specific examples of an unsaturated 3- to 8-membered monocyclic heterocycle containing 1 to 2 oxygen atoms and 1 to 3 nitrogen atoms as ring-constituting heteroatom in the above (d) and its oxide and dioxide, and the heterocycle in which a part or all of unsaturated bonds in its ring are reduced with hydrogen may include oxazepine (for example, 1,2-oxazepine, 1,3-oxazepine, 1,4-oxazepine), dihydrooxazepine, tetrahydrooxazepine, oxazepan (for example, 1,2-oxazepan, 1,3-oxazepan, 1,4-oxazepan), 1,4-oxazepan-2-one, oxazine (for example, 1,4-oxazine), dihydrooxazine (3,4-dihydro-2H-1,4-oxazepine), morpholine, and morpholin-3-one.

Specific examples of an unsaturated 7- to 12-membered bicyclic heterocycle containing 1 or 2 sulfur atoms and 1 to 3 nitrogen atoms as ring-constituting heteroatom in the above (e) and its oxide and dioxide, and the heterocycle in which a part or all of unsaturated bonds in its rings are reduced with hydrogen may include benzothiazole (for example, benzo[d]thiazole).

Specific examples of an unsaturated 3- to 8-membered monocyclic hydrocarbon ring in the above (f) and its oxide and dioxide, and the heterocycle in which a part or all of unsaturated bonds in its ring are reduced with hydrogen may include benzene, cyclohexene, and cyclohexane.

When ring B is pyrimidine, preferably, ring C is selected from the group consisting of the following unsaturated rings and their oxides and dioxides (provided that pyrimidine-2,4-dione and dihydropyrimidine-2,4-dione are excluded), and those in which a part or all of unsaturated bonds in these rings are reduced with hydrogen:

pyridine,
pyridazine,
pyrimidine,
indole,
pyrrolopyridine,
indazole,
benzimidazole,
pyrazolopyridine,
imidazopyridine,
imidazopyrazine,
imidazopyridazine,
triazolopyridine,
pyrazolopyrimidine,
imidazopyrimidine,
triazolopyrimidine,
quinoline,
isoquinoline,
naphthyridine,
quinazoline,
quinoxaline,
benzodioxole,
oxazine,
oxazepine,
benzothiazole, and
benzene.

Regarding ring C in Compound [I] of the present invention, when ring B is benzene, naphthalene, pyridine, pyrazole or pyridazine, ring C is pyrimidine-2,4-dione or dihydropyrimidine-2,4-dione. Preferably, ring B is benzene or pyridine.

$R^1$ is halogen, $C_{1-6}$ alkyl optionally substituted with halogen, —O—$C_{1-6}$ alkyl optionally substituted with halogen, —CN or —SF$_5$, and preferably is halogen, $C_{1-6}$ alkyl optionally substituted with halogen or —O—$C_{1-6}$ alkyl optionally substituted with halogen, and more preferably is fluorine, methyl, trifluoromethyl, or —O-trifluoromethyl.

$R^2$ is halogen, $C_{1-6}$ alkyl or —O—$C_{1-6}$ alkyl, and preferably is fluorine, methyl or —O— methyl.

$R^3$ is halogen, $C_{1-6}$ alkyl optionally substituted with halogen or $C_{1-6}$ alkyl-O—, —O—$C_{1-6}$ alkyl optionally substituted with halogen, —$C_{1-6}$ alkyl-OH, —OH, —CN, —CONH$_2$ or —NH$_2$, preferably is $C_{1-6}$ alkyl optionally substituted with halogen, —O—$C_{1-6}$ alkyl, —OH, —CONH$_2$ or —NH$_2$, and most preferably methyl, trifluoromethyl, —O-methyl, —OH, —CONH$_2$ or —NH$_2$.

L is bond, C$_{1-6}$ alkylene, —O— or —S—, preferably is bond or —O—, and most preferably —O—.

k is 0, 1 or 2, and when k is 2, each R$^1$ independently represents the same or different substituent. 0 or 1 is preferable, and 0 is more preferable.

m is 0, 1 or 2, and when m is 2, each R$^2$ independently represents the same or different substituent. 0 or 1 is preferable, and 0 is more preferable.

n is 0, 1 or 2, and when n is 2, each R$^3$ independently represents the same or different substituent. 0 or 1 is preferable.

Presentation of options relating to the above substituents and preferable aspects of Compound [I] of the present invention include all combinations thereof as long as they are combinations with no contradiction.

Preferable aspects of Compound [I] of the present invention are shown below. (1-1) In Formula I, D is

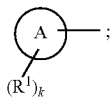

ring A is benzene or pyridine;
ring B is pyrimidine;
ring C is selected from the group consisting of the following unsaturated rings and their oxides and dioxides (provided that pyrimidine-2,4-dione and dihydropyrimidine-2,4-dione are excluded), and those in which a part or all of unsaturated bonds in these rings are reduced with hydrogen:
pyridine,
pyridazine,
pyrimidine,
indole,
pyrrolopyridine,
indazole,
benzimidazole,
pyrazolopyridine,
imidazopyridine,
imidazopyrazine,
imidazopyridazine,
triazolopyridine,
pyrazolopyrimidine,
imidazopyrimidine,
triazolopyrimidine,
quinoline,
isoquinoline,
naphthyridine,
quinazoline,
quinoxaline,
benzodioxole,
oxazine,
oxazepine,
benzothiazole, and
benzene;
R$^1$ is halogen, C$_{1-6}$ alkyl optionally substituted with halogen, —O—C$_{1-6}$ alkyl optionally substituted with halogen or —CN;
R$^2$ is —O—C$_{1-6}$ alkyl;
R$^3$ is halogen, C$_{1-6}$ alkyl optionally substituted with halogen or —O—C$_{1-6}$ alkyl, —O—C$_{1-6}$ alkyl optionally substituted with halogen, —C$_{1-6}$ alkyl-OH, —OH, —CN, —CONH$_2$ or —NH$_2$;

L is —O—;
k is 0, 1 or 2, and when k is 2, each R$^1$ independently represents the same or different substituent;
m is 0 or 1; and
n is 0, 1 or 2, and when n is 2, each R$^3$ independently represents the same or different substituent.

(1-2) In Formula I, ring C is selected from the group consisting of the following unsaturated rings and their oxides, and those in which a part or all of unsaturated bonds in these rings are reduced with hydrogen:
pyridine,
pyridazine,
pyrrolopyridine,
indazole,
pyrazolopyridine,
imidazopyridine,
imidazopyrazine,
imidazopyridazine,
pyrazolopyrimidine,
triazolopyrimidine,
quinoline,
isoquinoline,
naphthyridine,
quinoxaline, and
benzene;
R$^1$ is halogen or C$_{1-6}$ alkyl optionally substituted with halogen;
R$^3$ is C$_1$-6 alkyl optionally substituted with halogen, —O—C$_{1-6}$ alkyl optionally substituted with halogen, —OH, —CONH$_2$ or —NH$_2$;
L is —O—;
k and n are 0 or 1; and
m is 0.

(1-3) In Formula I, ring C is selected from the group consisting of the following unsaturated rings and their oxides, and those in which a part or all of unsaturated bonds in these rings are reduced with hydrogen:
pyridine,
pyridazine,
pyrazolopyridine, and
Imidazopyridine;
R$^3$ is —OH or —NH$_2$;
L is —O—;
k and m are 0; and
n is 0 or 1.

(1-4) A compound selected from the group consisting of the following compounds:

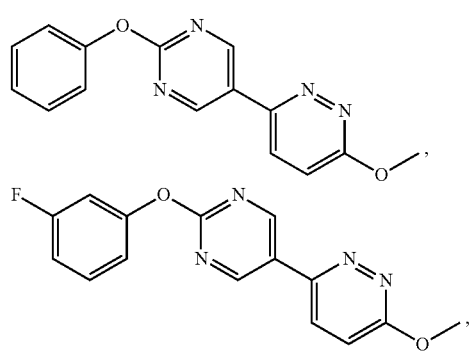

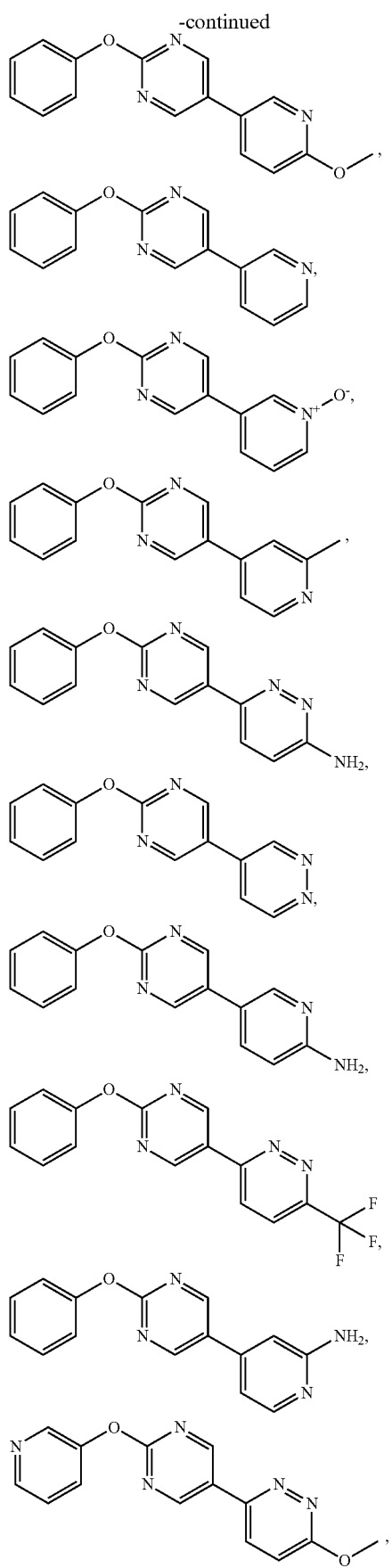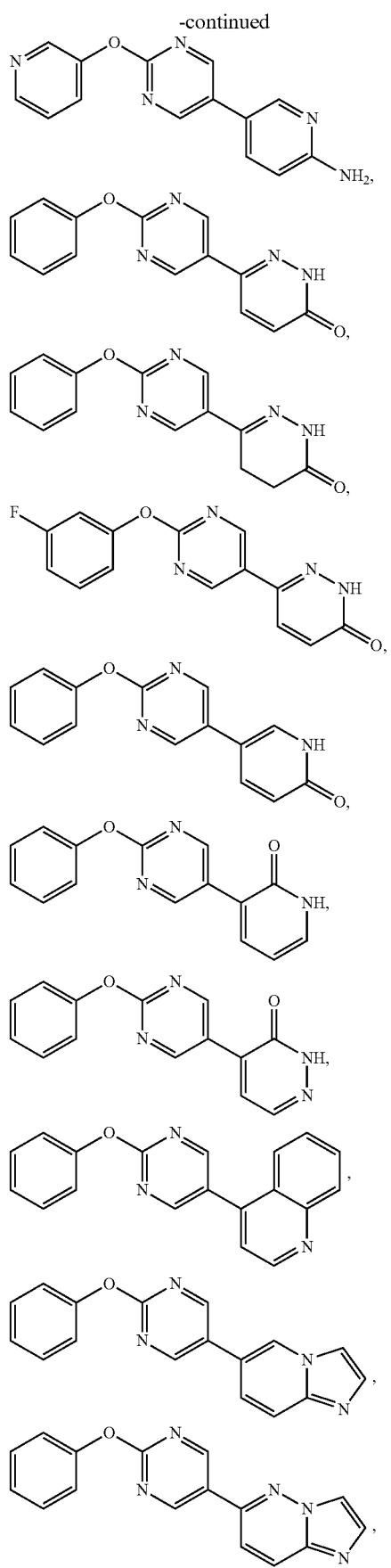

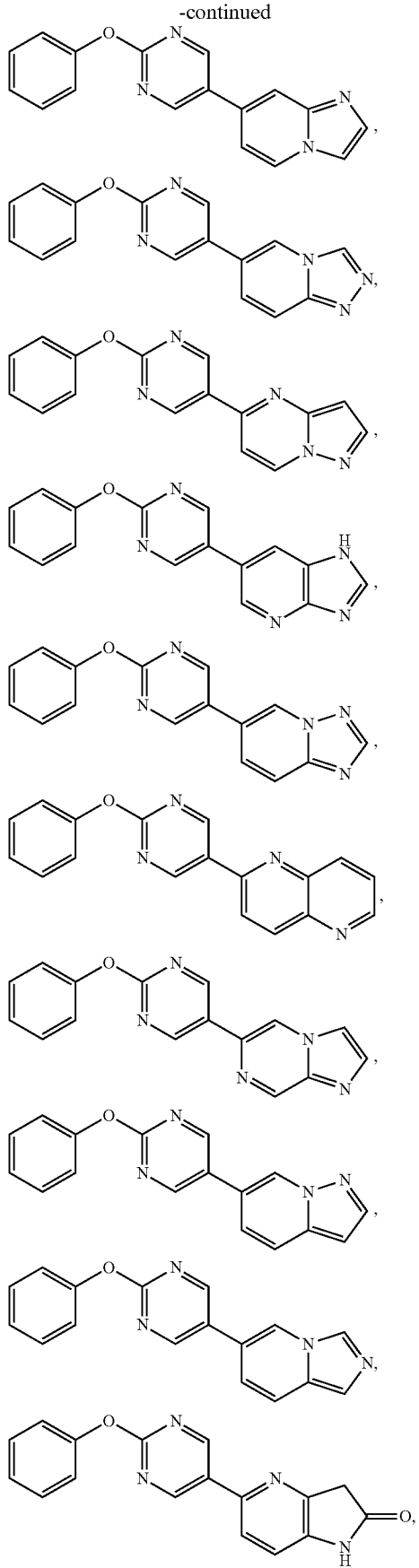
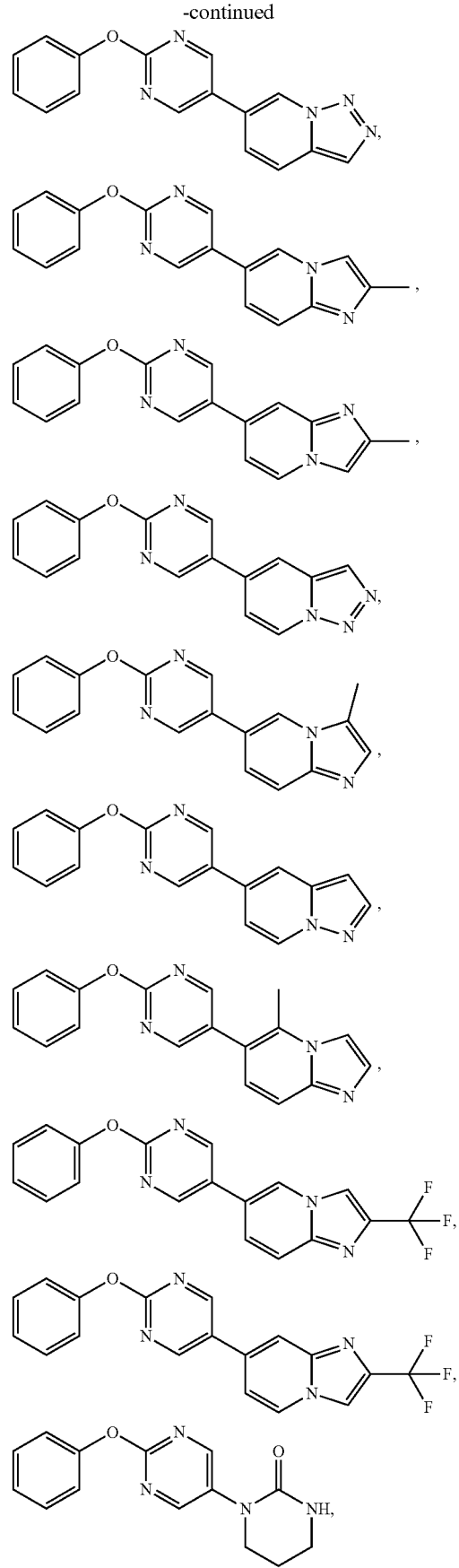

-continued
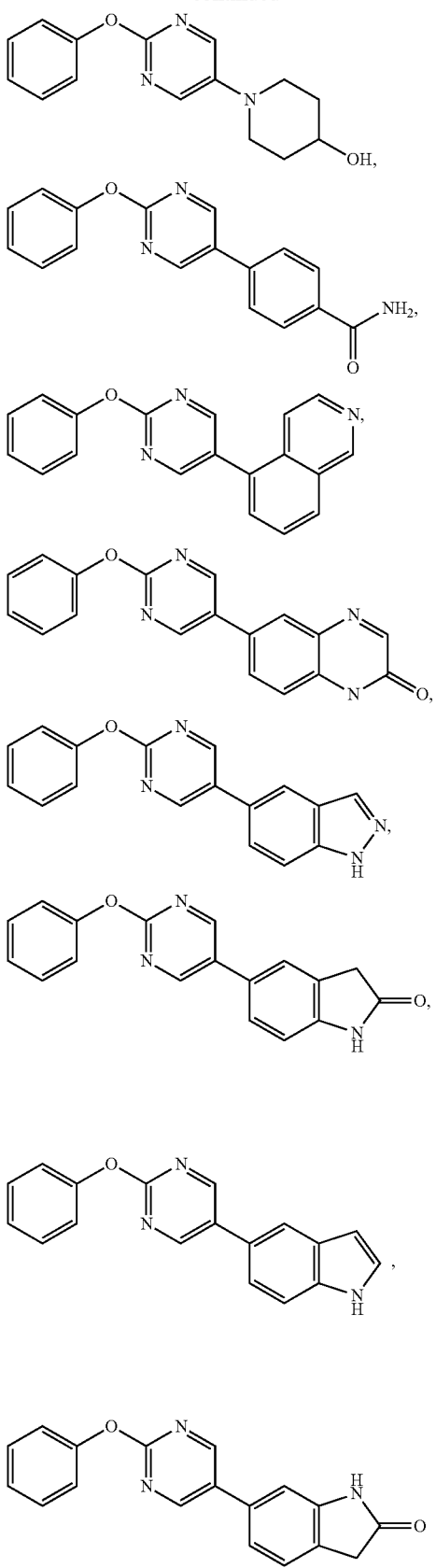
or a salt thereof.
(1-5) A compound selected from the group consisting of the following compounds:
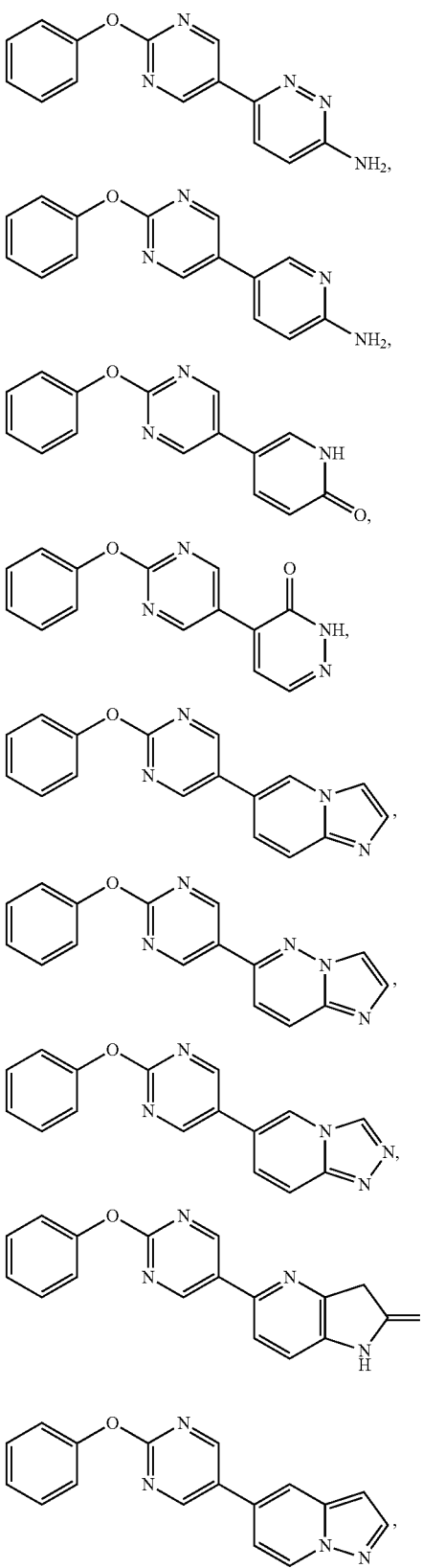

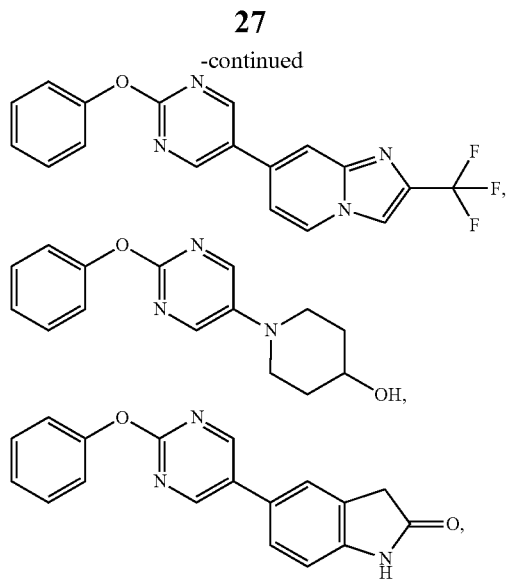

or a salt thereof.

Other preferable aspects of Compound [I] of the present invention are shown below. (2-1) In Formula I, D is

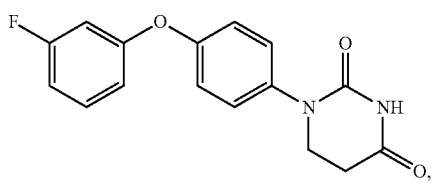

or $C_{1-6}$ alkyl optionally substituted with halogen;
ring A is benzene or pyridine;
ring B is pyridazine, pyridine, pyrazole, benzene, or naphthalene;
ring C is pyrimidine-2,4-dione or dihydropyrimidine-2,4-dione;
$R^1$ is halogen, $C_{1-6}$ alkyl optionally substituted with halogen, —O—$C_{1-6}$ alkyl optionally substituted with halogen, —CN or —$SF_5$;
$R^2$ is halogen, $C_{1-6}$ alkyl, or —O—$C_{1-6}$ alkyl; $R^3$ is $C_1$-6 alkyl;
L is bond, $C_{1-6}$ alkylene, —O— or —S—;
k is 0, 1 or 2, and when k is 2, each $R^1$ independently represents the same or different substituent;
m is 0, 1 or 2, and when m is 2, each $R^2$ independently represents the same or different substituent; and
n is 0, 1 or 2, and when n is 2, each $R^3$ independently represents the same or different substituent.
(2-2) In Formula I, ring A is benzene;
ring B is benzene, pyridine, or pyridazine;
ring C is dihydropyrimidine-2,4-dione;
$R^1$ is halogen;
L is —O—;
k is 0 or 1; and
m and n are 0.
(2-3) A compound selected from the group consisting of the following compounds:

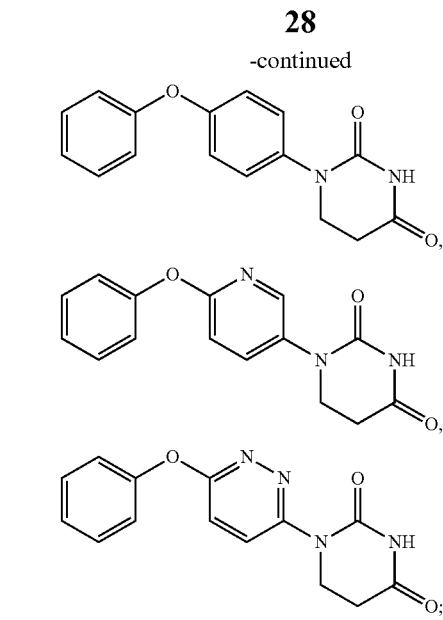

or a salt thereof.
(2-4) A compound:

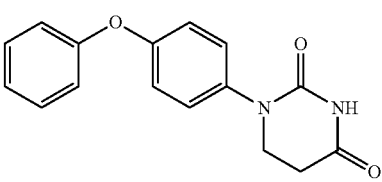 [SMILES: O=C1CCN(c2ccc(Oc3ccccc3)cc2)C(=O)N1]

or a salt thereof.

In this specification, the options and preferred embodiments for the different features of the compound, method and composition of the present invention as presented include all possible combinations of the options and preferred embodiments for these different features as long as they are consistent combinations.

Methods for manufacturing the compound [I] of the present invention are explained below. The compound [I] of the present invention can be manufactured based on the manufacturing methods described below for example. The manufacturing methods described below are examples, and the method for manufacturing the compound [I] is not limited thereby.

In the reaction formulae below, when performing an alkylation reaction, hydrolysis reaction, amination reaction, esterification reaction, amidation reaction etherification reaction, nucleophilic substitution reaction, addition reaction, oxidation reaction, reduction reaction or the like, these reactions are themselves performed by known methods. Examples of such methods include the methods described in Experimental Chemistry (Fifth Edition, edited by The Chemical Society of Japan, Maruzen Co., Ltd.); Organic Functional Group Preparations Second Edition, Academic Press, Inc., 1989; Comprehensive Organic Transformations, VCH Publishers, Inc., 1989; and P.G.M. Wuts and T.W. Greene, Greene's Protective Groups in Organic Synthesis (Fourth Edition, 2006) and the like.

Reaction Formula 1-1

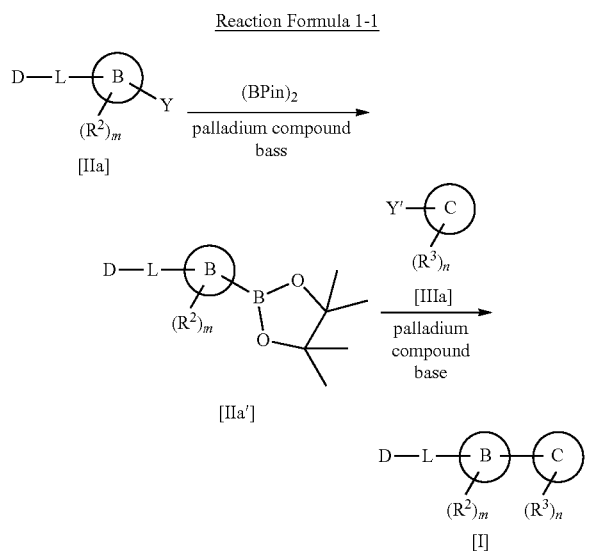

wherein Y and Y' represent a leaving group, and the other symbols have the same definitions as above.

According to the reaction represented by Reaction Formula 1-1, Compound [I] of the present invention can be produced. Specifically, cyclic pinacol ester ((BPin)$_2$) of boronic acid can be added to Compound [IIa] to obtain Compound [IIa'], and then Compound [IIa'] can be bonded to Compound [IIIa] by Suzuki cross coupling to produce Compound [I].

Examples of the "leaving group" used in the reaction above include halogen, $C_{1-18}$ alkanesulfonyl, $C_{1-8}$ alkanesulfonyloxy, arylsulfonyloxy, aralkylsulfonyloxy, trihalomethanesulfonyloxy, sulfonio, toluenesulfoxy and the like. Examples of preferred leaving group in the reaction include halogen.

The "halogen" is fluorine, chlorine, bromine or iodine.

Examples of the "$C_{1-18}$ alkanesulfonyl" include $C_{1-18}$ linear or branched alkanesulfonyl, and specific examples include methanesulfonyl, 1-propanesulfonyl, 2-propanesulfonyl, butanesulfonyl, cyclohexanesulfonyl, dodecanesulfonyl, octadecanesulfonyl and the like.

Examples of the "lower alkanesulfonyloxy" include $C_{1-6}$ linear or branched alkanesulfonyloxy, and specific examples include methanesulfonyloxy, ethanesulfonyloxy, 1-propanesulfonyloxy, 2-propanesulfonyloxy, 1-butanesulfonyloxy, 3-butanesulfonyloxy, 1-pentanesulfonyloxy, 1-hexanesulfonyloxy and the like.

Examples of the "arenesulfonyloxy" include naphthalenesulfonyloxy and benzenesulfonyloxy, which may have 1 to 3 substituents selected from the group consisting of halogen, nitro, $C_{1-6}$ linear or branched alkoxy and $C_{1-6}$ linear or branched alkyl groups on the phenyl ring. Specific examples of these "benzenesulfonyloxy which may have substituents" include benzenesulfonyloxy, 4-methylbenzenesulfonyloxy, 2-methylbenzenesulfonyloxy, 4-nitrobenzenesulfonyloxy, 4-methoxybenzenesulfonyloxy, 2-nitrobenzenesulfonyloxy, 3-chlorobenzenesulfonyloxy and the like. Specific examples of "naphthalenesulfonyloxy" include α-naphthalenesulfonyloxy, β-naphthalenesulfonyloxy and the like.

Examples of the "aralkanesulfonyloxy" include naphthyl-substituted $C_{1-6}$ linear or branched alkanesulfonyloxy and phenyl-substituted $C_{1-6}$ linear or branched alkanesulfonyloxy which may have 1 to 3 substituents selected from the group consisting of halogen, nitro, $C_{1-6}$ linear or branched alkoxy and $C_{1-6}$ linear or branched alkyl on the phenyl ring. Specific examples of these "phenyl-substituted alkanesulfonyloxy" include phenylmethanesulfonyloxy, 2-phenylethanesulfonyloxy, 4-phenylbutanesulfonyloxy, 4-tolylmethanesulfonyloxy, 2-tolylmethanesulfonyloxy, (4-nitrophenyl) methanesulfonyloxy, (4-methoxyphenyl) methanesulfonyloxy, (3-chlorophenyl) methanesulfonyloxy and the like. Examples of "naphthyl-substituted alkanesulfonyloxy" include α-naphthylmethanesulfonyloxy, β-naphthylmethanesulfonyloxy and the like.

A specific example of "trihaloalkanesulfonyloxy" group is trifluoromethanesulfonyloxy.

Specific examples of the "sulfonio" include dimethylsulfonio, diethylsulfonio, dipropylsulfonio, di(2-cyanoethyl) sulfonio, di(2-nitroethyl) sulfonio, di-(aminoethyl) sulfonio, di(2-methylaminoethyl) sulfonio, di-(2-dimethylaminoethyl) sulfonio, di-(2-hydroxyethyl) sulfonio, di-(3-hydroxypropyl) sulfonio, di-(2-methoxyethyl) sulfonio, di-(2-carbamoylethyl) sulfonio, di-(2-carboxyethyl) sulfonio, di-(2-methoxycarbonylethyl) sulfonio, diphenylsulfonio and the like.

The "palladium compound" to be used in the present reaction is not particularly limited, and examples thereof include tetravalent palladium catalysts such as sodium hexachloropalladium (IV) acid tetrahydrate and potassium hexachloropalladium (IV) acid; divalent palladium catalysts such as [1,1'-bis(diphenylphosphino) ferrocene]palladium (II) dichloride dichloromethane adduct (Pd(dppf) Cl$_2$·CH$_2$Cl$_2$), (2-dicyclohexylphosphino-2',4',6'-triisopropyl-1,1'-biphenyl) [2-(2'-amino-1,1'-biphenyl)]palladium (II) methanesulfonate (XPhos Pd G3), palladium (II) chloride, palladium (II) bromide, palladium (II) acetate, palladium (II) acetylacetonate, dichlorobis(benzonitrile) palladium (II), dichlorobis(acetonitrile) palladium (II), dichlorobis(triphenylphosphine) palladium (II), dichlorotetraammine palladium (II) and dichloro(cycloocta-1,5-diene) palladium (II), palladium (II) trifluoroacetate; and zerovalent palladium catalysts such as tris(dibenzylideneacetone) dipalladium (0) (Pd$_2$ (dba)$_3$), tris(dibenzylideneacetone) dipalladium (0)-chloroform complex, and tetrakis(triphenylphosphine) palladium (0) (Pd(PPh$_3$)$_4$). These palladium compounds are used alone or as a mixture of two or more of them.

In the present reaction, the amount of the palladium compound used is not particularly limited and is usually in the range of 0.000001 to 20 mol in terms of palladium with respect of 1 mol of compound [IIa]. More preferably, the amount of the palladium compound used is in the range of 0.0001 to 5 mol in terms of palladium with respect of 1 mol of compound [IIa].

Examples of the "base" to be used in the present reaction include an inorganic base, an organic base, and the like. Examples of the "inorganic base" include an alkali metal hydroxide (e.g., sodium hydroxide and potassium hydroxide), an alkaline earth metal hydroxide (e.g., magnesium hydroxide and calcium hydroxide), an alkali metal carbonate (e.g., sodium carbonate and potassium carbonate), an alkaline earth metal carbonate (e.g., magnesium carbonate and calcium carbonate), an alkali metal hydrogen carbonate (e.g., sodium hydrogen carbonate and potassium hydrogen carbonate), an alkali metal phosphate (e.g., sodium phosphate and potassium phosphate), an alkaline earth metal phosphate (e.g., sodium phosphate and potassium phosphate). Examples of the "organic bases" include trialkylamines (e.g., trimethylamine, triethylamine, and diisopropylethylamine), dialkylamines (e.g., diethylamine, diisopropylamine), picoline, 1,5-diazabicyclo[4.3.0]non-5-ene, 1,4-diazabicyclo[2.2.2]octane, and 1,8-diazabicyclo[5.4.0]undec-7-ene (DBU). These bases are used alone or as a mixture of two or more of them.

Regarding "boronic acid" or "boronic acid ester" used in this reaction, those separately produced, isolated and purified may be used. For example, bispinacol diborane may be reacted with a halogenated compound of a precursor and the like in the presence of a palladium compound, and the reaction product may be used for Suzuki cross coupling without isolation and purification.

The "solvent" used in this reaction may be any solvent that is inactive in the reaction, and examples thereof include water, ethers (such as dioxane, tetrahydrofuran, diethyl ether, 1,2-dimethoxyethane, diethylene glycol dimethyl ether or ethylene glycol dimethyl ether), hydrocarbons (such as hexane), halohydrocarbons (such as methylene chloride, chloroform, 1,2-dichloroethane or carbon tetrachloride), aromatic hydrocarbons (such as benzene, toluene or xylene), lower alcohols (such as methanol, ethanol or isopropanol), polar solvents (such as N,N-dimethylformamide (DMF), N-methylpyrrolidine (NMP), dimethyl sulfoxide (DMSO), hexamethylphosphoric acid triamide or acetonitrile), ketons (such as acetone or methylethylketone), esters (such as methyl acetate or ethyl acetate). One of these solvents alone or a mixture of two or more kinds may be used.

Other reaction conditions (a reaction temperature, a reaction time, etc.) can be appropriately determined based on a known Suzuki cross coupling reaction.

Reaction Formula 1-2

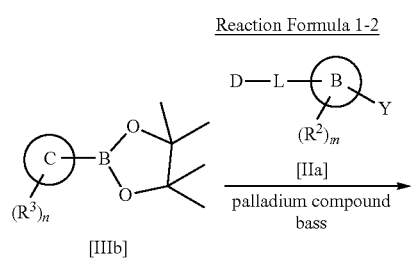

wherein Y is a leaving group, and the other symbols have the same definitions as above.

According to the reaction represented by Reaction Formula 1-2, Compound [I] of the present invention can be produced. Specifically, Compound [IIa] can be bonded to Compound [IIIb] by Suzuki cross coupling to produce Compound [I].

The palladium compound, base, solvent, and the like that can be used in Reaction Formula 1-2 are the same as those that can be used in Reaction Formula 1-1.

Reaction Formula 1-3

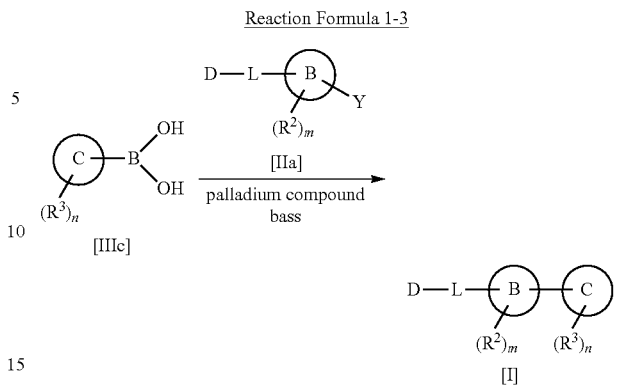

wherein Y is a leaving group, and the other symbols have the same definitions as above.

Compound [I] of the present invention can be produced according to the reaction represented by Reaction Formula 1-3. Specifically, Compound [IIa] can be bonded to Compound [IIIc] by Suzuki cross coupling to produce Compound [I].

The palladium compound, base, solvent, and the like that can be used in Reaction Formula 1-3 are the same as those that can be used in Reaction Formula 1-1.

Reaction Formula 2-1

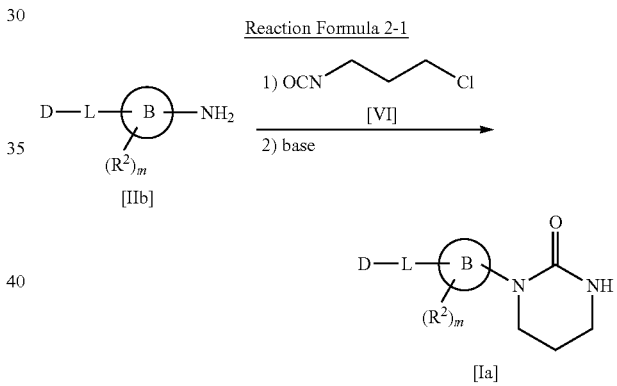

wherein symbols have the same definitions as above.

According to the reaction represented by Reaction Formula 2-1, Compound [Ia] included in Compound [I] of the present invention can be produced. Specifically, Compound [VI] is added to an amino group of Compound [IIb], and chlorine of the product is then released for cyclization, and thus Compound [Ia] can be produced.

Examples of "base" used in this reaction include inorganic bases and organic bases. Examples of "inorganic base" include alkali metal hydroxides (for example, sodium hydroxide, potassium hydroxide), alkali metal carbonates (for example, sodium carbonate, potassium carbonate), alkali metal bicarbonates (for example, sodium bicarbonate, potassium bicarbonate), sodium hydride (NaH), and sodium hexamethyldisilazide (NaHMDS). Examples of "organic base" include trialkylamines (for example, trimethylamine, triethylamine), Huenig's base (N,N-diisopropylethylamine), pyridine, and N-methylmorpholine.

The "solvent" used in this reaction may be any solvent that is inactive in the reaction, and examples thereof include water, ethers (such as dioxane, tetrahydrofuran, diethyl ether, 1,2-dimethoxyethane, diethylene glycol dimethyl ether or ethylene glycol dimethyl ether), hydrocarbons (such as hexane), halohydrocarbons (such as methylene chloride, chloroform, 1,2-dichloroethane or carbon tetrachloride), aromatic hydrocarbons (such as benzene, toluene or xylene), lower alcohols (such as methanol, ethanol or isopropanol), polar solvents (such as N,N-dimethylformamide (DMF), N-methylpyrrolidine (NMP), dimethyl sulfoxide (DMSO), hexamethylphosphoric acid triamide or acetonitrile), ketons (such as acetone or methylethylketone), esters (such as methyl acetate or ethyl acetate). One of these solvents alone or a mixture of two or more kinds may be used.

Other reaction conditions (reaction temperature, reaction time, etc.) can be appropriately determined based on a generally known condensation reaction. For example, the reaction temperature may be from room temperature to a heating reflux temperature of a solvent, and the reaction time may be from 10 minutes to 10 hours.

Reaction Formula 2-2

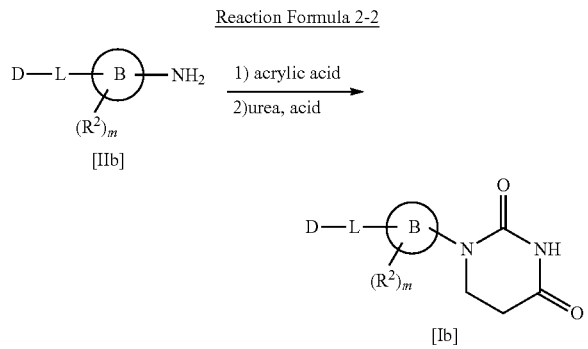

wherein symbols have the same definitions as above.

According to the reaction represented by Reaction Formula 2-2, Compound [Ib]included in Compound [I] of the present invention can be produced. Specifically, Compound [III](acrylic acid) is 1,4-added to an amino group of Compound [IIb] and next, an amino group of the product is converted into a urea derivative using urea and cyclized (intramolecular amidation), and thus Compound [Ib] can be produced.

The "solvent" used in this reaction may be any solvent that is inactive in the reaction, and examples thereof include water, ethers (such as dioxane, tetrahydrofuran, diethyl ether, 1,2-dimethoxyethane, diethylene glycol dimethyl ether or ethylene glycol dimethyl ether), hydrocarbons (such as hexane), halohydrocarbons (such as methylene chloride, chloroform, 1,2-dichloroethane or carbon tetrachloride), aromatic hydrocarbons (such as benzene, toluene or xylene), lower alcohols (such as methanol, ethanol or isopropanol), polar solvents (such as N,N-dimethylformamide (DMF), N-methylpyrrolidine (NMP), dimethyl sulfoxide (DMSO), hexamethylphosphoric acid triamide or acetonitrile), ketons (such as acetone or methylethylketone), esters (such as methyl acetate or ethyl acetate). One of these solvents alone or a mixture of two or more kinds may be used.

Examples of "acid" used in the reaction include inorganic acids and organic acids. Examples of "inorganic acid" include hydrochloric acid, sulfuric acid, nitric acid, hydrobromic acid, and phosphoric acid. Examples of "organic acid" include acetic acid, trifluoroacetic acid, oxalic acid, phthalic acid, fumaric acid, tartaric acid, maleic acid, citric acid, succinic acid, methanesulfonic acid, p-toluenesulfonic acid, and 10-camphorsulfonic acid.

Other reaction conditions (reaction temperature, reaction time, etc.) can be appropriately determined based on a generally known 1,4-addition reaction, and amidation reaction.

Reaction Formula 3-1

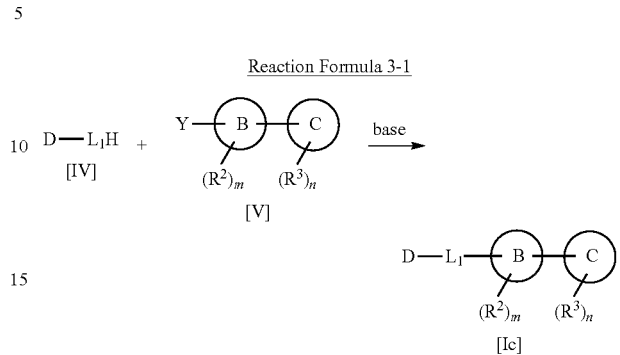

wherein Y is a leaving group, $L_1$ is —O—, —S—, or $C_{1-6}$ alkylene, and the other symbols have the same definitions as above.

According to the reaction represented by Reaction Formula 3-1, Compound [Ic] included in Compound [I] of the present invention can be produced. Specifically, Compound [Ic] can be produced by releasing a leaving group Y of Compound [V] and substituting with Compound [IV].

Examples of "base" used in this reaction include inorganic bases. Examples of "inorganic base" include alkali metal hydroxides (for example, sodium hydroxide, potassium hydroxide), alkali metal carbonates (for example, sodium carbonate, potassium carbonate), alkali metal bicarbonates (for example, sodium bicarbonate, potassium bicarbonate), sodium hydride (NaH), and sodium hexamethyldisilazide (NaHMDS). Examples of "organic base" include trialkylamines (for example, trimethylamine, triethylamine), Huenig's base (N,N-diisopropylethylamine), pyridine, and N-methylmorpholine.

The "solvent" used in this reaction may be any solvent that is inactive in the reaction, and examples thereof include water, ethers (such as dioxane, tetrahydrofuran, diethyl ether, 1,2-dimethoxyethane, diethylene glycol dimethyl ether or ethylene glycol dimethyl ether), hydrocarbons (such as hexane), halohydrocarbons (such as methylene chloride, chloroform, 1,2-dichloroethane or carbon tetrachloride), aromatic hydrocarbons (such as benzene, toluene or xylene), lower alcohols (such as methanol, ethanol or isopropanol), polar solvents (such as N,N-dimethylformamide (DMF), N-methylpyrrolidine (NMP), dimethyl sulfoxide (DMSO), hexamethylphosphoric acid triamide or acetonitrile), ketons (such as acetone or methylethylketone), esters (such as methyl acetate or ethyl acetate). One of these solvents alone or a mixture of two or more kinds may be used.

Other reaction conditions (a reaction temperature, a reaction time, etc.) can be appropriately determined based on a generally known condensation reaction. For example, the reaction temperature may be from room temperature to 100° C., and the reaction time may be 1 hour to 10 hours.

In each of the reactions in the above reaction formulae, the reaction product can be used in the next reaction either as is in the form of the reaction solution or as a crude product, but it can also be isolated from the reaction mixture by normal methods and easily purified by normal separation techniques. Examples of normal separation techniques include recrystallization, distillation and chromatography.

The starting raw material compounds, intermediate compounds and object compounds in each of the above steps and the compound [I] of the present invention itself all include geometric isomers, stereoisomers, optical isomers and tautomers. The respective isomers can be separated by ordinary optical resolution methods. They can also be manufactured from raw material compounds having suitable optical activity.

The compound [I] of the present invention can be manufactured by the synthesis methods shown in the reaction formulae above, or by analogous methods.

Unless specific production methods are specified, the raw material compounds used in the manufacture of the compound [I] of the present invention may be commercial compounds, or may be produced by known methods or analogous methods.

The starting raw material compounds and object compounds in each step above may be used in the form of appropriate salts. Examples of such salts include salts similar to those given as examples of salts of compound [I] of the present invention below.

When the compounds obtained in each step or commercial products are free compounds, they can be converted to the object salts by known methods. When the compounds obtained in each step or commercial products are salts, they can be converted to free form or into other object salts by known methods.

The compound [I] of the present invention also includes embodiments that are pharmaceutically acceptable salts, and in some cases the compounds may also form an acid addition salt or a salt with a base depending on the kinds of substituents. Examples of the "acid" here include inorganic acids such as hydrochloric acid, hydrobromic acid, nitric acid, sulfuric acid and phosphoric acid; and organic acids such as methanesulfonic acid, p-toluenesulfonic acid, acetic acid, citric acid, tartaric acid, maleic acid, fumaric acid, malic acid, lactic acid and the like. Examples of the "base" include inorganic bases such as sodium hydroxide, potassium hydroxide, calcium hydroxide, sodium carbonate, potassium carbonate, sodium bicarbonate and potassium bicarbonate; organic bases such as methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline and choline; and ammonium salts and the like. The compound may also form a salt with an amino acid such as lysine, arginine, aspartic acid, glutamic acid or the like.

The present invention also encompasses various hydrates, solvates and crystal polymorphisms of the compound [I] and salts thereof.

The compound [I] of the present invention also includes compounds in which one or more isotope atoms have been substituted for one or more atoms. Examples of isotope atoms include deuterium (2H), tritium (3H), 13C, 15N, 18O and the like.

The compound [I] of the present invention includes pharmaceutically acceptable prodrugs. Examples of substituents that can be modified to make prodrugs include reactive functional groups such as —OH, —COOH, amino and the like. The modifying groups of these functional groups are selected appropriately from the "substituents" in this specification.

The compound [I] or a salt thereof of the present invention may be in the form of a pharmaceutically acceptable co-crystal or co-crystal salts. A co-crystal or co-crystal salt here means a crystalline substance composed at room temperature of two or more independent solids each having different physical properties (such as structure, melting point, heat of fusion and the like). Co-crystals and co-crystal salts can be manufactured appropriately by well-known co-crystallization methods.

The compound [I] and a salt thereof of the present invention have excellent effects in the treatment, prevention and/or diagnosis of seizure in disease involving epileptic seizure or convulsive seizure. The term epileptic seizure is applicable to any of the seizure types classified below: focal onset seizure (also called partial seizure) with motor onset (including automatism, atonic seizure, clonic seizure, epileptic spasms, hyperkinetic seizure, myoclonic seizure and tonic seizure) and non-motor onset (including autonomic seizure, behavior arrest seizure, cognitive seizure, emotional seizure and sensory seizure), and focal to bilateral tonic-clonic seizure (secondary generalization of partial seizure); generalized onset seizure including motor seizure (including tonic-clonic seizure, clonic seizure, tonic seizure, myoclonic seizure, myoclonic-tonic-clonic seizure, myoclonic-atonic seizure, atonic seizure and epileptic spasms) and non-motor seizure (including typical absence seizure, atypical absence seizure, myoclonic absence seizure and eyelid myoclonic seizure); and seizures of unknown onset including motor seizure (including tonic-clonic seizure and epileptic spasms) and non-motor seizure (including behavior arrest seizure).

Examples of the disease involving epileptic seizure or convulsive seizure include Dravet syndrome, Lennox-Gastaut syndrome, West syndrome (epilepsia *nutans*), Ohtahara syndrome, Doose syndrome, Landau-Kleffner syndrome, Rasmussen syndrome, Aicardi syndrome, Panayiotopoulos syndrome, Kojewnikow syndrome, Tassinari syndrome, Geschwind syndrome, hemiconvulsion-hemiplegia-epilepsy syndrome, mesial temporal lobe epilepsy, epilepsy with structural/metabolic cause (epilepsy after stroke, traumatic epilepsy, infectious epilepsy, epilepsy associated with cerebrovascular disorder, epilepsy associated with brain tumor, epilepsy associated with neurodegenerative disease, epilepsy associated with autoimmune disorder, etc.), and congenital malformation, congenital metabolic abnormality (for example, phenylketonuria, mitochondrial disease, lysosomal disease, Sturge-Weber syndrome, etc.) and congenital genetic abnormality (Rett's syndrome, Angelman's syndrome, 5p syndrome, 4p syndrome, Down's syndrome, etc.).

The compound [I] or a salt thereof of the present invention is also effective in the treatment, prevention and/or diagnosis of multiple drug resistant seizure, refractory seizure, acute symptomatic seizure, febrile seizure and status epilepticus. In the present invention, multiple drug resistant seizure and refractory seizure are defined as seizure that cannot be controlled because one or two or more antiepileptic drugs are ineffective or insufficiently effective or the like, regardless of the type of epileptic seizure as described above.

Moreover, the compound [I] and a salt thereof of the present invention have excellent features for use as active ingredients in pharmaceuticals, and for example have excellent features such as few side effects, tolerability, stability (storage stability, metabolic stability, etc.) and the like. These groups of compounds of the present invention also have effects as preventative and/or therapeutic agents against refractory epileptic seizure in which conventional drug therapy is not successful.

Next, a medical preparation (hereunder also called a "pharmaceutical composition") containing a compound [I] or a salt thereof of the present invention as an active ingredient is explained.

The medical preparation is obtained by formulating a compound [I] or a salt thereof of the present invention in the form of an ordinary medical preparation, and is prepared using a compound [I] or a salt thereof of the present invention and a pharmaceutically acceptable carrier. Examples of the carrier include commonly used diluents or excipients such as fillers, bulking agents, binders, humectants, disintegrants, surfactants, lubricants and the like.

Such a medical preparation can be selected from various forms according to the therapeutic objective, and examples thereof include tablets, pills, powders, liquids, suspensions, emulsions, granules, capsules, suppositories, injections (liquids, suspensions, etc.) and the like.

A wide range of known carriers may be used when molding the preparation in the form of a tablet, and examples thereof include excipients such as lactose; binders such as polyvinylpyrrolidone; disintegrants such as starch; absorption aids such as sodium lauryl sulfate; humectants such as glycerin and starch; adsorbants such as colloidal silicic acid; and lubricants such as magnesium stearate, polyethylene glycol and the like.

Moreover, the tablet may as necessary be made into a tablet with an ordinary coating, such as for example a sugar-coated tablet, gelatin-coated tablet, enteric coated tablet, film-coated tablet, double tablet or multilayer tablet.

A wide range of known carriers may be used when molding the preparation in the form of a pill, and examples thereof include excipients such as glucose; binders such as gum arabic powder; and disintegrants such as laminaran and the like . . .

A wide range of known diluents may be used when forming the preparation as a liquid, emulsion or suspension, and examples thereof include water and the like. Ordinary solubilizing agents and buffers may also be included, as well as colorants, preservatives, aromatics, flavorings, sweeteners and other drugs and the like as necessary.

A wide range of known carriers may be used when forming the preparation as a suppository, and examples thereof include cocoa butter and the like.

When the preparation is an injection, the liquid, emulsion or suspension is preferably sterilized, and is also preferably isotonic with blood. An amount of sodium chloride sufficient to prepare an isotonic injection may be included in the injection, and another drug, soothing agent or the like may also be included.

The amount of the compound [I] or a salt thereof that is contained in the medical preparation is not particularly limited and may be selected appropriately from a wide range, but normally the compound [I] or a salt thereof of the present invention is preferably contained in the amount of 1% to 70% of the medical preparation.

The method for administering the medical preparation of the present invention is not particularly limited, and it can be administered by a method suited to the dosage form, the age and sex of the patient, the disease status and other conditions. For example, it can be administered orally if it is in the form of a tablet, pill, liquid, suspension, emulsion, granules or capsules. If it is an injection, it can be administered intravenously either alone or in a mixture with an ordinary replacement fluid such as glucose or amino acids, or else it can be administered by itself intramuscularly, intradermally, subcutaneously or intraperitoneally as necessary. In the case of a suppository, it can be administered in the rectum.

The dose of the medical preparation may be selected according to the administration method, the age and sex of the patient, the severity of the disease and other conditions, but normally 0.01 to 100 mg or preferably 0.1 to 50 mg per 1 kg of body weight can be administered per day in one or more administrations.

This dose is affected by various conditions, and in some cases a dose below the aforementioned range may be sufficient, while in others a dose above the aforementioned range may be necessary.

The compound [I] or a salt thereof of the present invention can be used in combination with various treatment or preventative agents for disease for which the compound [I] is thought to be effective. Such combined use may be by simultaneous administration, or else by separate administration, either continuously or with a suitable interval in between. Preparations that are administered simultaneously may be formulated separately or combination.

A pharmaceutical composition containing the compound [I] or a salt thereof of the present invention together with a pharmaceutically acceptable carrier and/or excipient is provided by one embodiment of the present invention.

Another embodiment provides a therapeutic, preventative and/or diagnostic agent for seizure in disease involving epileptic seizure or convulsive seizure (including multiple drug resistant seizure, refractory seizure, acute symptomatic seizure, febrile seizure and status epilepticus), containing the compound [I] or a salt thereof of the present invention together with a pharmaceutically acceptable carrier and/or excipient.

Yet another embodiment provides a therapeutic, preventative and/or diagnostic pharmaceutical composition for seizure in disease involving epileptic seizure or convulsive seizure (including multiple drug resistant seizure, refractory seizure, acute symptomatic seizure, febrile seizure and status epilepticus), containing the compound [I] or a salt thereof of the present invention together with a pharmaceutically acceptable carrier and/or excipient.

Yet another embodiment provides a method for treating, preventing and/or diagnosing seizure in disease involving epileptic seizure or convulsive seizure (including multiple drug resistant seizure, refractory seizure, acute symptomatic seizure, febrile seizure and status epilepticus), which comprises administering to a human in need thereof an effective amount of the compound [I] or a salt thereof of the present invention.

Yet another embodiment provides the compound [I] or a salt thereof of the present invention for use in the treatment, prevention and/or diagnosis of seizure in disease involving epileptic seizure or convulsive seizure (including multiple drug resistant seizure, refractory seizure, acute symptomatic seizure, febrile seizure and status epilepticus).

Yet another embodiment provides the use of the compound [I] or a salt thereof of the present invention in the manufacture of a drug for treating, preventing and/or diagnosing seizure in disease involving epileptic seizure or convulsive seizure (including multiple drug resistant seizure, refractory seizure, acute symptomatic seizure, febrile seizure and status epilepticus).

EXAMPLES

The present invention is explained in further detail below through the following Test Examples, Reference Examples and Examples, but these do not limit the present invention, and these may be changed to the extent that they do not deviate from the scope of the present invention.

The following abbreviations are used in this Description.

| Abbreviations | Words |
| --- | --- |
| DBU | 1,8-diazabicyclo [5.4.0]-7-undecene |
| DCC | dicyclohexylcarbodiimide |

| Abbreviations | Words |
|---|---|
| DCE | 1,2-dichloroethane |
| DCM | dichloromethane |
| DEAD | diethylazodicarboxylate |
| DHP | 3,4-dihydro-2H-pyran |
| DIBAL | diisobutylaluminum hydride |
| DIBOC | di-t-butyl dicarbonate |
| DIPEA | diisopropylethylamine |
| DMA | N,N-dimethylacetamide |
| DMAP | 4-(dimethylamino) pyridine |
| DME | dimethoxyethane |
| DMF | N,N-dimethylformamide |
| DMSO | dimethyl sulfoxide |
| DPPA | diphenylphosphoryl azide |
| $Et_2O$ | diethyl ether |
| EtOH | ethanol |
| HCl | hydrochloric acid |
| Hexane | n-hexane |
| HOBt | 1-hydroxybenzotriazole |
| IPA | 2-propanol |
| IPE | diisopropyl ether |
| $K_2CO_3$ | potassium carbonate |
| $K_3PO_4$ | tripotassium phosphate |
| $KHCO_3$ | potassium bicarbonate |
| KOH | potassium hydroxide |
| KOtBu | potassium t-butoxide |
| LAH | lithium aluminum hydride |
| LDA | lithium diisopropylamide |
| LHMDS | lithium hexamethyldisilazide |
| LIOH | lithium hydroxide |
| MeCN | acetonitrile |
| MEK | 2-butanone |
| MeOH | methanol |
| $NaBH_4$ | sodium borohydride |
| $Na_2CO_3$ | sodium carbonate |
| NaH | sodium hydride |
| $NaHCO_3$ | sodium hydrogen carbonate |
| NaOH | sodium hydroxide |
| NaOtBu | sodium t-butoxide |
| NBS | N-bromosuccinimide |
| NCS | N-chlorosuccinimide |
| NMP | N-methylpyrrolidone |
| $Pd_2$ (dba) = | tris (dibenzylideneacetone) dipalladium (0) |
| $PdCl_2$ (dppf) DCM | [1,1'-bis (diphenylphosphino) ferrocene] palladium (II) dichloride dichloromethane adduct |
| Pd $(OAc)_2$ | palladium (II) acetate |
| Pd $(PPh_3)_4$ | tetrakis (triphenylphosphine) palladium (0) |
| Pd/C | palladium-carrying carbon |
| Pt/C | platinum-carrying carbon |
| PEG | polyethylene glycol |
| PPTS | pyridinium p-toluenesulfonate |
| TBAF | tetra-n-butylammonium fluoride |
| TCDI | 1,1'-thiocarbonyldiimidazole |
| TEA | triethylamine |
| TFA | trifluoroacetic acid |
| THF | tetrahydrofuran |
| TPP | triphenylphosphine |
| WSC | 3-ethyl-1-(3-dimethylaminopropyl) carbodiimide |
| ZCl | benzyl chloroformate |
| XPhos Pd G3 | (2-dicyclohexylphosphino-2',4',6'-triisopropyl-1,1'-biphenyl) [2-(2'-amino-1,1'-biphenyl)]palladium (II) methanesulfonate |

In the examples below, "room temperature" normally indicates from about 10° C. to about 35° C. The ratios indicated for mixed solvents are volume ratios unless otherwise specified. Percentages indicate weight % unless otherwise specified.

The $^1$HNMR (proton nuclear magnetic resonance spectrum) was measured by Fourier-transform type NMR (either of Bruker AVANCE III 400 (400 MHZ) and Bruker AVANCE III HD (500 MHZ)).

In silica gel column chromatography, when denoted as basic, aminopropylsilane-bonded silica gel was used.

The absolute configuration of the compound was determined by known X-ray crystal structure analysis methods (for example, Shigeru Oba and Shigenobu Yano, "Basic Course for Chemists 12, X-ray Crystal Structure Analysis" (First Edition, 1999)), or estimated from empirical rules of Shi asymmetric epoxidation (Waldemar Adam, Rainer T. Fell, Chantu R. Saha-Moller and Cong-Gui Zhao: Tetrahedron: Asymmetry 1998, 9, 397-401. Yuanming Zhu, Yong Tu, Hongwu Yu, Yian Shi: Tetrahedron Lett. 1988, 29, 2437-2440).

REFERENCE EXAMPLES

Reference Example 1

Synthesis of 5-Bromo-2-Phenoxypyrimidine

5-Bromo-2-chloropyrimidine (25.0 g) was added to a suspension containing phenol (13.6 mL), $K_2CO_3$ (26.8 g), and DMF (250 mL), and the mixture was stirred at room temperature overnight. Water was added to the reaction solution, and the generated crystals were then collected by filtration and washed with water to obtain the object compound (27.7 g).

Reference Example 2

Synthesis of 2-Phenoxy-5-(4,4,5,5-Tetramethyl-1,3,2-Dioxaborolan-2-Yl)Pyrimidine A mixture containing 5-bromo-2-phenoxypyrimidine (1.00 g), (BPin)$_2$ (1.315 g), PdCl$_2$ (dppf) DCM (0.163 g), AcOK (0.782 g), and 1,4-dioxane (10 mL) was heated to reflux under a nitrogen atmosphere for 10 hours. Water and AcOEt were added to the reaction solution and the mixture was filtered through Celite. The organic layer was washed with water and brine, and dried with anhydrous sodium sulfate, and then concentrated. The residue was suspended in IPE, insoluble matter were filtered off, the filtrate was concentrated, and the obtained solid was washed with Hexane to obtain the object compound (646 mg).

Reference Example 18

Synthesis of 3-Methoxy-6-(2-(Methylthio)Pyrimidin-5-Yl)Pyridazine

A mixture containing 3-chloro-6-methoxypyridazine (206.3 mg), 2-(methylthio)pyrimidinyl-5-boronic acid pinacol ester (425.4 mg), K$_3$PO$_4$ (663.4 mg), PdCl$_2$ (dppf) DCM (48.6 mg), 1,4-dioxane (20 mL), and water (2 mL) was heated to reflux under a nitrogen atmosphere for 1.5 hours. The reaction solution was concentrated, and the residue was purified through silica gel chromatography (Hexane/AcOEt) to obtain the object compound (242.6 mg).

Reference Example 19

Synthesis of 3-Methoxy-6-(2-(Methylsulfonyl)Pyrimidin-5-Yl)Pyridazine

A mixture containing 3-methoxy-6-(2-(methylthio)pyrimidin-5-yl)pyridazine (242.6 mg), water content 77% m-CPBA (627.9 mg), and DCM (20 mL) was stirred at 0° C. for 1 hour, and additionally stirred at room temperature overnight. The reaction solution was poured into ice and a saturated NaHCO$_3$ aqueous solution, and the product was extracted with DCM. The organic layer was dried with anhydrous sodium sulfate and then concentrated. The residue was purified through silica gel chromatography (Hexane/AcOEt) to obtain the object compound (166.7 mg).

Reference Example 21

Synthesis of 5-(2-(Methylthio)Pyrimidin-5-Yl)Pyridin-2-Amine

A mixture containing 2-(methylthio)-5-(4,4,5,5-tetramethyl-1,3,2-dioxaborolan-2-yl)pyrimidine (1.96 g), 2-amino-5-bromopyridine (1.037 g), $K_3PO_4$ (3.86 g), $PdCl_2$ (dppf) DCM (273.3 mg), 1,4-dioxane (30 mL), and water (3 mL) was heated to reflux under a nitrogen atmosphere for 6 hours. Water was added to the reaction solution, and the product was then extracted with AcOEt. The organic layer was dried with anhydrous sodium sulfate and then concentrated. The residue was purified through basic silica gel chromatography (Hexane/AcOEt) to obtain the object compound (1.175 g).

Reference Example 22

Synthesis of 5-(2-(Methylsulfinyl)Pyrimidin-5-Yl)Pyridin-2-Amine

A mixture containing 5-(2-(methylthio)pyrimidin-5-yl)pyridin-2-amine (1.175 g), Oxone (registered trademark) (2.43 g), THF (30 mL), and water (10 mL) was stirred under a nitrogen atmosphere at 0° C. for 10 minutes and then stirred at room temperature for 2.75 hours. The reaction solution was poured into ice and a saturated $NaHCO_3$ aqueous solution, and the product was extracted with DCM. The organic layer was dried with anhydrous sodium sulfate and then concentrated. The residue was purified through silica gel chromatography (AcOEt, AcOEt/MeOH) to obtain the object compound (462 mg).

Reference Example 23

Synthesis of 5-Bromo-2-(Dodecylthio)Pyrimidine

A mixture containing 5-bromo-2-chloropyrimidine (2.30 g), 1-dodecanethiol (3.2 mL), $K_2CO_3$ (2.57 g), and DMF (20 mL) was stirred at room temperature overnight. Water was added thereto, and the product was extracted with AcOEt. The organic layer was washed with water and dried with anhydrous sodium sulfate and then concentrated. The residue was purified through silica gel chromatography (Hexane/AcOEt) to obtain the object compound (3.56 g).

Reference Example 24

Synthesis of 5-(2-(Dodecylthio)Pyrimidin-5-Yl)Pyridin-2-Amine

A mixture containing 5-bromo-2-(dodecylthio)pyrimidine (1.008 g), 2-amino-5-(4,4,5,5-tetramethyl-1,3,2-dioxaborolan-2-yl)pyridine (811.6 mg), $K_3PO_4$ (1.82 g), $PdCl_2$ (dppf) DCM (107.7 mg), 1,4-dioxane (20 mL), and water (2 mL) was heated to reflux under a nitrogen atmosphere for 2.25 hours. Water was added to the reaction solution, and the product was then extracted with AcOEt. The organic layer was dried with anhydrous sodium sulfate and then concentrated. The residue was purified through silica gel chromatography (Hexane/AcOEt) to obtain the object compound (1.01 g).

Reference Example 25

Synthesis of 5-(2-(Dodecylsulfinyl)Pyrimidin-5-Yl)Pyridin-2-Amine

A mixture containing 5-(2-(dodecylthio)pyrimidin-5-yl)pyridin-2-amine (1.010 g), Oxone (registered trademark) (1.97 g), THF (40 mL), and water (10 mL) was stirred at 0° C. for 25 minutes, and then stirred at room temperature overnight. The reaction solution was poured into a solution mixture containing ice, a saturated $NaHCO_3$ aqueous solution, and DCM and extracted with DCM. The organic layer was dried with anhydrous sodium sulfate and then concentrated. The residue was purified through silica gel chromatography (Hexane/AcOEt) to obtain the object compound (163 mg).

Reference Example 26

Synthesis of 3-(Benzyloxy)-6-(2-Phenoxypyrimidin-5-Yl)Pyridazine

A mixture containing 5-bromo-2-phenoxypyrimidine (2.96 g), $(BPin)_2$ (3.68 g), $PdCl_2$ (dppf) DCM (0.370 g), AcOK (1.78 g), and 1,4-dioxane (20 mL) was heated to reflux under a nitrogen atmosphere for 3 hours. 3-(Benzyloxy)-6-chloropyridazine (2.00 g), $PdCl_2$ (dppf) DCM (0.370 g), $K_3PO_4$ (3.85 g), and water (5 mL) were added to the reaction solution and heated to reflux for 2 hours. Water and AcOEt were added to the reaction solution and the mixture was filtered through Celite. The organic layer was washed with water and brine, and dried with anhydrous sodium sulfate and then concentrated. The residue was purified through silica gel column chromatography (DCM/AcOEt), and the obtained solid was then washed with AcOEt to obtain the object compound (2.54 g).

Reference Example 35

Synthesis of 4-(2-Phenoxypyrimidin-5-Yl)-2-(Tetrahydro-2H-Pyran-2-Yl)Pyridazin-3 (2H)-One A mixture containing 2-phenoxy-5-(4,4,5,5-tetramethyl-1,3,2-dioxaborolan-2-yl)pyrimidine (1.496 g), 4-bromo-2-(tetrahydro-2H-pyran-2-yl)pyridazin-3 (2H)-one (1.00 g), $PdCl_2$ (dppf) DCM (0.063 g), $K_3PO_4$ (1.229 g), 1,4-dioxane (10 mL), and water (3 mL) was stirred at 100° C. overnight. Water was added to the reaction solution and the product was extracted with AcOEt. The organic layer was dried with anhydrous sodium sulfate and then concentrated. The residue was purified through silica gel column chromatography (Hexane/AcOEt) and the obtained solid was then washed with EtOH to obtain the object compound (1.087 g).

Reference Example 38

Synthesis of 5-Bromo-1-Triisopropylsilyl-1H-Pyrazolo[3,4-b]Pyridine

60% NaH (0.933 g) was added to a DMF (20 mL) solution containing 5-bromo-1H-pyrazolo[3,4-b]pyridine (4.20 g) at 0° C. while stirring. After 20 minutes, chlorotriisopropylsilane (4.99 mL) was added thereto and the mixture was stirred for 30 minutes. The reaction solution was poured into ice water, and the precipitated solid was collected by filtration. The solid was dissolved in AcOEt and dried with anhydrous magnesium sulfate and then concentrated. The residue was purified through silica gel column chromatography (Hexane/AcOEt) to obtain the object compound (6.70 g).

Reference Example 39

Synthesis of 4-Methoxy-2-Phenoxy-5-(4,4,5,5-Tetramethyl-1,3,2-Dioxaborolan-2-Yl)Pyrimidine A solution mixture containing 5-bromo-4-methoxy-2-phenoxypyrimidine (15.00 g), (BPin)$_2$ (14.9 g), AcOK (10.5 g), PdCl$_2$ (dppf) DCM (2.18 g), and DMSO (60 mL) was stirred under a nitrogen atmosphere at 100° C. for 3 hours. The reaction solution was poured into ice water, and the product was extracted with AcOEt. The organic layer was washed with water and dried with anhydrous magnesium sulfate and then concentrated. The residue was purified through silica gel column chromatography (DCM/AcOEt) to obtain the object compound (9.61 g).

Reference Example 40

Synthesis of 2-(Dodecylthio)-5-(4,4,5,5-Tetramethyl-1,3,2-Dioxaborolan-2-Yl)Pyrimidine A mixture containing 5-bromo-2-(dodecylthio)pyrimidine (2.548 g), (BPin)$_2$ (2.17 g), AcOK (1.48 g), PdCl$_2$ (dppf) DCM (280.1 mg), and DMSO (20 mL) was stirred under a nitrogen atmosphere at 100° C. for 2 hours. The reaction solution was poured into ice water, and the product was extracted with AcOEt. The organic layer was washed with water and dried with anhydrous magnesium sulfate and then concentrated. The residue was purified through silica gel column chromatography (Hexane/AcOEt) to obtain the object compound (1.90 g).

Reference Example 41

Synthesis of 6-(2-(Dodecylthio)Pyrimidin-5-Yl) Imidazo[1,2-a]Pyridine

A mixture containing 2-(dodecylthio)-5-(4,4,5,5-tetramethyl-1,3,2-dioxaborolan-2-yl)pyrimidine (3.00 g), 6-bromoimidazo (1,2-a)pyridine (1.53 g), PdCl$_2$ (dppf) DCM (0.301 g), K$_3$PO$_4$ (3.13 g), 1,4-dioxane (20 mL), and water (10 mL) was stirred at 95° C. for 1 hour. The reaction solution was poured into ice water, and the product was extracted with AcOEt. The organic layer was washed with water and dried with anhydrous magnesium sulfate and then concentrated. The residue was purified through silica gel column chromatography (DCM/AcOEt) to obtain the object compound (2.05 g).

Reference Example 42

Synthesis of 6-(2-(Dodecylsulfonyl)Pyrimidin-5-Yl) Imidazo[1,2-a]Pyridine

A mixture containing 6-(2-(dodecylthio)pyrimidin-5-yl) imidazo[1,2-a]pyridine (2.00 g), Oxone (registered trademark) (7.75 g), THF (40 mL), and water (20 mL) was stirred at room temperature for 5 hours. The reaction solution was poured into ice water, and the product was extracted with AcOEt. The organic layer was washed with water and dried with anhydrous magnesium sulfate and then concentrated. The residue was purified through silica gel column chromatography (DCM/AcOEt) to obtain the object compound (910 mg).

Reference Example 43

Synthesis of 5-Nitro-2-Phenoxypyrimidine

A mixture containing phenol (6.61 mL), potassium carbonate (12.99 g), 2-chloro-5-nitropyrimidine (10 g), and DMF (80 mL) was stirred at room temperature overnight. Water was added to the reaction solution and the generated crystals were collected by filtration and washed with water to obtain the object compound (6.55 g).

Reference Example 44

Synthesis of 2-Phenoxypyrimidin-5-Amine

5-Nitro-2-phenoxypyrimidine (7.45 g) and hydrous 10% Pd/C (3 g) were suspended in EtOH (100 mL) and stirred under a hydrogen atmosphere at room temperature for 4 hours. The reaction solution was filtered through Celite, the filtrate was concentrated, and the obtained solid was washed with IPE to obtain the object compound (4.73 g).

Reference Example 45

Synthesis of 1-(3-Chloropropyl)-3-(2-Phenoxypyrimidin-5-Yl) Urea

A THF (10 mL) solution containing 2-phenoxypyrimidin-5-amine (1.00 g) was stirred at room temperature and 3-chloropropyl isocyanate (0.713 mL) was added thereto, and the mixture was stirred overnight. The precipitated solid was collected by filtration and washed with THF to obtain the object compound (756 mg).

Reference Example 46

Synthesis of 2-(3-Fluoromethoxyphenoxy)-5-Nitropyrimidine

A mixture containing m-fluorophenol (5.45 mL), potassium carbonate (10.40 g), 2-chloro-5-nitropyrimidine (8.00 g), and DMF (80 mL) was stirred at room temperature overnight. Water was added to the residue, and the product was extracted with AcOEt. The organic layer was washed with water and brine, dried with anhydrous sodium sulfate, and then concentrated to obtain the object compound (8.63 g).

Reference Example 47

Synthesis of 2-(3-Fluorophenoxy)Pyrimidin-5-Amine 2-(3-Fluoromethoxyphenoxy) nitropyrimidine (8.65 g) and 50% water-containing 10% Pd/C (3 g) were suspended in EtOH (100 mL) and stirred under a hydrogen atmosphere at room temperature for 16 hours. The reaction solution was filtered through Celite, and the filtrate was concentrated. The residue was purified through medium pressure column chromatography (DCM/AcOEt), and the obtained solid was then washed with hexane to obtain the object compound (3.77 g).

Reference Example 50

Synthesis of 2-Phenoxy-5-(4-(Triisopropylsilyloxy) Piperidin-1-Yl)Pyrimidine

A solution mixture containing 5-bromo-2-phenoxypyrimidine (400 mg), 4-(triisopropylsilyloxy) piperidine (451 mg), Pd(OAc)$_2$ (17.9 mg), tBu$_3$P·HBF$_4$ (23.1 mg), NaOtBu (153 mg) and toluene (6 mL) was stirred under a nitrogen atmosphere at 100° C. for 3 hours. The reaction solution was filtered through Celite, and the filtrate was concentrated. The residue was purified through silica gel column chromatography (Hexane/AcOEt) to obtain the object compound (250 mg).

Reference Example 56

Synthesis of (R)-1-(2-Phenoxypyrimidin-5-Yl)-4-(Triisopropylsilyloxy) Piperidin-2-One A solution mixture containing 5-iodo-2-phenoxypyrimidine (500 mg), (R)-4-(triisopropylsilyloxy) piperidin-2-one (501 mg), copper iodide (I) (5.68 µl), trans-N,N'-dimethylcyclohexane-1,2-diamine (0.053 mL), K$_3$PO$_4$ (712 mg), and 1,4-dioxane (6 mL) was stirred under a nitrogen atmosphere at 95° C. for 3 hours. The reaction solution was filtered through Celite, and the filtrate was concentrated. The residue was purified through silica gel column chromatography (Hexane/AcOEt) to obtain the object compound (340 mg).

Reference Example 58

Synthesis of 1-Fluoro-3-(4-Nitrophenoxy)Benzene

A mixture containing m-fluorophenol (41.7 g), 4-fluoronitrobenzene (50.0 g), K$_2$CO$_3$ (63.7 g), and DMF (250 mL) was stirred at 80° C. for 6 hours. The reaction solution was poured into ice water, and precipitates were collected by filtration and washed with water to obtain the object compound (80.7 g).

Reference Example 59

Synthesis of 4-(3-Fluorophenoxy) Aniline

Zinc powder (50.5 g) was added to a mixture containing 1-fluoro-3-(4-nitrophenoxy)benzene (30 g), ammonium chloride (41.3 g), EtOH (225 mL), and water (75 mL) while stirring the mixture at room temperature, and additionally the mixture was stirred at 60° C. for 1 hour. The insoluble matter was filtered through Celite, the filtrate was concentrated, and the residue was then extracted with AcOEt. The organic layer was washed with water and dried with anhydrous magnesium sulfate and then concentrated. The residue was purified through silica gel column chromatography (Hexane/AcOEt) to obtain the object compound (26 g).

Reference Example 60

Synthesis of 1-(4-Bromophenyl)Dihydropyrimidine-2,4 (1H,3H)-Dione

A toluene (50 mL) solution containing 4-bromoaniline (7.66 g) and acrylic acid (3.05 mL) was stirred at 80° C. overnight. The reaction solution was concentrated, urea (5.35 g) and acetic acid (20 mL) were added thereto, and the mixture was heated to reflux for 3 hours. The precipitated solid was collected by filtration and washed with EtOH to obtain the object compound (5.44 g).

Reference Example 61

Synthesis of 1-(4-(4,4,5,5-Tetramethyl-1,3,2-Dioxaborolan-2-Yl)Phenyl)Dihydropyrimidine-2,4 (1H, 3H)-Dione A mixture containing 1-(4-bromophenyl)dihydropyrimidine-2,4 (1H,3H)-dione (2.78 g), (BPin)$_2$ (3.15 g), AcOK (3.04 g), PdCl$_2$ (dppf) DCM (0.422 g), and DMSO (30 mL) was stirred under an argon atmosphere at 100° C. for 5 hours. The reaction solution was poured into ice water and extracted with AcOEt. The organic layer was washed with water and dried with anhydrous magnesium sulfate and then concentrated. The residue was purified through silica gel column chromatography (DCM/MeOH) to obtain the object compound (0.82 g).

Reference Example 76

Synthesis of 1-[4-(3-Hydroxyphenoxy)Phenyl]Dihydropyrimidine-2,4 (1H,3H)-Dione

HBr (12.5 mL) was added to an AcOH (25 mL) solution containing 1-[4-(3-methoxyphenoxy)phenyl]dihydropyrimidine-2,4 (1H,3H)-dione (3.86 g) under ice-cooling, and the mixture was stirred for 3 hours. Water (100 mL) was added to the reaction solution, the mixture was stirred, and the precipitated crystals were collected by filtration. Washing with water and drying were performed, and purification through silica gel column chromatography (DCM/MeOH) was then performed, and the obtained solid was washed with MeOH to obtain the object compound (1.11 g).

Reference Example 77

Synthesis of 3-(3-Fluorophenoxy) Aniline

A mixture containing 3-fluoroiodobenzene (0.587 mL), 3-aminophenol (818 mg), K$_3$PO$_4$ (2.12 g), picolinic acid (123 mg), copper iodide (I) (95 mg), and DMSO (15 mL) was stirred under a nitrogen atmosphere at 90° C. for 24 hours. Water was added to the reaction solution, and the product was then extracted with AcOEt. The organic layer was washed with water and dried with anhydrous magnesium sulfate and then concentrated. The residue was purified through silica gel column chromatography (Hexane/AcOEt) to obtain the object compound (865 mg).

Reference Example 83

Synthesis of 5-Nitro-2-Phenoxypyridine

Sodium phenoxide (12.3 g) was added to a DMF (80 mL) solution containing 2-chloro-5-nitropyridine (16.0 g) while ice-cooling and stirring the solution and stirring was continued at room temperature overnight. The reaction solution was poured into ice water, and the precipitated crystals were collected by filtration and washed with water to obtain the object compound (21.1 g).

Reference Example 84

Synthesis of 6-Phenoxypyridin-3-Amine

A mixture containing 5-nitro-2-phenoxypyridine (21 g), 10% Pd/C (2 g), and EtOH (200 mL) was stirred under a hydrogen atmosphere at room temperature for 3 hours. The reaction solution was filtered through Celite, and the filtrate was concentrated. The residue was purified through silica gel column chromatography (Hexane/AcOEt) to obtain the object compound (15 g).

Reference Example 111

Synthesis of
1-(6-Chloropyridazine-3-Yl)Pyrimidine-2,4
(1H,3H)-Dione

A mixture containing 3,6-dichloropyridazine (10.00 g), uracil (8.28 g), and DMSO (100 mL) was stirred at 70° C. overnight. Water was added to the reaction solution, and the generated solid was then collected by filtration, and washed with water and EtOH to obtain the object compound (9.51 g).

The compounds of Reference Examples 3 to 17, 20, 27 to 34, 36, 37, 48, 49, 51 to 55, 57, 62 to 75, 78 to 82, 85 to 95 and 97 to 110 were manufactured in the same manner as in Reference Examples 1, 2, 18, 19, 21 to 26, 35, 38 to 47, 50, 56, 58 to 61, 76, 77, 83, 84 and 111. Structural formulae and physicochemical data of the compounds of Reference Examples 1 to 111 are shown in Tables 1-1 to 1-11.

TABLE 1-1

| REX | STR | RProp | DATA |
|---|---|---|---|
| 1 | | 1 | NMR2; 7.14-7.23(2H, m), 7.24-7.33(1H, m), 7.39-7.49(2H, m), 8.57(2H, s). |
| 2 | | 2 | NMR2; 1.34(12H, s), 7.17-7.22(2H, m), 7.23-7.29(1H, m), 7.39-7.47(2H, m), 8.83(2H, s). |
| 3 | | 1 | NMR2; 7.15-7.32(4H, m), 8.57 (2H, s). |
| 4 | | 2 | NMR2; 1.34 (12H, s), 7.17-7.30(4H, m), 8.84(2H, s). |
| 5 | | 1 | NMR2; 6.90-7.04(3H, m), 7.39(1H, td, J = 8.3, 6.5 Hz), 8.58(2H, s). |
| 6 | | 2 | NMR2; 1.34(12H, s), 6.91-7.04(3H, m), 7.33-7.44(1H, m), 8.85(2H, s). |
| 7 | | 1 | NMR2; 7.06-7.20(4H, m), 6.57(2H, s). |

TABLE 1-1-continued
| REX | STR | RProp | DATA |
|---|---|---|---|
| 8 | 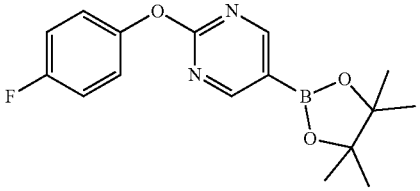 | 2 | NMR1; 1.31(12H, s), 7.23-7.33(4H, m), 8.75(2H, s). |
| 9 | 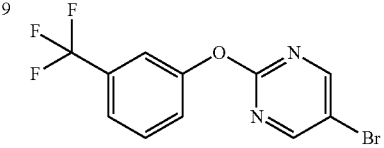 | 1 | NMR2; 7.35-7.41(1H, m), 7.47(1H, ddt, J = 2.2, 1.5, 0.7 Hz), 7.51-7.61(2H, m), 8.59(2H, s). |
| 10 | 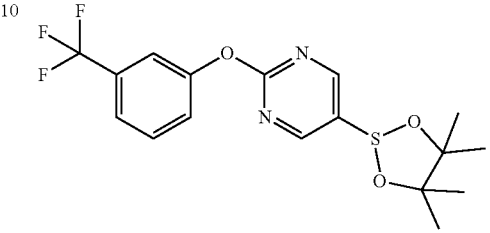 | 2 | NMR2; 1.35(12H, s), 7.34-7.48(2H, m), 7.48-7.60(2H, m), 8.85(2H, s). |
| 11 | 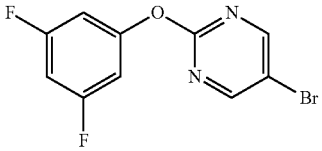 | 1 | NMR2; 6.69-6.83 (3H, m), 8.60(2H, s). |
| 12 | 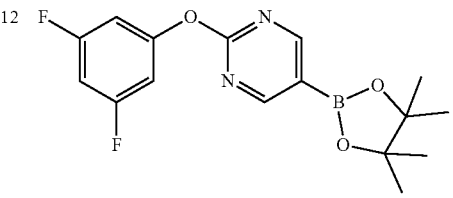 | 2 | NMR2; 1.35(12H, s), 6.68-6.82(3H, m), 8.86(2H, s). |
TABLE 1-2
| REX | STR | RProp | DATA |
|---|---|---|---|
| 13 | 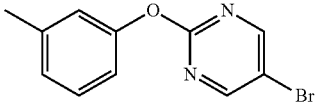 | 1 | NMR2; 2.39(3H, s), 6.93-7.02(2H, m), 7.03-7.13(1H, m), 7.26-7.37(1H, m), 8.56(2H, s). |
| 14 | 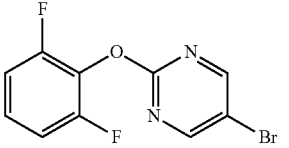 | 1 | NMR2; 6.97-7.09(2H, m), 7.15-7.28(1H, m), 8.58(2H, s). |

TABLE 1-2-continued

| REX | STR | RProp | DATA |
|---|---|---|---|
| 15 | | 2 | NMR2; 1.34(12H, s), 6.98-7.08(2H, m), 7.15-7.24(1H, m), 8.84(2H, s). |
| 16 | | 1 | NMR2; 7.06-7.19(3H, m), 7.45(1H, t, J = 8.2 Hz), 8.59(2H, s). |
| 17 | | 2 | NMR2; 1.35(12H, s), 7.08-7.20(3H, m), 7.44(1H, dt, J = 0.6, 8.1 Hz), 8.85(2H, s). |
| 18 | | 18 | NMR2; 2.64(3H, s), 4.21(3H, s), 7.11(1H, d, J = 9.2 Hz), 7.75(1H, d, J = 9.3 Hz), 9.14(2H, s). |
| 19 | | 19 | NMR2; 3.43(3H, s), 4.26(3H, s), 7.20(1H, d, J = 9.2 Hz), 7.89(1H, d, J = 9.3 Hz), 9.54 (2H, s). |
| 20 | | 18 | NMR2; 1.50(3H, t, J = 7.2 Hz), 4.58(2H, q, J = 7.2 Hz), 7.21-7.36(3H, m), 7.43-7.53(2H, m), 7.97(1H, d, J = 8.8 Hz), 8.30(1H, d, J = 8.8 Hz), 9.33(2H, s). |
| 21 | | 21 | NMR2; 2.61 (3H, s), 4.61(2H, s), 6.61(1H, dd, J = 8.5, 0.9 Hz), 7.60(1H, dd, J = 8.8, 2.5 Hz), 8.26(1H, dd, J = 2.5, 0.8 Hz), 8.67(2H, s). |
| 22 | | 22 | NMR1; 2.89(3H, s), 6.43(2H, s), 6.58(1H, dd, J = 8.7, 0.8 Hz), 7.91(1H, dd, J = 8.7, 2.5 Hz), 8.47(1H, dd, J = 2.6, 0.8 Hz), 9.24(2H, s). |

TABLE 1-2-continued
| REX | STR | RProp | DATA |
|---|---|---|---|
| 23 | 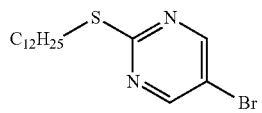 | 23 | NMR2; 0.84-0.92(3H, m), 1.20-1.39(18H, m), 1.44(2H, t, J = 7.4 Hz), 1.71(2H, ddd, J = 15.1, 8.0, 6.8 Hz), 3.08-3.15(2H, m), 8.54(2H, s). |
TABLE 1-3
| REX | STR | RProp | DATA |
|---|---|---|---|
| 24 | 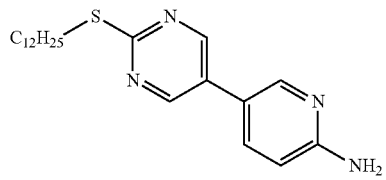 | 24 | NMR2; 0.84-0.92 (3H, m), 1.26 (15H, s), 1.40-1.55 (2H, m), 1.75 (2H, m), 3.13-3.22(2H, m), 4.60 (2H, s), 6.61(1H, dd, J = 5.5, 0.9 Hz), 7.60 (1H, dd, J = 8.5, 2.5 Hz), 8.26(1H, dd, J = 2.5, 0.8 Hz), 8.65(2H, s). |
| 25 | 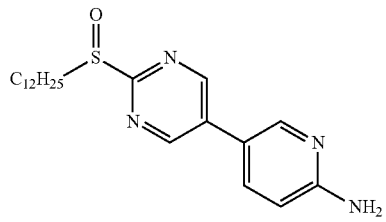 | 25 | NMR2; 0.88(3H, t, J = 7.0 Hz), 1.22-1.34(16H, m), 1.35-1.51(1H, m), 1.48(1H, s), 1.61-1.69(1H, m), 1.90-2.08 (1H, m), 3.09(1H, ddd, J = 13.1, 9.8, 5.2 Hz), 3.17 (1H, ddd, J = 13.1, 9.9, 6.2 Hz), 4.73(2H, s), 6.65(1H, dd, J = 8.6, 0.8 Hz), 7.69 (1H, dd, J = 8.6, 2.5 Hz), 5.36 (1H, dd, J = 2.6, 0.8 Hz), 8.98(2H, s). |
| 26 | 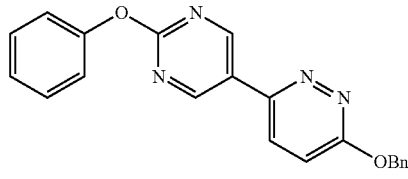 | 26 | NMR2; 5.64(2H, s), 7.15(1H, d, J = 9.2 Hz), 7.21-7.54(10H, m), 7.75(1H, d, J = 9.2 Hz), 9.17(2H, s). |
| 27 | 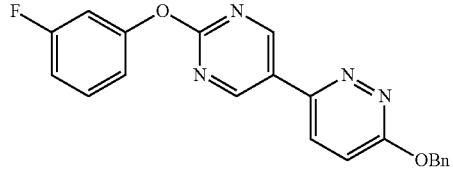 | 18 | NMR2; 5.65(2H, s), 6.96-7.10(3H, m), 7.16(1H, d, J = 9.2 Hz), 7.32-7.48(4H, m), 7.48-7.56(2H, m), 7.76(1H, d, J = 9.2 Hz), 9.18(2H, s). |
| 28 | 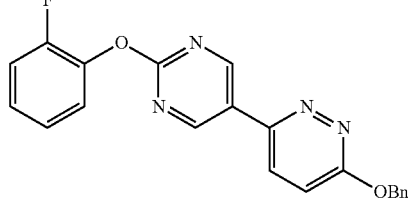 | 18 | NMR2; 5.64(2H, s), 7.16(1H, d, J = 9.2 Hz), 7.18-7.45(7H, m), 7.48-7.56(2H, m), 7.75(1H, d, J = 9.2 Hz), 9.17(2H, s). |
| 29 | 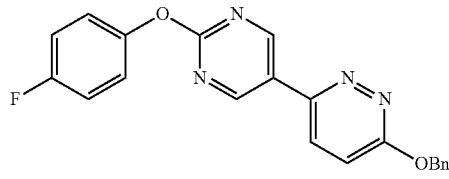 | 18 | NMR2; 5.64(2H, s), 7.09-7.27(5H, m), 7.32-7.46(3H, m), 7.48-7.56(2H, m), 7.75(1H, d, J = 9.2 Hz), 9.16(2H, s). |

TABLE 1-3-continued

| REX | STR | RProp | DATA |
|---|---|---|---|
| 30 | (3-trifluoromethylphenoxy-pyrimidinyl-pyridazinyl-OBn) | 18 | NMR2; 5.65(2H, s), 7.17(1H, d, J = 9.2 Hz), 7.33-7.62(9H, m), 7.77(1H, d, J = 9.2 Hz), 9.18(2H, s). |
| 31 | (2,6-difluorophenoxy-pyrimidinyl-pyridazinyl-OBn) | 18 | NMR2; 5.65(2H, s), 7.02-7.09(2H, m), 7.15(1H, d, J = 9.2 Hz), 7.19-7.28(1H, m), 7.34-7.45(3H, m), 7.50-7.55(2H, m), 7.76(1H, d, J = 9.2 Hz), 9.17(2H, s). |
| 32 | (3,5-difluorophenoxy-pyrimidinyl-pyridazinyl-OBn) | 18 | NMR2; 5.85(2H, s), 6.73-6.80(1H, m), 6.81-6.87(2H, m), 7.17(1H, d, J = 9.2 Hz), 7.34-7.45(3H, m), 7.50-7.55(2H, m), 7.77(1H, d, J = 9.2 Hz), 9.19(2H, s). |

TABLE 1-4

| REX | STR | RProp | DATA |
|---|---|---|---|
| 33 | (phenoxy-pyrimidinyl-pyridinyl-OBn) | 18 | NMR2; 5.43(2H, s), 6.93(1H, dd, J = 0.8, 8.6 Hz), 7.17-7.51 (10H, m), 7.73(1H, dd, J = 2.6, 8.6 Hz), 8.33(1H, dd, J = 0.8, 2.6 Hz), 8.70(2H, s). |
| 34 | (phenoxy-pyrimidinyl-methoxypyridinyl) | 18 | NMR2; 3.98(3H, s), 7.02(1H, dd, J = 5.0, 7.4 Hz), 7.17-7.33(3H, m), 7.40-7.51(2H, m), 7.61(1H, dd, J = 1.9, 7.4 Hz), 8.22(1H, dd, J = 1.9, 5.0 Hz), 8.76(2H, s). |
| 35 | (phenoxy-pyrimidinyl-pyridazinone-THP) | 35 | NMR2; 1.57-1.85(4H, m), 2.04-2.10(1H, m), 2.13-2.27(1H, m), 3.73-3.84(1H, m), 4.13-4.22(1H, m), 6.15(1H, dd, J = 2.2, 10.7 Hz), 7.18-7.34(4H, m), 7.41-7.51(2H, m), 7.96(1H, d, J = 4.1 Hz), 9.01(2H, s). |
| 36 | (3-fluorophenoxy-pyrimidinyl-pyridazinone-THP) | 18 | NMR2; 1.57-1.64(1H, m), 1.66-1.84(3H, m), 2.04-2.11(1H, m), 2.13-2.28(1H, m), 3.73-3.85(1H, m), 4.13-4.22(1H, m), 6.16(1H, dd, J = 2.2, 10.7 Hz), 6.94-7.08(3H, m), 7.31(1H, d, J = 4.1 Hz), 7.35-7.46(1H, m), 7.96(1H, d, J = 4.1 Hz), 9.02(2H, s). |

TABLE 1-4-continued

| REX | STR | RProp | DATA |
|---|---|---|---|
| 37 | | 18 | NMR2; 1.59-1.86(4H, m), 2.05(1H, d, J = 5.7 Hz), 2.13-2.27(1H, m), 3.73-3.84(1H, m), 4.13-4.22(1H, m), 6.15(1H, dd, J = 2.2, 10.7 Hz), 7.17-7.35(6H, m), 7.95(1H, d, J = 4.1 Hz), 9.01(2H, s). |
| 38 | | 38 | NMR2; 1.12(18H, d, J = 7.5 Hz), 1.91(3H, hept. J = 7.5 Hz), 8.16(2H, d, J = 2.2 Hz), 8.51(1H, d, J = 2.2 Hz). |
| 39 | | 39 | NMR2; 1.33(12H, s), 3.94(3H, s), 7.15-7.28(3H, m), 7.36-7.46(2H, m), 8.56(1H, s). |
| 40 | | 40 | NMR2; 0.84-0.92(3H, m), 1.23-1.36(28H, m), 1.40-1.48(2H, m), 1.66-1.78(2H, m), 3.11-3.21(2H, m), 8.75(2H, s). |
| 41 | | 41 | NMR2; 0.84-0.92(3H, m), 1.27(16H, d, J = 4.9 Hz), 1.42-1.66(2H, m), 1.70-1.83(2H, m), 3.15-3.24(2H, m), 7.32(1H, dd, J = 9.3, 1.8 Hz), 7.68-7.79(3H, m), 8.31 (1H, dd, J = 1.8, 1.0 Hz), 8.71(2H, s). |
| 42 | | 42 | NMR2; 0.88-0.92(3H, m), 1.25(16H, s), 1.47(2H, q, J = 7.4 Hz), 1.83-1.93(2H, m), 3.52-3.61(2H, m), 7.40(1H, dd, J = 9.3, 1.9 Hz), 7.74-7.80 (2H, m), 7.82-7.87 (1H, m), 8.45-8.51(1H, m), 9.14(2H, s). |

TABLE 1-5

| REX | STR | RProp | DATA |
|---|---|---|---|
| 43 | | 1 | NMR2; 7.17-7.24(2H, m), 7.31-7.39(1H, m), 7.45-7.53(2H, m), 9.33(2H, s). |

TABLE 1-5-continued
| REX | STR | RProp | DATA |
|---|---|---|---|
| 44 | 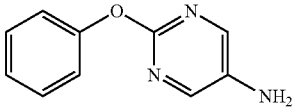 | 44 | NMR2; 3.50(2H, brs), 7.13-7.24(3H, m), 7.35-7.45(2H, m), 8.07(2H, s). |
| 45 | 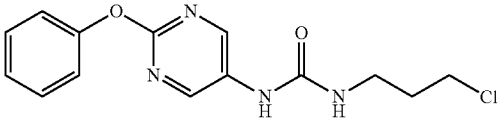 | 45 | NMR2; 2.05(2H, p, J = 6.5 Hz), 3.47(2H, q, J = 6.4 Hz), 3.60-3.68(2H, m), 4.74(1H, s), 6.10(1H, s), 7.15-7.27(3H, m), 7.35-7.47(2H, m), 8.60(2H, s). |
| 46 | 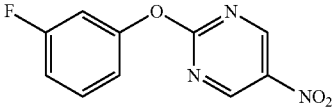 | 46 | NMR2; 6.93-7.12(3H, m), 7.61(1H, dt, J = 6.4 Hz, 8.3 Hz), 9.34(2H, s). |
| 47 | 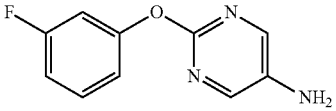 | 47 | NMR2; 3.66(2H, brs), 8.86-7.00(8H, m), 7.30-7.39(1H, m), 8.08(2H, s). |
| 48 | 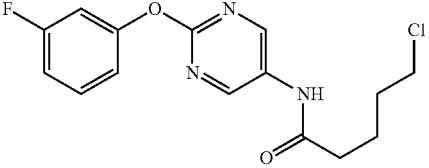 | 10 | NMR2; 1.82-1.98(4H, m), 2.47(2H, t, J = 8.9 Hz), 3.55-3.63(2H, m), 6.90-7.03(3H, m), 7.16(1H, s), 7.32-7.43(1H, m), 8.76(2H, s). |
| 49 | 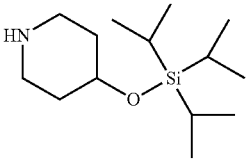 | 11 | NMR2; 1.06(21H, d, J = 2.0 Hz), 1.37-1.63(3H, m), 1.76-1.87(2H, m), 2.61(2H, ddd, J = 12.5, 9.3, 3.1 Hz), 3.02-3.13(2H, m), 3.79-3.90(1H, m). |
| 50 | 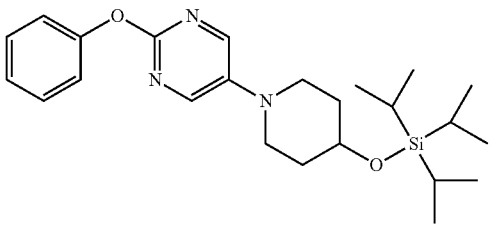 | 50 | NMR2; 1.07(21H, d, J = 3.5 Hz), 1.70-1.80(2H, m), 1.93(2H, ddt, J = 12.0, 7.6, 3.5 Hz), 3.04(2H, ddd, J = 11.6, 7.1, 3.7 Hz), 3.36(2H, ddd, J = 11.9, 8.3, 3.5 Hz), 3.98-4.08(1H, m), 7.14-7.25(3H, m), 7.35-7.45(2H, m), 8.23(2H, s). |
| 51 | 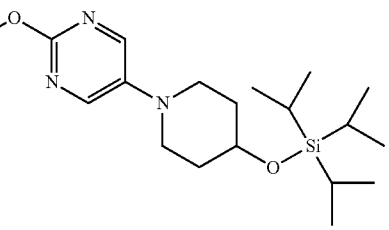 | 50 | NMR2; 1.07(21H, d, J = 3.6 Hz), 1.71-1.83(2H, m), 1.87-1.99(2H, m), 3.07(2H, ddd, J = 11.5, 7.0, 3.8 Hz), 3.35(2H, ddd, J = 11.9, 8.3, 3.5 Hz), 4.04(1H, tt, J = 6.7, 3.3 Hz), 6.86-7.01(3H, m), 7.29-7.40 (1H, m), 8.24(2H, s). |
| 52 | 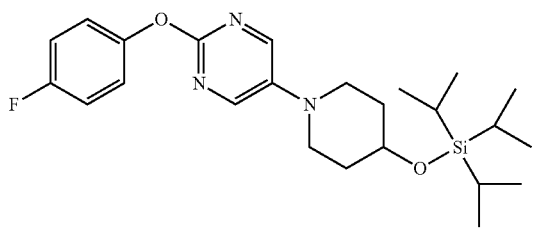 | 50 | NMR2; 1.00-1.15(21H, m), 1.70-1.83(2H, m), 1.86-1.99(2H, m), 3.00-3.09(2H, m), 3.29-3.40(2H, m), 3.98-4.08(1H, m), 7.02-7.19(4H, m), 8.22(2H, s). |

TABLE 1-5-continued
| REX | STR | RProp | DATA |
|---|---|---|---|
| 53 | 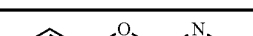 | 1 | NMR2; 7.14-7.22(2H, m), 7.23-7.34(1H, m), 7.39-7.49(2H, m), 8.88(2H, s). |
| 54 | 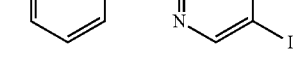 | 1 | NMR2; 6.90-7.04(3H, m), 7.29-7.44(1H, m), 8.70(2H, s). |
TABLE 1-6
| REX | STR | RProp | DATA |
|---|---|---|---|
| 55 | 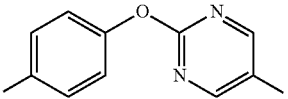 | 1 | NMR2; 7.05-7.24(4H, m), 8.68(2H, s). |
| 56 | 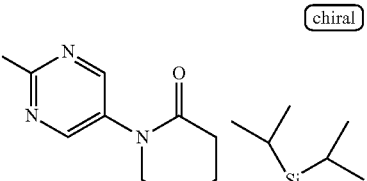 | 56 chiral | NMR2; 1.02-1.18(21H, m), 2.08(2H, dddd, J = 15.4, 10.2, 5.7, 2.2 Hz), 2.61-2.71(1H, m), 2.75(1H, dd, J = 17.4, 3.9 Hz), 3.48-3.58(1H, m), 3.91-4.02(1H, m), 4.46(1H, ddd, J = 6.8, 5.3, 3.3 Hz), 7.16-7.31(3H, m), 7.39-7.49(2H, m), 8.50(2H, s). |
| 57 | 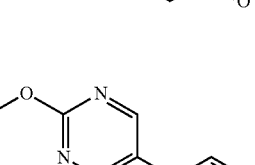 | 18 | NMR2; 7.20-7.28(2H, m), 7.26-7.36(1H, m), 7.42-7.53(2H, m), 7.66-7.74(2H, m), 8.32-6.41 (2H, m), 8.81(2H, s). |
TABLE 1-7
| REX | STR | RProp | DATA |
|---|---|---|---|
| 58 | 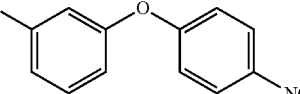 | 58 | NMR2; 6.82(1H, dt, J = 9.5, 2.3 Hz), 6.85-6.90(1H, m), 6.96(1H, tdd, J = 8.3, 2.5, 0.9 Hz), 7.01-7.10(2H, m), 7.39(1H, td, J = 8.3, 6.5 Hz), 8.19-8.28(2H, m) |
| 59 | 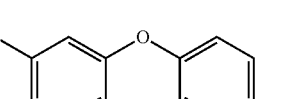 | 59 | NMR2; 3.61(2H, s), 6.61(1H, dt, J = 10.6, 2.4 Hz), 6.64-6.76(4H, m), 6.83-6.94(2H, m), 7.20(2H, td, J = 8.3, 6.7 Hz) |
| 60 | 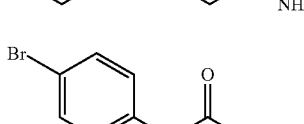 | 60 | NMR1; 2.71(2H, t, J = 6.7 Hz), 3.79(2H, t, J = 6.7 Hz), 7.28-7.32(2H, m), 7.56-7.60(2H, m), 10.43(1H, s). |

TABLE 1-7-continued

| REX | STR | RProp | DATA |
|---|---|---|---|
| 61 | | 61 | NMR1; 1.29(12H, s), 2.71(2H, t, J = 6.6 Hz), 3.82(2H, t, J = 6.6 Hz), 7.35(2H, d, J = 8.4 Hz), 7.68(2H, d, J = 8.4 Hz), 10.41(1H, s). |
| 62 | | 58 | NMR2; 6.96-6.99(1H, m), 7.01-7.14(4H, m), 7.45(1H, t, J = 8.3 Hz), 8.20-8.29(2H, m) |
| 63 | | 59 | NMR2; 3.83(2H, brs), 6.66-6.73(2H, m), 6.75-6.79(1H, m), 6.81-6.92(4H, m), 7.26(1H, t, J = 8.3 Hz) |
| 64 | | 58 | NMR2; 7.02-7.10(2H, m), 7.24-7.31(1H, m), 7.34-7.38(1H, m), 7.48-7.60(2H, m), 6.21-6.28(2H, m) |
| 65 | | 59 | NMR2; 3.63(2H, s), 6.66-6.74(2H, m), 6.83-6.92(2H, m), 7.05-7.11(1H, m), 7.12-7.18(1H, m), 7.21-7.32(1H, m), 7.38-7.42(1H, m) |
| 66 | | 58 | NMR2; 6.98-7.05(2H, m), 7.15-7.31(4H, m), 8.18-8.24(2H, m). |
| 67 | | 59 | NMR2; 3.57(2H, br), 6.64-6.71(2H, m), 6.83-6.88(2H, m), 6.88-6.95(1H, m), 6.96-7.05(2H, m), 7.10-7.17(1H, m). |
| 68 | | 58 | NMR2; 6.95-7.02(2H, m), 7.03-7.17(4H, m), 8.16-8.25(2H, m). |
| 69 | | 59 | NMR2; 3.51(2H, br), 6.66-6.70(2H, m), 6.80-6.92(4H, m), 6.93-7.00(2H, m). |

TABLE 1-8
| REX | STR | RProp | DATA |
|---|---|---|---|
| 70 | 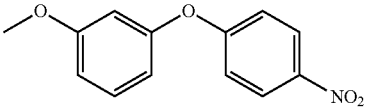 | 58 | NMR2; 3.81(3H, s), 6.64(1H, dd, J = 2.3, 2.3 Hz), 6.67(1H, ddd, J = 0.8, 2.2, 8.0 Hz), 5.80(1H, ddd, J = 0.8, 2.4, 8.3 Hz), 7.00-7.06(2H, m), 7.33(1H, dd, J = 8.2, 8.2 Hz), 8.18-8.23(2H, m). |
| 71 | 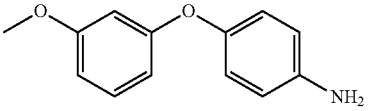 | 59 | NMR2; 3.58(2H, br), 3.75(3H, s), 6.49-6.51(2H, m), 6.55-6.58(1H, m), 6.63-6.59(2H, m), 6.85-6.89(2H, m), 7.14-7.18(1H, m). |
| 72 | 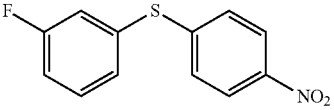 | 58 | NMR2; 7.11-7.18(1H, m), 7.19-7.23(1H, m), 7.23-7.28(2H, m), 7.28-7.33(1H, m), 7.38-7.46(1H, m), 8.08-8.24(2H, m). |
| 73 | 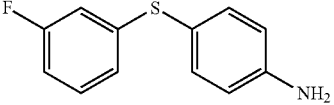 | 59 | NMR2; 3.87(2H, br), 6.67-6.79(4H, m), 6.85-6.90(1H, m), 7.12-7.19(1H, m), 7.30-7.35(2H, m). |
| 74 | 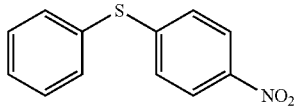 | 58 | NMR2; 7.15-7.21(2H, m), 7.43-7.50(3H, m), 7.52-7.58(2H, m), 8.04-8.09(2H, m). |
| 75 | 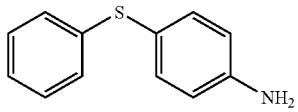 | 59 | NMR1; 5.52(2H, s), 6.59-6.64(2H, m), 6.98-7.03(2H, m), 7.06-7.12(1H, m), 7.16-7.20(2H, m), 7.20-7.27(2H, m). |
| 76 | 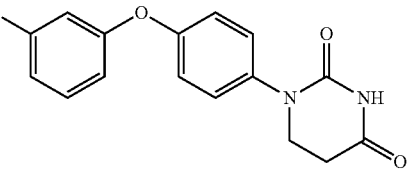 | 76 | NMR1; 2.71(2H, t, J = 6.7 Hz), 3.77(2H, t, J = 6.7 Hz), 6.37(1H, dd, J = 2.3, 2.3 Hz), 6.44(1H, ddd, J = 0.8, 2.3, 8.1 Hz), 6.53(1H, ddd, J = 0.8, 2.2, 8.1 Hz), 7.00-7.06(2H, m), 7.16(1H, dd, J = 8.1, 8.1 Hz), 7.31-7.36(2H, m), 9.61(1H, s), 10.37(1H, s) |
| 77 | 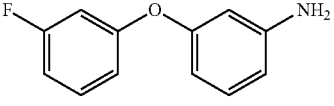 | 77 | NMR2; 3.72(2H, br), 6.35(1H, dd, J = 2.2, 2.2 Hz), 6.41(1H, ddd, J = 0.8, 2.3, 8.1 Hz), 6.48(1H, ddd, J = 0.8, 2.2, 8.0 Hz), 6.71(1H, ddd, J = 2.4, 2.4, 6.9 Hz), 6.74-6.82(2H, m), 7.12(1H, dd, J = 8.0, 8.0 Hz), 7.21-7.29(1H, m). |
| 78 | 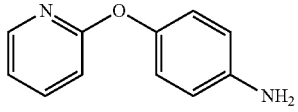 | 77 | NMR2; 3.61(2H, br), 8.88-5.74(2H, m), 6.56(1H, ddd, J = 0.8, 0.8, 6.5 Hz), 6.91-6.97(3H, m), 7.63(1H, ddd, J = 1.8, 7.2, 8.3 Hz), 8.18(1H, ddd, J = 0.8, 2.0, 5.0 Hz). |
| 79 | 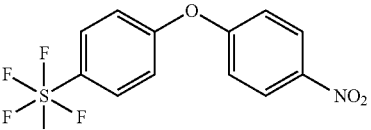 | 58 | NMR2; 7.09-7.17(4H, m), 7.79-7.85(2H, m), 8.24-8.30(2H, m). |
| 80 | 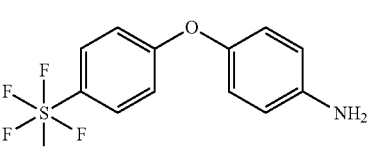 | 59 | NMR2; 3.68(2H, br), 6.68-6.74(2H, m), 6.85-6.94(4H, m), 7.62-7.67(2H, m). |

TABLE 1-8-continued
| REX | STR | RProp | DATA |
|---|---|---|---|
| 81 | 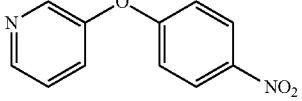 | 58 | NMR2; 7.03-7.09(2H, m), 7.36-7.47(2H, m), 8.21-8.28(2H, m), 8.49(1H, d, J = 2.5 Hz), 6.53(1H, dd, J = 1.5, 4.5 Hz). |
TABLE 1-9
| REX | STR | RProp | DATA |
|---|---|---|---|
| 82 | 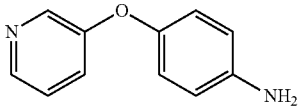 | 59 | NMR2; 3.64(2H, br), 6.67-6.72(2H, m), 6.85-6.91(2H, m), 7.20-7.23(2H, m), 8.28-8.31(1H, m), 8.35-8.38(1H, m). |
| 83 | 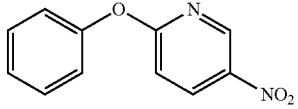 | 83 | NMR2; 7.03(1H, dd, J = 9.0, 0.6 Hz), 7.13-7.20(2H, m), 7.27-7.34(1H, m), 7.42-7.50(2H, m), 8.48(1H, dd, J = 9.0, 2.8 Hz), 9.03-9.07(1H, m). |
| 84 | 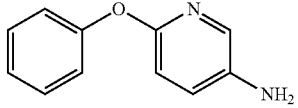 | 84 | NMR2; 3.53(2H, brs), 6.72-6.79(1H, m), 7.01-7.16(4H, m), 7.29-7.39(2H, m), 7.69-7.75(1H, m). |
| 85 | 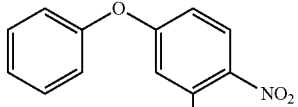 | 58 | NMR2; 2.60(3H, s), 6.80-6.85(2H, m), 7.03-7.12(2H, m), 7.20-7.29(1H, m), 7.37-7.48(2H, m), 8.01-8.09(1H, m). |
| 86 | 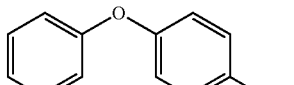 | 59 | NMR2; 2.15(3H, s), 3.50(2H, brs), 6.65(1H, d, J = 8.4 Hz), 6.71-6.82(2H, m), 686-6.97(2H, m), 7.00(1H, tt, J = 7.3, 1.1 Hz), 7.22-7.32(2H, m). |
| 87 | 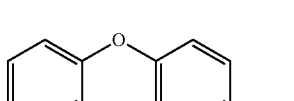 | 58 | NMR2; 3.90(3H, s), 6.49(1H, dd, J = 9.1, 2.4 Hz), 6.66(1H, d, J = 2.4 Hz), 7.05-7.13(2H, m), 7.20-7.38(1H, m), 7.38-7.49(2H, m), 7.94(1H, d, J = 9.1 Hz). |
| 88 | 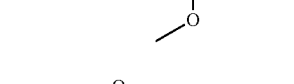 | 59 | NMR2; 3.68(2H, s), 3.79(3H, s), 6.46-6.54(1H, m), 6.54-6.60(1H, m), 6.67(1H, d, J = 8.3 Hz), 6.89-6.97(2H, m), 6.97-7.05(1H, m), 7.23-7.33(2H, m). |
| 89 | 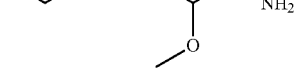 | 58 | NMR2; 2.87(3H, d, J = 0.8 Hz), 6.80-6.86(1H, m), 7.10-7.18(2H, m), 7.25-7.33(1H, m), 7.39-7.51(2H, m), 8.89(1H, s). |

TABLE 1-9-continued

| REX | STR | RProp | DATA |
|---|---|---|---|
| 90 | | 59 | NMR2; 2.15-2.21(3H, m), 3.44(2H, s), 5.66(1H, s), 6.99-7.07(2H, m), 7.07-7.14(1H, m), 7.28-7.38(2H, m), 7.56(1H, d, J = 1.6 Hz). |
| 91 | | 58 | NMR2; 2.76(3H, s), 6.78(1H, dd, J = 8.9, 0.7 Hz), 7.12-7.20(2H, m), 7.23-7.32(1H, m), 7.40-7.48(2H, m), 8.36(1H, d, J = 8.9 Hz) |
| 92 | | 59 | NMR2; 2.32-2.37(3H, m), 3.46(2H, s), 8.56(1H, d, J = 8.3 Hz), 6.94-7.12(4H, m), 7.27-7.36(2H, m). |
| 93 | | 58 | NMR2; 6.97(1H, dd, J = 9.1, 7.9 Hz), 7.06-7.14(2H, m), 7.21-7.32(1H, m), 7.38-7.49(2H, m), 7.98(1H, ddd, J = 9.1, 2.7, 1.5 Hz), 8.09(1H, dd, J = 10.3, 2.7 Hz). |
| 94 | | 59 | NMR2; 3.67(2H, bs), 6.40(1H, ddd, J = 8.6, 2.7, 1.2 Hz), 6.49(1H, dd, J = 12.0, 2.7 Hz), 6.86-6.96(3H, m), 5.96-7.06(1H, m), 7.22-7.32(2H, m). |

TABLE 1-10

| REX | STR | RProp | DATA |
|---|---|---|---|
| 95 | | 58 | NMR2; 6.90-7.01(2H, m), 7.10-7.21(1H, m), 7.30-7.41(2H, m), 7.90-8.01(2H, m). |
| 96 | | 59 | NMR2; 3.78(2H, s), 6.23-6.34(2H, m), 6.87-5.98(2H, m), 6.96-7.09(1H, m), 7.21-7.34(2H, m). |
| 97 | | 58 | NMR2; 6.93(1H, dt, J = 9.4, 2.3 Hz), 6.96-7.05(2H, m), 7.07(1H, dd, J = 9.0, 0.6 Hz), 7.42(1H, td, J = 8.3, 6.5 Hz), 8.50(1H, dd, J = 9.0, 2.8 Hz), 9.05(1H, dd, J = 2.9, 0.6 Hz). |
| 98 | | 59 | NMR2; 3.48(2H, brs), 8.82(1H, dd, J = 8.6, 0.7 Hz), 7.05-7.22(5H, m), 7.64(1H, dd, J = 3.0, 0.7 Hz). |

TABLE 1-10-continued
| REX | STR | RProp | DATA |
|---|---|---|---|
| 99 | 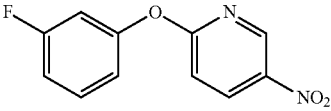 | 58 | NMR2; 6.59-7.05(3H, m), 7.07(1H, dd, J = 9.0, 0.6 Hz), 7.42(1H, td, J = 8.3, 6.5 Hz), 8.50(1H, dd, J = 9.0, 2.8 Hz), 9.05(1H, dd, J = 2.9, 0.6 Hz) |
| 100 | 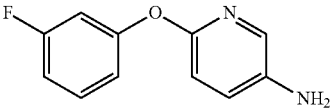 | 59 | NMR2; 3.58(2H, brs), 6.72-6.87(4H, m), 7.10(1H, ddd, J = 8.6, 3.0, 1.5 Hz), 7.22-7.33(1H, m), 7.70-7.78(1H, m). |
| 101 | 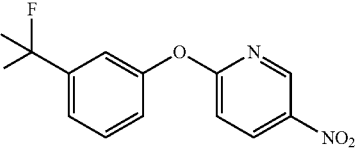 | 58 | NMR2; 7.06-7.15(1H, m), 7.34-7.41(1H, m), 7.42-7.47(1H, m), 7.52-7.63(2H, m), 8.52(1H, dd, J = 9.0, 2.8 Hz), 9.03(1H, dd, J = 2.8, 0.6 Hz). |
| 102 | 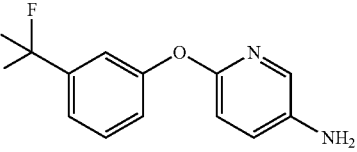 | 59 | NMR2; 3.59(2H, s), 6.78-6.85(1H, m), 7.07-7.15(1H, m), 7.19-7.25(1H, m), 7.28-7.32(1H, m), 7.33-7.39(1H, m), 7.44(1H, t, J = 7.8 Hz), 7.69-7.75(1H, m). |
| 103 | 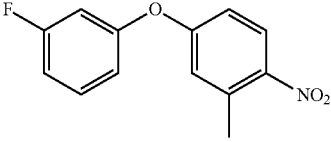 | 58 | NMR2; 2.61(3H, s), 6.80(1H, dt, J = 9.5, 2.4 Hz), 6.83-6.91(3H, m), 6.94(1H, tdd, J = 8.3, 2.5, 0.9 Hz), 7.37(1H, td, J = 8.3, 6.5 Hz), 8.03-8.10(1H, m). |
| 104 | 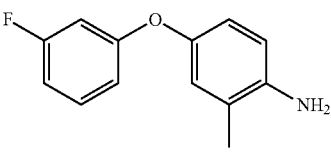 | 59 | NMR2; 2.16(3H, s), 3.54(2H, s), 6.60(1H, dt, J = 10.7, 2.4 Hz), 6.64-6.81(8H, m), 7.20(1H, td, J = 8.3, 6.7 Hz). |
| 105 | 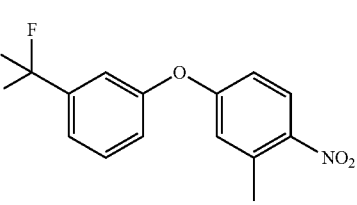 | 58 | NMR2; 2.62(3H, s), 6.84-6.93(2H, m), 7.21-7.29(1H, m), 7.33(1H, dq, J = 2.3, 0.7 Hz), 7.45-7.59(2H, m), 8.08(1H, d, J = 8.8 Hz). |
| 106 | 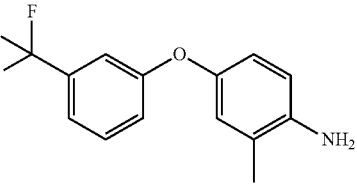 | 59 | NMR2; 2.17(3H, s), 3.56(2H, s), 6.68(1H, d, J = 8.4 Hz), 6.72-6.82(2H, m), 7.04-7.11(1H, m), 7.12-7.18(1H, m), 7.20-7.30(1H, m), 7.32-7.41(1H, m). |

TABLE 1-11

| REX | STR | RProp | DATA |
|---|---|---|---|
| 107 | (structure: 3-(trifluoromethoxy)phenoxy linked to phenoxy with NO2 and methyl) | 58 | NMR2; 2.61(3H, s), 6.85-6.93(2H, m), 6.93-6.98(1H, m), 7.00(1H, ddd, J = 8.2, 2.3, 0.9 Hz), 7.05-7.14(1H, m), 7.43(1H, t, J = 8.3 Hz), 8.04-8.11(1H, m). |
| 108 | (structure: 3-(trifluoromethoxy)phenoxy linked to phenoxy with NH2 and methyl) | 59 | NMR2; 2.16(3H, s), 3.55(2H, s), 6.67(1H, d, J = 8.4 Hz), 6.72-6.89(5H, m), 7.25(1H, t, J = 8.3 Hz). |
| 109 | (structure: 3-fluorophenoxy naphthalene NO2) | 58 | NMR2; 6.81(1H, d, J = 8.6 Hz), 6.90(1H, ddd, J = 2.3, 2.3, 9.5 Hz), 6.93-7.03(2H, m), 7.42(1H, ddd, J = 6.5, 8.3, 8.3 Hz), 7.65-7.71 (1H, m), 7.81 (1H, ddd, J = 1.4, 7.1, 8.6 Hz), 8.27(1H, d, J = 8.6 Hz), 8.45(1H, d, J = 8.4 Hz), 8.76(1H, d, J = 8.8 Hz). |
| 110 | (structure: 3-fluorophenoxy naphthalene NH2) | 59 | NMR2; 4.11(2H, br), 6.62(1H, ddd, J = 2.4, 2.4, 10.6 Hz), 6.66-6.77(3H, m), 7.00(1H, d, J = 8.0 Hz), 7.20(1H, ddd, J = 6.7, 6.7, 8.3 Hz), 7.43-7.54(2H, m), 7.83-7.89(1H, m), 7.93-7.98(1H, m). |
| 111 | (structure: 6-chloropyridazin-3-yl uracil) | 111 | NMR2; 5.85(1H, d, J = 8.1 Hz), 8.07-8.24(3H, m), 11.73(1H, s). |

EXAMPLES

Example 1

Synthesis of 3-Methoxy-6-(2-Phenoxypyrimidin-5-Yl)Pyridazine

A mixture containing 2-phenoxy-5-(4,4,5,5-tetramethyl-1,3,2-dioxaborolan-2-yl)pyrimidine (5.00 g), 3-chloro-6-methoxypyridazine (3.64 g), PdCl$_2$ (dppf) DCM (0.137 g), K$_3$PO$_4$ (7.12 g), 1,4-dioxane (50 mL), and water (25 mL) was heated to reflux under a nitrogen atmosphere for 2 hours. The reaction solution was poured into water, and the product was extracted with AcOEt. The organic layer was washed with water and brine and dried with anhydrous sodium sulfate and then concentrated. The residue was purified through silica gel column chromatography (DCM/AcOEt) to obtain the object compound (4.42 g).

Example 4

Synthesis of 3-(2-(3-Fluorophenoxy)Pyrimidin-5-Yl)-6-Methoxypyridazine

A mixture containing 5-bromo-2-(3-fluorophenoxy)pyrimidine (2.234 g), (BPin)$_2$ (2.63 g), PdCl$_2$ (dppf) DCM (0.282 g), AcOK (1.358 g), and 1,4-dioxane (20 mL) was heated to reflux under a nitrogen atmosphere for 2 hours. 3-Chloro-6-methoxypyridazine (1.00 g), PdCl$_2$ (dppf) DCM (0.282 g), K$_3$PO$_4$ (2.94 g), and water (5 mL) were added to the reaction solution and the mixture was heated to reflux under a nitrogen atmosphere overnight. Water and AcOEt were added to the reaction solution, the mixture was filtered through Celite, and the product was then extracted with AcOEt. The organic layer was washed with water and brine and dried with anhydrous sodium sulfate and then concentrated. The precipitated crystals were washed with EtOH to obtain the object compound (947 mg).

Example 6

Synthesis of 5-(6-Methoxypyridin-3-Yl)-2-Phenoxypyrimidine

A mixture containing 5-bromo-2-phenoxypyrimidine (1.0 g), 2-methoxy-5-pyridineboronic acid (0.914 g), PdCl$_2$ (dppf) DCM (0.163 g), K$_3$PO$_4$ (1.691 g), 1,4-dioxane (10 mL), and water (5 mL) was heated to reflux under a nitrogen atmosphere for 2 hours. The reaction solution was poured into water, and the product was extracted with AcOEt. The organic layer was washed with water and brine and dried with anhydrous sodium sulfate and then concentrated. The residue was purified through silica gel column chromatography (DCM/AcOEt), and the obtained solid was washed with EtOH to obtain the object compound (821 mg).

Example 7

Synthesis of 2-Phenoxy-5-(Pyridin-3-Yl)Pyrimidine

A mixture containing 5-bromo-2-phenoxypyrimidine (1.0 g), 3-pyridineboronic acid (0.734 g), $PdCl_2$ (dppf) DCM (0.163 g), $K_3PO_4$ (1.691 g), 1,4-dioxane (10 mL), and water (5 mL) was heated to reflux under a nitrogen atmosphere for 2 hours. The reaction solution was poured into water, and the product was extracted with AcOEt. The organic layer was washed with water and brine and dried with anhydrous sodium sulfate and then concentrated. The residue was purified through silica gel column chromatography (DCM/AcOEt), and the obtained solid was washed with EtOH to obtain the object compound (386 mg).

Example 11

Synthesis of 3-(2-Phenoxypyrimidin-5-Yl)Pyridine 1-Oxide

A mixture containing 2-phenoxy-5-(pyridin-3-yl)pyrimidine (749 mg), hydrous 77% m-CPBA (1,616 mg), and DCM (15 mL) was stirred at room temperature overnight. Dimethyl sulfide (309 μl) was added to the reaction solution and stirred for some time, and a saturated $NaHCO_3$ aqueous solution was then added thereto, and the product was extracted with AcOEt. The organic layer was washed with water and brine and dried with anhydrous sodium sulfate and concentrated. The residue was purified through silica gel column chromatography (Hexane/AcOEt), and the obtained solid was washed with AcOEt to obtain the object compound (118 mg).

Example 24

Synthesis of 6-(2-(3-Fluorophenoxy)Pyrimidin-5-Yl)Pyridazin-3-Amine

A mixture containing 2-(3-fluorophenoxy)-5-(4,4,5,5-tetramethyl-1,3,2-dioxaborolan-2-yl)pyrimidine (581 mg), 3-amino-6-chloropyridazine (202 mg), $K_3PO_4$ (1.11 g), $PdCl_2$ (dppf) DCM (68 mg), 1,4-dioxane (20 mL), and water (2 mL) was heated to reflux under a nitrogen atmosphere for 2 hours. The reaction solution was poured into water, and the product was extracted with AcOEt. The organic layer was washed with water and brine and dried with anhydrous sodium sulfate and then concentrated. The residue was purified through silica gel chromatography (Hexane/AcOEt, AcOEt/MeOH), and the obtained solid was washed with IPE to obtain the object compound (100 mg).

Example 30

Synthesis of 6-(2-Phenoxypyrimidin-5-Yl)Pyridazin-3-Amine

A mixture containing 3-amino-6-chloropyridazine (205 mg), 2-phenoxy-5-(4,4,5,5-tetramethyl-1,3,2-dioxaborolan-2-yl)pyrimidine (526 mg), $K_3PO_4$ (1.11 g), $PdCl_2$ (dppf) DCM (65.2 mg), 1,4-dioxane (10 mL), and water (2 mL) was heated to reflux under a nitrogen atmosphere for 5 hours and a half. The reaction solution was poured into water, and the product was extracted with AcOEt. The organic layer was washed with water and brine, and dried with anhydrous sodium sulfate and then concentrated. The residue was purified through silica gel chromatography (Hexane/AcOEt, AcOEt/MeOH) to obtain the object compound (180 mg).

Example 36

Synthesis of 5-(2-Phenoxypyrimidin-5-Yl)Pyridin-2-Amine

A mixture containing 2-phenoxy-5-(4,4,5,5-tetramethyl-1,3,2-dioxaborolan-2-yl)pyrimidine (386 mg), 2-amino-5-bromopyridine (209 mg), $K_3PO_4$ (1.0 g), $PdCl_2$ (dppf) DCM (43.7 mg), 1,4-dioxane (20 mL), and water (2 mL) was heated to reflux under a nitrogen atmosphere for 2.75 hours. The reaction solution was poured into water, and the product was extracted with AcOEt. The organic layer was washed with water and brine and then dried with anhydrous sodium sulfate and then concentrated. The residue was purified through silica gel chromatography (Hexane/AcOEt), and the obtained solid was washed with IPE to obtain the object compound (161 mg).

Example 38

Synthesis of 3-(2-Phenoxypyrimidin-5-Yl)-6-(Trifluoromethyl)Pyridazine

A mixture containing 3-chloro-6-(trifluoromethyl)pyridazine (209 mg), 2-phenoxy-5-(4,4,5,5-tetramethyl-1,3,2-dioxaborolan-2-yl)pyrimidine (373 mg), $K_3PO_4$ (780 mg), $PdCl_2$ (dppf) DCM (29.3 mg), 1,4-dioxane (20 mL), and water (2 mL) was heated to reflux under a nitrogen atmosphere for 5 hours. The reaction solution was poured into water, and the product was extracted with AcOEt. The organic layer was washed with water and brine and then dried with anhydrous sodium sulfate and then concentrated. The residue was purified through silica gel chromatography (Hexane/AcOEt), and the obtained solid was washed with AcOEt to obtain the object compound (107 mg).

Example 60

Synthesis of 3-(2-(2-Fluorophenoxy)Pyrimidin-5-Yl)Pyridine 1-Oxide

A mixture containing 3-(2-(2-fluorophenoxy)pyrimidin-5-yl)pyridine (998 mg), hydrous 77% m-CPBA (1,255 mg), and DCM (15 mL) was stirred at room temperature overnight. Dimethyl sulfide and a saturated $NaHCO_3$ aqueous solution were added to the reaction solution, and the product was then extracted with AcOEt. The organic layer was washed with water and brine, and dried with anhydrous sodium sulfate and then concentrated. The residue was purified through silica gel column chromatography (AcOEt/MeOH), and the obtained solid was washed with EtOH to obtain the object compound (383 mg).

Example 63

Synthesis of 3-(2-(2,5-Difluorophenoxy)Pyrimidin-5-Yl)-6-Methoxypyridazine

A mixture containing 2,5-difluorophenol (132 mg), 3-methoxy-6-(2-(methylsulfonyl)pyrimidin-5-yl)pyridazine (167 mg), $K_2CO_3$ (176 mg), and DMF (5 mL) was stirred at room temperature for 2 hours. Water was added to the

Example 69

Synthesis of 2-(6-(2-Phenoxypyrimidin-5-Yl) Pyridazin-3-Yl) Propan-2-Ol

Ethyl 6-(2-phenoxypyrimidin-5-yl)pyridazine-3-carboxylate (200 mg) was suspended in THF (3 mL), a THF solution (1.6 mL) containing 0.96 M methyl magnesium bromide was then added thereto under ice-cooling, and the mixture was stirred at room temperature overnight. The reaction solution was poured into a saturated ammonium chloride aqueous solution, and the product was extracted with AcOEt. The: organic layer was washed with water and brine and dried with anhydrous sodium sulfate, and then concentrated. The residue was purified through silica gel column chromatography (Hexane/AcOEt), and the obtained solid was washed with IPE to obtain the object compound (45 mg).

Example 72

Synthesis of (6-(2-Phenoxypyrimidin-5-Yl)Pyridazin-3-Yl) Methanol

Ethyl 6-(2-phenoxypyrimidin-5-yl)pyridazine-3-carboxylate (400 mg) was added to a mixture containing calcium chloride (551 mg), $NaBH_4$ (117 mg), THF (2 mL), and EtOH (2 mL) under ice-cooling, and the mixture was stirred for 30 minutes. A citric acid aqueous solution was added to the reaction solution, and the product was then extracted with AcOEt. The organic layer was washed with water and brine and dried with anhydrous sodium sulfate and then concentrated. The residue was purified through silica gel column chromatography (Hexane/AcOEt), and the obtained solid was washed with IPE to obtain the object compound (81 mg).

Example 84

Synthesis of 5-(2-(2,5-Difluorophenoxy)Pyrimidin-5-Yl)Pyridin-2-Amine

A mixture containing 5-(2-(methylsulfinyl)pyrimidin-5-yl)pyridin-2-amine (100 mg), 2,5-difluorophenol (130 mg), $K_2CO_3$ (236 mg), and DMF (7 mL) was stirred under a nitrogen atmosphere at 80° C. for 3.5 hours. Water was added to the reaction solution, and the product was then extracted with AcOEt. The organic layer was washed with water, dried with anhydrous sodium sulfate and then concentrated. The residue was purified through basic silica gel chromatography (Hexane/AcOEt), and the obtained solid was washed with Hexane/IPE to obtain the object compound (44 mg).

Example 88

Synthesis of 5-(2-(m-Tolyloxy)Pyrimidin-5-Yl)Pyridin-2-Amine

A mixture containing 5-(2-(dodecylsulfinyl)pyrimidin-5-yl)pyridin-2-amine (163 mg), m-cresol (0.10 mL), $K_2CO_3$ (483 mg), and DMF (10 mL) was stirred under a nitrogen atmosphere at 80° C. for 4 hours. Water was added to the reaction solution, and the product was then extracted with AcOEt. The organic layer was washed with water, dried with anhydrous sodium sulfate and then concentrated. The residue was purified through basic silica gel chromatography (Hexane/AcOEt), and the obtained solid was washed with IPE to obtain the object compound (50 mg).

Example 91

Synthesis of 6-(2-Phenoxypyrimidin-5-Yl)Pyridazin-3 (2H)-One

A mixture containing 3-(benzyloxy)-6-(2-phenoxypyrimidin-5-yl)pyridazine (2.54 g), 10% Pd/C (2 g), EtOH (25 mL), and THF (75 mL) was stirred under a hydrogen atmosphere at room temperature for 3 hours. The reaction solution was filtered through Celite, and the filtrate was concentrated. The residue was crystallized from EtOH to obtain the object compound (1.38 g).

Example 92

Synthesis of 6-(2-Phenoxypyrimidin-5-Yl)-4,5-Dihydropyridazin-3 (2H)-One

A mixture containing 6-(2-phenoxypyrimidin-5-yl)pyridazin-3 (2H)-one (1.08 g), zinc powder (0.53 g), and AcOH (10 mL) was heated to reflux for 1 hour. The reaction solution was concentrated, water was added to the residue, and the product was extracted with AcOEt. The organic layer was washed with water and brine and dried with anhydrous sodium sulfate and then concentrated. The residue was purified through silica gel column chromatography (DCM/MeOH) and then washed with EtOH to obtain the object compound (583 mg).

Example 94

Synthesis of 6-(2-(3-Fluorophenoxy)Pyrimidin-5-Yl)-4,5-Dihydropyridazin-3 (2H)-One A mixture containing 6-(2-(3-fluorophenoxy)pyrimidin-5-yl)pyridazin-3 (2H)-one (1.02 g), zinc powder (0.56 g), and AcOH (10 mL) was heated to reflux for 3 hours. The reaction solution was concentrated, water was added to the residue, and the product was extracted with AcOEt. The organic layer was washed with water and brine and dried with anhydrous sodium sulfate and then concentrated. The residue was purified through silica gel column chromatography (DCM/AcOEt), and the obtained solid was washed with EtOH to obtain the object compound (587 mg).

Example 106

Synthesis of 5-(2-(m-Tolyloxy)Pyrimidin-5-Yl)Pyridin-2 (1H)-One

A mixture containing 5-(6-methoxypyridin-3-yl)-2-(m-tolyloxy)pyrimidine (425 mg), sodium iodide (652 mg), chlorotrimethylsilane (0.552 mL), and MeCN (5 mL) was stirred at room temperature overnight. Water was added to the reaction solution, and the product was then extracted with AcOEt. The organic layer was washed with water and brine, dried with anhydrous magnesium sulfate, and then concentrated. The residue was: purified through silica gel

Example 114

Synthesis of 4-(2-Phenoxypyrimidin-5-Yl)Pyridazin-3 (2H)-One

A mixture containing 4-(2-phenoxypyrimidin-5-yl)-2-(tetrahydro-2H-pyran-2-yl)pyridazin-3 (2H)-one (1.085 g), TFA (10 mL), and DCM (10 mL) was stirred at room temperature for 1 hour. The reaction solution was concentrated, a saturated $NaHCO_3$ aqueous solution was added to the residue for neutralization, and the product was then extracted with DCM. The organic layer was washed with water and brine, and dried with anhydrous sodium sulfate and then concentrated. The residue was purified through silica gel column chromatography (DCM/AcOEt), and the obtained solid was then washed with EtOH to obtain the object compound (672 mg).

Example 118

Synthesis of 4-(2-Phenoxypyrimidin-5-Yl) Quinoline

A mixture containing 2-phenoxy-5-(4,4,5,5-tetramethyl-1,3,2-dioxaborolan-2-yl)pyrimidine (500 mg), 4-bromoquinoline (419 mg), $K_3PO_4$ (712 mg), $PdCl_2$ (dppf) DCM (13.70 mg), 1,4-dioxane (5 mL), and water (2.5 mL) was heated to reflux under a nitrogen atmosphere for 1.5 hours. Water was added to the reaction solution, the product was extracted with AcOEt. The organic layer was dried with anhydrous sodium sulfate and then concentrated. The residue was purified through silica gel column chromatography (Hexane/AcOEt), and the obtained solid was washed with IPE to obtain the object compound (413 mg).

Example 119

Synthesis of 6-(2-Phenoxypyrimidin-5-Yl) Imidazo[1,2-a]Pyridine

A mixture containing 2-phenoxy-5-(4,4,5,5-tetramethyl-1,3,2-dioxaborolan-2-yl)pyrimidine (400 mg), 6-bromo-imidazo[1,2-a]pyridine (291 mg), $PdCl_2$ (dppf) DCM (110 mg), $K_3PO_4$ (570 mg), 1,4-dioxane (4 mL), and water (2 mL) was stirred under a nitrogen atmosphere at 100° C. for 3 hours. AcOEt and water were added to the reaction solution and the mixture was filtered through Celite. The organic layer was washed with water and dried with anhydrous sodium sulfate and then concentrated. The residue was purified through basic silica gel column chromatography (DCM/AcOEt) to obtain the object compound (318 mg).

Example 123

Synthesis of 6-(2-Phenoxypyrimidin-5-Yl) Imidazo[1,2-b]Pyridazine

A mixture containing 2-phenoxy-5-(4,4,5,5-tetramethyl-1,3,2-dioxaborolan-2-yl)pyrimidine (400 mg), 6-chloro-imidazo[1,2-b]pyridazine (227 mg), $PdCl_2$ (dppf) DCM (110 mg), $K_3PO_4$ (570 mg), 1,4-dioxane (4 mL), and water (2 mL) was stirred under a nitrogen atmosphere at 95° C. for 3 hours. AcOEt and water were added to the reaction solution, and the mixture was then filtered through Celite. The organic layer was washed with water, dried with anhydrous sodium sulfate and then concentrated. The residue was purified through basic silica gel column chromatography (Hexane/AcOEt) to obtain the object compound (329 mg).

Example 137

Synthesis of 6-(2-Phenoxypyrimidin-5-Yl)-1H-Pyrrolo[3,2-b]Pyridine

A mixture containing 2-phenoxy-5-(4,4,5,5-tetramethyl-1,3,2-dioxaborolan-2-yl)pyrimidine (400 mg), 6-bromo-1-(triisopropylsilyl)-1H-pyrrolo[3,2-b]pyridine (522 mg), $PdCl_2$ (dppf) DCM (110 mg), $K_3PO_4$ (570 mg), 1,4-dioxane (4 mL), and water (2 mL) was stirred under a nitrogen atmosphere at 90° C. for 3 hours. AcOEt and water were added to the reaction solution, and the mixture was then filtered through Celite. The organic layer was washed with water, dried with anhydrous sodium sulfate and then concentrated. The residue was dissolved in THF (5 mL), 1N-TBAF (1.34 mL) was added thereto, the mixture was stirred at room temperature for 1 hour, and the reaction solution was concentrated under a reduced pressure. The residue was purified through basic silica gel column chromatography (DCM/AcOEt) to obtain the object compound (325 mg).

Example 139

Synthesis of 4-(2-Phenoxypyrimidin-5-Yl)-1,8-Naphthyridine

A mixture containing 2-phenoxy-5-(4,4,5,5-tetramethyl-1,3,2-dioxaborolan-2-yl)pyrimidine (300 mg), 4-chloro-[1,8]naphthyridine (199 mg), $K_3PO_4$ (427 mg), $PdCl_2$ (dppf) DCM (6.56 mg), 1,4-dioxane (4 mL), and water (2 mL) was heated to reflux under a nitrogen atmosphere for 3 hours. Water was added to the reaction solution, the product was extracted with AcOEt. The organic layer was dried with anhydrous sodium sulfate and then concentrated. The residue was purified through silica gel column chromatography (MeOH/DCM), and the obtained solid was recrystallized from AcOEt to obtain the object compound (167 mg).

Example 163

Synthesis of 6-(2-(3-Chlorophenoxy)Pyrimidin-5-Yl) Imidazo[1,2-a]Pyridine

A mixture containing 6-(2-(dodecylsulfonyl)pyrimidin-5-yl) imidazo[1,2-a]pyridine (300 mg), 1-chloro-3-hydroxybenzene (0.089 mL), $K_2CO_3$ (193 mg), and DMF (3 mL) was stirred at 80° C. for 5 hours. The reaction solution was poured into ice water, and the product was extracted with AcOEt. The organic layer was washed with water, dried with anhydrous sodium sulfate and then concentrated. The residue was purified through basic column chromatography (DCM/AcOEt) to obtain the object compound (194 mg).

Example 172

Synthesis of 5-(2-Phenoxypyrimidin-5-Yl)-1H-Pyrrolo[3,2-b]Pyridin-2 (3H)-One

A mixture containing 2-phenoxy-5-(4,4,5,5-tetramethyl-1,3,2-dioxaborolan-2-yl)pyrimidine (560 mg), 5-bromo-1H,2H,3H-pyrrolo[3,2-b]pyridin-2-one (200 mg), $PdCl_2$ (dppf) DCM (38.3 mg), $K_3PO_4$ (399 mg), 1,4-dioxane (4 mL), and water (2 mL) was stirred under a nitrogen atmosphere at 90° C. for 5 hours. AcOEt and water were added to the reaction solution, and the mixture was then filtered through Celite. The organic layer was washed with water, dried with anhydrous sodium sulfate and then concentrated. The residue was purified through basic silica gel column chromatography (DCM/AcOEt) to obtain the object compound (98 mg).

Example 173

Synthesis of 6-(2-Phenoxypyrimidin-5-Yl)-[1,2,3]Triazolo[1,5-a]Pyridine

A mixture containing 2-phenoxy-5-(4,4,5,5-tetramethyl-1,3,2-dioxaborolan-2-yl)pyrimidine (330 mg), 6-bromo-[1,2,3]triazolo[1,5-a]pyridine (241 mg), $PdCl_2$ (dppf) DCM (45.2 mg), $K_3PO_4$ (470 mg), 1,4-dioxane (4 mL), and water (2 mL) was stirred at 90° C. for 5 hours. AcOEt and water were added to the reaction solution, and the mixture was then filtered through Celite. The filtrate was separated, and the organic layer was washed with water, dried with anhydrous sodium sulfate and then concentrated. The residue was purified through basic silica gel column chromatography (DCM/AcOEt) to obtain the object compound (250 mg).

Example 198

Synthesis of 5-Methyl-6-(2-Phenoxypyrimidin-5-Yl)Imidazo[1,2-a]Pyridine Hydrochloride A mixture containing 2-phenoxy-5-(4,4,5,5-tetramethyl-1,3,2-dioxaborolan-2-yl)pyrimidine (330 mg), 6-bromo-5-methyl-imidazo[1,2-a]pyridine (257 mg), $PdCl_2$ (dppf) DCM (45.2 mg), $K_3PO_4$ (470 mg), 1,4-dioxane (4 mL), and water (2 mL) was stirred at 90° C. for 5 hours. AcOEt and water were added to the reaction solution, and the mixture was then filtered through Celite. The organic layer was washed with water and dried with anhydrous magnesium sulfate and then concentrated. The residue was purified through basic silica gel column chromatography (DCM/AcOEt). The obtained oily material was dissolved in EtOH, a 3 mL 1N-HCl EtOH solution was added thereto, the mixture was stirred, and the reaction solution was then concentrated. The precipitated crystals were recrystallized from EtOH/AcOEt to obtain the object compound (349 mg).

Example 220

Synthesis of 1-(2-Phenoxypyrimidin-5-Yl)Tetrahydropyrimidin-2(1H)-One

60% NaH (0.148 g) was added to a DMF (12 mL) solution containing 1-(3-chloropropyl)-3-(2-phenoxypyrimidin-5-yl)urea (1.25 g) while ice-cooling and stirring, and the mixture was stirred at room temperature for 2 days. Water was added to the residue, and the product was extracted with AcOEt. The organic layer was washed with water and brine, and dried with anhydrous sodium sulfate and then concentrated. The precipitated crystals were washed with EtOH to obtain the object compound (181 mg).

Example 221

Synthesis of 1-(2-(3-Fluorophenoxy)Pyrimidin-5-Yl)Tetrahydropyrimidin-2 (1H)-One 2-(3-Fluorophenoxy)pyrimidin-5-amine (1.00 g) was dissolved in THF (10 mL) and DMF (10 mL), and 3-chloropropyl isocyanate (0.800 mL) was added thereto, and the mixture was stirred at 50° C. for 3 hours. Water was added to the reaction solution, and the precipitated crystals were then collected by filtration to obtain an intermediate (1.41 g). The intermediate was dissolved in DMF (14 mL), 60% NaH (0.214 g) was added thereto under ice-cooling, and the mixture was stirred at room temperature for 1 hour. Ice water was added to the reaction solution, and the product was then extracted with AcOEt. The organic layer was washed with water and brine, and dried with anhydrous sodium sulfate and then concentrated. The residue was purified through silica gel column chromatography (AcOEt/MeOH), and the obtained solid was washed with EtOH to obtain the object compound (460 mg).

Example 223

Synthesis of 2-Phenoxy-5-(Piperidine-1-Yl)Pyrimidine

A mixture containing 5-bromo-2-phenoxypyrimidine (500 mg), piperidine (0.256 mL), $Pd(OAc)_2$ (447 mg), $tBu_3P \cdot HBF_4$ (578 mg), NaOtBu (191 mg), and toluene (10 mL) was stirred under a nitrogen atmosphere at 100° C. for 1 hour. AcOEt and water were added to the reaction solution, and the mixture was then filtered through Celite. The organic layer was washed with water and dried with anhydrous magnesium sulfate and then concentrated. The residue was purified through silica gel chromatography (Hexane/AcOEt) to obtain the object compound (53 mg).

Example 226

Synthesis of 1-(2-Phenoxypyrimidin-5-Yl)Piperidin-4-Ol

TBAF (0.56 mL) was added to THF (6 mL) containing 2-phenoxy-5-(4-(triisopropylsilyloxy) piperidin-1-yl)pyrimidine (240 mg), and the mixture was stirred at room temperature for 30 minutes. The reaction solution was concentrated, the residue was purified through silica gel column chromatography (Hexane/AcOEt), and crystallized from Hexane/AcOEt to obtain the object compound (110 mg).

Example 229

Synthesis of 4-(2-Phenoxypyrimidin-5-Yl)Morpholin-3-One

A mixture containing 5-iodo-2-phenoxypyrimidine (500 mg), 3-ketomorpholine (254 mg), copper iodide (I) (31.9 mg), $K_3PO_4$ (712 mg), (1R,2R)-N,N-dimethyl-1,2-cyclohexanediamine (0.053 mL), and 1,4-dioxane (6 mL) was stirred at 90° C. for 4 hours. The reaction solution was filtered through Celite, and the filtrate was concentrated. The residue was purified through silica gel column chromatography (Hexane/AcOEt) to obtain the object compound (368 mg).

Example 239

Synthesis of 4-(2-Phenoxypyrimidin-5-Yl) Aniline

A mixture containing 5-(4-nitrophenyl)-2-phenoxypyrimidine (3.8 g), 10% Pd/C (0.4 g), and EtOH (80 mL) was stirred under a hydrogen atmosphere at room temperature for 1 hour. The reaction solution was filtered through Celite, and the filtrate was concentrated. The residue was purified through silica gel column chromatography (Hexane/AcOEt) to obtain a desired white solid product (2.5 g).

Example 240

Synthesis of 6-(2-Phenoxypyrimidin-5-Yl)Benzo[d]
Thiazol-2-Amine

An acetic acid (2 mL) solution containing bromine (0.140 mL) was added to an acetic acid (6 mL) solution containing 4-(2-phenoxypyrimidin-5-yl) aniline (600 mg) and ammonium thiocyanate (382 mg) while ice-cooling and stirring. After 1 hour, the reaction solution was poured into ice water, a 28% aqueous ammonia solution was added until the reaction system became basic, and the product was then extracted with AcOEt. The organic layer was washed with water and dried with anhydrous magnesium sulfate and then concentrated. The residue was purified through silica gel column chromatography (DCM/AcOEt) to obtain the object compound (542 mg).

Example 257

Synthesis of 5-(2-Phenoxypyrimidin-5-Yl)-1H-Benzo[d]Imidazole Oxalate

A mixture containing 2-phenoxy-5-(4,4,5,5-tetramethyl-1,3,2-dioxaborolan-2-yl)pyrimidine (400 mg), 5-bromo-1H-benzo[d]imidazole (291 mg), PdCl$_2$ (dppf) DCM (110 mg), K$_3$PO$_4$ (570 mg), 1,4-dioxane (4 mL), and water (2 mL) was stirred under a nitrogen atmosphere at 95° C. for 3 hours. AcOEt and water were added to the reaction solution, and the mixture was then filtered through Celite. The organic layer was washed with water and dried with anhydrous magnesium sulfate and then concentrated. The residue was purified through silica gel column chromatography (Hexane/AcOEt). The obtained oily material was dissolved in ethanol, and an ethanol solution (1 mL) containing oxalic acid (80 mg) was added thereto. The precipitate was collected by filtration and dried to obtain the object compound (250 mg).

Example 262

Synthesis of
5-(2-Phenoxypyrimidin-5-Yl)-1H-Indole

A mixture containing 2-phenoxy-5-(4,4,5,5-tetramethyl-1,3,2-dioxaborolan-2-yl)pyrimidine (400 mg), 5-bromo-1-(triisopropylsilyl)-1H-indole (520 mg), PdCl$_2$ (dppf) DCM (110 mg), K$_3$PO$_4$ (570 mg), 1,4-dioxane (4 mL), and water (2 mL) was stirred under a nitrogen atmosphere at 80° C. for 3 hours. AcOEt and water were added to the reaction solution, and the mixture was then filtered through Celite. The filtrate was separated, and the organic layer was washed with water and dried with anhydrous magnesium sulfate and then concentrated. The residue was dissolved in THF (10 mL), TBAF (1.342 mL) was added thereto, and the mixture was stirred at room temperature for 1 hour. The reaction solution was concentrated and then purified through silica gel column chromatography (Hexane/AcOEt) to obtain the object compound (319 mg).

Example 302

Synthesis of 1-(4-(3-Fluorophenoxy)Phenyl)Dihydropyrimidine-2,4 (1H,3H)-Dione

A mixture containing 4-(3-fluorophenoxy) aniline (5.00 g), acrylic acid (2.53 mL), and toluene (40 mL) was stirred at 80° C. overnight. The reaction solution was concentrated, and urea (4.43 g) and AcOH (20 mL) were added thereto, and the mixture was heated to reflux for 3 hours. Water was added thereto, and the precipitate was collected by filtration. The precipitate was purified through silica gel column chromatography (DCM/MeOH) to obtain the object compound (2.33 g).

Example 305

Synthesis of 1-(4-(3-Fluorobenzyl)Phenyl)Dihydropyrimidine-2,4 (1H,3H)-Dione

A mixture containing m-fluorobenzyl chloride (0.11 mL), 1-(4-(4,4,5,5-tetramethyl-1,3,2-dioxaborolan-2-yl)phenyl) dihydropyrimidine-2,4 (1H,3H)-dione (0.25 g), K$_3$PO$_4$ (0.252 g), PdCl$_2$ (dppf) DCM (6.46 mg), DME (6.6 mL), and water (3.3 mL) was heated to reflux under a nitrogen atmosphere for 2 hours. The reaction solution was poured into ice water, and the product was extracted with AcOEt. The organic layer was washed with water and dried with anhydrous magnesium sulfate and then concentrated. The residue was purified through silica gel column chromatography (DCM/AcOEt) to obtain the object compound (30 mg).

Example 308

Synthesis of 1-(4-(3-Fluorophenoxy)Phenyl)-3-Methyldihydropyrimidine-2,4 (1H,3H)-Dione 60% NaH (32.0 mg) was added to a DMF (5 mL) solution containing 1-(4-(3-Fluorophenoxy)phenyl)dihydropyrimidine-2,4 (1H,3H)-dione (200 mg) while stirring at 0° C. and stirring was performed for 30 minutes. Methyl iodide (0.046 mL) was added thereto while stirring at 0° C. and then stirring was performed at room temperature overnight. The reaction solution was poured into ice water, and the product was extracted with AcOEt. The organic layer was washed with water and dried with anhydrous magnesium sulfate and then concentrated. The residue was purified through basic silica gel column chromatography (Hexane/AcOEt) to obtain the object compound (50 mg).

Example 314

Synthesis of 1-{4-[3-(Difluoromethoxy) Phenoxy] Phenyl}Dihydropyrimidine-2,4 (1H,3H)-Dione A mixture containing 1-[4-(3-hydroxy)phenyl]dihydropyrimidine-2,4 (1H,3H)-dione (337 mg), sodium chlorodifluoroacetate (344 mg), K$_2$CO$_3$ (234 mg) and DMF (1.7 mL) was stirred at 90° C. for 4 hours. Sodium chlorodifluoroacetate (344 mg) was added thereto and the mixture was additionally stirred for 2 hours. Hydrochloric acid was added to the reaction solution, and the product was then extracted with AcOEt. Washing with water, a NaOH aqueous solution, and water was performed, drying with anhydrous magnesium sulfate was performed, and concentration was then performed. The residue was purified through silica gel column chromatography (Hexane/AcOEt), and crystallized by adding EtOH, and washed with EtOH to obtain the object compound (79 mg).

Example 321

Synthesis of 1-[4-(6-Fluoropyridin-2-Yloxy)Phenyl] Dihydropyrimidine-2,4 (1H,3H)-Dione A mixture containing 1-(4-hydroxyphenyl)dihydropyrimidine-2,4 (1H,3H)-dione (412 mg), 2,6-difluoropyridine (0.218 mL), $K_2CO_3$ (553 mg), and DMSO (2 mL) was stirred at 100° C. for 2 hours. Water (10 mL) was added to the reaction solution and the precipitated solid was collected by filtration. The solid was purified through silica gel column chromatography (DCM/MeOH), and the obtained solid was washed with EtOH to obtain the object compound (244 mg).

Example 322

Synthesis of 1-(4-Phenoxyphenyl)Pyrimidine-2,4 (1H,3H)-Dione

A mixture containing 4-phenoxyphenylboronic acid (1.27 g), uracil (0.798 g), N,N,N',N'-tetramethylethylenediamine (0.896 mL), copper acetate (II) (0.539 g), MeOH (40 mL), and water (10 mL) was stirred at room temperature overnight. The reaction solution was poured into water, and the product was extracted with AcOEt. The organic layer was washed with water and dried with anhydrous magnesium sulfate and then concentrated. The residue was purified through silica gel column chromatography (DCM/AcOEt) to obtain the object compound (160 mg).

Example 327

Synthesis of 1-((1,1'-Biphenyl)-4-Yl)Dihydropyrimidine-2,4 (1H,3H)-Dione

A mixture containing monobromobenzene (0.158 mL), 1-[4-(4,4,5,5-tetramethyl-1,3,2-dioxaborolan-2-yl)phenyl] dihydropyrimidine-2,4 (1H,3H)-dione (316 mg), Pd(Ph$_3$P)$_4$ (57.8 mg), Na$_2$CO$_3$ (212 mg), DME (5 mL), and water (1 mL) was heated to reflux under a nitrogen atmosphere for 12 hours. AcOEt and anhydrous magnesium sulfate were added to the reaction solution, and the mixture was then filtered through Celite. The filtrate was concentrated, the residue was purified through silica gel chromatography (DCM/MeOH), and the obtained solid was washed with EtOH to obtain the object compound (35 mg).

Example 328

Synthesis of 6-Methyl-1-(4-Phenoxyphenyl)Dihydropyrimidine-2,4 (1H,3H)-Dione

A mixture containing 4-phenoxyaniline (0.50 g), toluene (5 mL), and crotonic acid (0.34 mL) was heated to reflux for 13 hours. Crotonic acid (0.34 mL) was added thereto, and additionally the mixture was heated to reflux for 6 hours. The reaction solution was concentrated, acetic acid (5 mL) and urea (0.324 g) were added thereto, and the mixture was heated to reflux for 17 hours. Concentrated hydrochloric acid (0.23 mL) was added to the reaction solution and heated to reflux for 30 minutes. Water was added to the reaction solution, and the product was then extracted with AcOEt. Washing with water, a saturated NaHCO$_3$ aqueous solution, and brine was performed, and drying with anhydrous magnesium sulfate was performed, and concentration was then performed. The residue was crystallized by adding EtOH (3 mL) and IPE (3 mL). The solid was collected by filtration, and washed with IPE to obtain the object compound (272 mg).

Example 337

Synthesis of 6,6-Dimethyl-1-(4-Phenoxyphenyl) Dihydropyrimidine-2,4 (1H,3H)-Dione A mixture containing 4-phenoxyaniline (1.0 g) and 3,3-dimethylacrylic acid (2.70 g) was stirred at 70° C. to 80° C. for 75 hours. Urea (0.648 g) and AcOH (6 mL) were added to the reaction solution and heated to reflux for 5 hours. Water (20 mL) was added to the reaction solution, and a saturated NaHCO$_3$ aqueous solution was then added thereto for neutralization. Extraction in AcOEt was performed, then the extract was washed with a saturated NaCl aqueous solution, dried with anhydrous magnesium sulfate, and concentrated. The residue was purified through silica gel column chromatography (Hexane/AcOEt), and the obtained solid was washed with EtOH to obtain the object compound (103 mg).

Example 343

Synthesis of 6-Ethyl-1-(4-Phenoxyphenyl)Dihydropyrimidine-2,4 (1H,3H)-Dione

A mixture containing 4-phenoxyaniline (0.50 g) and trans-2-pentenoic acid (1.37 mL) was stirred at 120° C. for 5 hours. AcOH (5 mL) and urea (0.324 g) were added to the reaction solution and heated to reflux for 3 hours. Water and AcOEt were added to the reaction solution and separated. The organic layer was washed with a saturated NaHCO$_3$ aqueous solution and brine, and dried with anhydrous magnesium sulfate, and then concentrated. The residue was purified through silica gel column chromatography . . . (DCM/MeOH) and crystallized by adding EtOH (2 mL). The solid was collected by filtration, and washed with EtOH and IPE to obtain the object compound (204 mg).

Example 344

Synthesis of 1-[4-(3,5-Difluoromethoxy)Phenyl] Dihydropyrimidine-2,4 (1H,3H)-Dione A mixture containing 1-(4-hydroxyphenyl)dihydropyrimidine-2,4 (1H,3H)-dione (330 mg), 1,3,5-trifluorobenzene (0.199 mL), K$_2$CO$_3$ (442 mg), and DMSO (2 mL) was stirred at 100° C. for 3.5 hours. 1,3,5-trifluorobenzene (0.199 mL) was added thereto, and additionally the mixture was stirred for 1.5 hours. Water (15 mL) was added to the reaction solution, and the precipitated solid was then collected by filtration, and washed with water and EtOH to obtain the object compound (35 mg).

Example 346

Synthesis of 1-(6-Phenoxypyridazin-3-Yl)Pyrimidine-2,4 (1H,3H)-Dione

A mixture containing phenol (1.017 mL), 1-(6-chloropyridazine-3-yl)pyrimidine-2,4 (1H,3H)-dione (2.00 g), Cs₂CO₃ (4.35 g), and DMSO (20 mL) was stirred at 130° C. overnight. A citric acid aqueous solution was added to the reaction solution, and the product was then extracted with AcOEt. The organic layer was washed with water and brine, dried with anhydrous sodium sulfate, and concentrated. The residue was washed with EtOH to obtain the object compound (588 mg).

Example 347

Synthesis of 1-(6-Phenoxypyridazin-3-Yl)Dihydropyrimidine-2,4 (1H,3H)-Dione 1-(6-Phenoxypyridazin-3-yl)pyrimidine-2,4 (1H,3H)-dione (577 mg) was dissolved in DMF (10 mL), and 50% water-containing 10% Pd/C (500 mg) was added, and the mixture was stirred under a hydrogen atmosphere at 50° C. for 6 hours. The reaction solution was filtered through Celite, and the filtrate was concentrated. The residue was purified through medium pressure column chromatography (DCM/AcOEt), and the obtained solid was washed with EtOH to obtain the object compound (122 mg).

The compounds of Examples 2, 3, 5, 8 to 10, 12 to 23, 25 to 29, 31 to 35, 37, 39 to 59, 61, 62, 64 to 68, 70, 71, 73 to 83, 85 to 87, 89, 90, 93, 95 to 105, 107 to 113, 115 to 117, 120 to 122, 124 to 136, 138, 140 to 162, 164 to 171, 174 to 197, 199 to 219, 222, 224, 225, 227, 228, 230 to 238, 241 to 256, 258 to 261, 263 to 301, 303, 304, 306, 307, 309 to 313, 315 to 320, 323 to 326, 329 to 336, 338 to 342, 345 and 348 to 350 were manufactured in the same manner as in Examples 1, 4, 6, 7, 11, 24, 30, 36, 38, 60, 63, 69, 72, 84, 88, 91, 92, 94, 106, 114, 118, 119, 123, 137, 139, 163, 172, 173, 198, 220, 221, 223, 226, 229, 239, 240, 257, 262, 302, 305, 308, 314, 321, 322, 327, 328, 337, 343, 344, 346 and 347. Structural formulae and physicochemical data of the compounds of Examples 1 to 350 are shown in Tables 2-1 to 2-37.

TABLE 2-1

| EX | STR | Prop | DATA |
|---|---|---|---|
| 1 | | 1 | NMR2; 4.20(3H, s), 7.11(1H, d, J = 9.2 Hz), 7.20-7.34(3H, m), 7.42-7.52(2H, m), 7.73(1H, d, J = 9.2 Hz), 9.16(2H, s). |
| 2 | | 1 | NMR2; 4.20(3H, s), 7.11(1H, d, J = 9.2 Hz), 7.20-7.34(3H, m), 7.42-7.52(2H, m), 7.73(1H, d, J = 9.2 Hz), 9.16(2H, s). |
| 3 | | 1 | NMR2; 4.21(3H, s), 7.11(1H, d, J = 9.2 Hz), 7.18-7.37(4H, m), 7.73(1H, d, J = 9.2 Hz), 9.16(2H, s). |
| 4 | | 4 | NMR2; 4.21(3H, s), 6.96-7.09(3H, m), 7.12(1H, d, J = 9.2 Hz), 7.37-7.47(1H, m), 7.74(1H, d, J = 9.2 Hz), 9.18(2H, s). |
| 5 | | 1 | NMR2; 4.21(3H, s), 7.08-7.25(5H, m), 7.73(1H, d, J = 9.2 Hz), 9.18(2H, s). |

TABLE 2-1-continued

| EX | STR | Prop | DATA |
|---|---|---|---|
| 6 | | 6 | NMR2; 3.99(3H, s), 6.87(1H, dd, J = 0.8, 8.6 Hz), 7.19-7.33(3H, m), 7.41-7.51(2H, m), 7.72(1H, dd, J = 2.6, 8.6 Hz), 8.32(1H, dd, J = 0.8, 2.5 Hz), 8.70(2H, s). |
| 7 | | 7 | NMR2; 7.20-7.34(3H, m), 7.39-7.52(3H, m), 7.79-7.87(1H, m), 8.69(1H, dd, J = 1.6, 4.8 Hz), 8.77(2H, s), 8.80(1H, dd, J = 0.9, 2.4 Hz). |
| 8 | | 7 | NMR2; 2.63(3H, s), 7.20-7.34(4H, m), 7.43-7.52(2H, m), 7.72(1H, dd, J = 2.5, 8.0 Hz), 8.67(1H, dd, J = 0.9, 2.5 Hz), 8.74(2H, s). |
| 9 | | 1 | NMR2; 7.20-7.34(3H, m), 7.42-7.52(4H, m), 8.70-8.77(2H, m), 8.82(2H, s). |
| 10 | | 1 | NMR2; 7.20-7.28(2H, m), 7.28-7.36(1H, m), 7.42-7.52(2H, m), 7.67(1H, dd, J = 5.3, 1.5 Hz), 8.83(1H, d, J = 5.3 Hz), 8.25(2H, s), 9.29(1H, d, J = 1.4 Hz). |

TABLE 2-2

| EX | STR | Prop | DATA |
|---|---|---|---|
| 11 | | 11 | NMR2; 7.19-7.36(3H, m), 7.37-7.53(4H, m), 8.22-8.31(1H, m), 8.38-8.44(1H, m), 8.74(2H, s). |
| 12 | | 1 | NMR2; 4.21(3H, s), 7.12(1H, d, J = 9.2 Hz), 7.41-7.49(1H, m), 7.50-7.64(3H, m), 7.75(1H, d, J = 9.2 Hz), 9.18(2H, s). |

TABLE 2-2-continued

| EX | STR | Prop | DATA |
|---|---|---|---|
| 13 | | 1 | NMR2; 2.80(3H, s), 7.41-7.50(2H, m), 7.50-7.64(3H, m), 7.73(1H, d, J = 8.7 Hz), 9.23(2H, s). |
| 14 | | 7 | NMR2; 7.41-7.49(2H, m), 7.50-7.64(3H, m), 7.81-7.89(1H, m), 8.70(1H, dd, J = 1.8, 4.9 Hz), 8.78(2H, s), 8.82(1H, dd, J = 0.9, 2.5 Hz). |
| 15 | | 7 | NMR2; 2.63(3H, s), 7.26-7.34(1H, m), 7.40-7.48(1H, m), 7.60-7.63(3H, m), 7.73(1H, dd, J = 2.4, 8.0 Hz), 8.55-8.71(1H, m), 8.75(2H, s). |
| 16 | | 7 | NMR2; 3.99(3H, s), 6.88(1H, dd, J = 0.8, 8.5 Hz), 7.40-7.48(1H, m), 7.49-7.63(3H, m), 7.73(1H, dd, J = 2.6, 8.6 Hz), 8.34(1H, dd, J = 0.8, 2.5 Hz), 8.71(2H, s). |
| 17 | | 1 | NMR2; 2.80(3H, s), 6.73-6.80(1H, m), 6.81-6.88(2H, m), 7.47(1H, d, J = 8.8 Hz), 7.74(1H, d, J = 8.7 Hz), 9.25(2H, s). |
| 18 | | 1 | NMR2; 6.73-6.80(1H, m), 6.80-6.87(2H, m), 7.46(1H, ddd, J = 0.8 Hz, 4.9 Hz, 7.9 Hz), 7.85(1H, ddd, J = 1.7 Hz, 2.4 Hz, 7.9 Hz), 8.71(1H, dd, J = 1.6 Hz, 4.8 Hz), 8.79(2H, s), 8.82(1H, dd, J = 0.8 Hz, 2.3 Hz). |
| 19 | | 1 | NMR2; 4.21(3H, s), 6.72-6.80(1H, m), 6.80-6.87(2H, m), 7.23(1H, d, J = 9.2 Hz), 7.75(1H, d, J = 9.2 Hz), 9.19(2H, s). |

TABLE 2-3

| EX | STR | Prop | DATA |
|---|---|---|---|
| 20 | | 1 | NMR2; 4.85(2H, s), 6.86(1H, d, J = 9.2 Hz), 7.08-7.16(2H, m), 7.16-7.25(2H, m), 7.57(1H, d, J = 9.2 Hz), 9.11(2H, s). |
| 21 | | 1 | NMR2; 2.80(3H, s), 6.96-7.10(3H, m), 7.37-7.49(2H, m), 7.73(1H, d, J = 8.7 Hz), 9.23(2H, s). |
| 22 | | 1 | NMR2; 2.65(3H, s), 7.17-7.35(5H, m), 7.42-7.52(2H, m), 8.81(1H, dd, J = 0.8, 5.2 Hz), 8.79(2H, s). |
| 23 | | 1 | NMR2; 3.99(3H, s), 6.89(1H, dd, J = 0.8, 1.6 Hz), 7.03(1H, dd, J = 1.6, 5.3 Hz), 7.17-7.34 (3H, m), 7.40-7.52(2H, m), 8.24-8.30(1H, m), 8.78(2H, s). |
| 24 | | 24 | NMR2; 4.86(2H, s), 6.87(1H, d, J = 9.2 Hz), 6.95-7.09(3H, m), 7.41(1H, td, J = 8.7, 6.6 Hz), 7.58(1H, d, J = 9.5 Hz), 9.12(2H, s). |
| 25 | | 1 | NMR2; 2.79(3H, s), 7.18-7.39(4H, m), 7.45(1H, d, J = 8.7 Hz), 7.72(1H, d, J = 8.7 Hz), 9.22(2H, s). |
| 26 | | 1 | NMR2; 4.87(2H, s), 6.86(1H, d, J = 9.2 Hz), 7.17-7.37(4H, m), 7.57(1H, d, J = 9.2 Hz), 9.11(2H, s). |
| 27 | | 1 | NMR2; 7.20-7.28(2H, m), 7.31(1H, ddt, J = 7.9, 7.0, 1.1 Hz), 7.43-7.53(2H, m), 7.83(1H, dd, J = 8.2, 0.9 Hz), 8.02(1H, ddd, J = 8.1, 2.3, 0.7 Hz), 8.80(2H, s), 8.91(1H, d, J = 2.2 Hz). |

TABLE 2-3-continued

| EX | STR | Prop | DATA |
|---|---|---|---|
| 28 | | 7 | NMR2; 2.40(3H, d, J = 0.7 Hz), 2.63(3H, s), 6.97-7.15(3H, m), 7.25-7.38(2H, m), 7.72(1H, dd, J = 2.4, 8.0 Hz), 8.67(1H, dd, J = 0.9, 2.5 Hz), 8.74(2H, s). |
| 29 | | 7 | NMR2; 2.40(3H, s), 3.99(3H, s), 6.57(1H, dd, J = 0.8, 8.8 Hz), 5.99-7.08(2H, m), 7.06-7.13(1H, m), 7.34(1H, t, J = 7.8 Hz), 7.71(1H, dd, J = 2.6, 8.6 Hz), 8.32(1H, dd, J = 0.8, 2.6 Hz), 8.70(2H, s). |

TABLE 2-4

| EX | STR | Prop | DATA |
|---|---|---|---|
| 30 | | 1 | NMR2; 4.86(2H, s), 6.86(1H, d, J = 9.2 Hz), 7.20-7.33(3H, m), 7.41-7.51(2H, m), 7.57(1H, d, J = 9.2 Hz), 9.11(2H, s). |
| 31 | | 1 | NMR2; 7.20-7.28(2H, m), 7.28-7.37 (1H, m), 7.43-7.53(2H, m), 7.83(1H, dd, J = 2.5, 5.4 Hz), 8.87(2H, s), 9.32(1H, dd, J = 1.2, 5.4 Hz), 9.45(1H, dd, J = 1.2, 2.5 Hz). |
| 32 | | 1 | NMR2; 6.96-7.09(3H, m), 7.38-7.47(1H, m), 7.64(1H, dd, J = 2.5, 5.4 Hz), 8.88(2H, s), 9.33(1H, dd, J = 1.2, 5.4 Hz), 9.45(1H, dd, J = 1.2, 2.5 Hz). |
| 33 | | 1 | NMR2; 7.09(1H, ddd, J = 8.5, 3.1, 0.7 Hz), 7.19-7.28(2H, m), 7.26-7.35(1H, m), 7.42-7.52(2H, m), 7.88-7.98(1H, m), 8.36-8.42(1H, m), 8.73(2H, s). |
| 34 | | 1 | NMR2; 2.54(3H, s), 7.21-7.34(4H, m), 7.42-7.55(3H, m), 8.55(2H, s), 5.58(1H, dd, J = 4.9, 1.8 Hz). |
| 35 | | 7 | NMR2; 2.41(3H, d, J = 0.8 Hz), 6.99-7.08(2H, m), 7.11(1H, tdd, J = 0.8, 1.6, 7.5 Hz), 7.35(1H, t, J = 7.7 Hz), 7.44(1H, ddd, J = 0.9, 4.9, 7.9 Hz), 7.79-7.87(1H, m), 8.59(1H, dd, J = 1.6, 4.8 Hz), 8.76(2H, s), 8.80(1H, dd, J = 0.9, 2.4 Hz). |

TABLE 2-4-continued

| EX | STR | Prop | DATA |
|---|---|---|---|
| 36 | | 36 | NMR2; 4.59(2H, s), 5.51(1H, dd, J = 8.5, 0.9 Hz), 7.19-7.32(3H, m), 7.40-7.50(2H, m), 7.58(1H, dd, J = 8.5, 2.5 Hz), 8.24(1H, dd, J = 2.5, 0.8 Hz), 8.67(2H, s). |
| 37 | | 1 | NMR2; 6.70 (1H, t, J = 55.3 Hz), 7.23-7.33 (3H, m), 7.46-7.50 (2H, m), 7.78(1H, d, J = 8.12 Hz), 7.98-8.00(1H, m), 8.79(2H, s), 8.83(1H, m). |
| 38 | | 38 | NMR2; 7.26(2H, dd, J = 8.6, 1.3 Hz), 7.32(1H, t, J = 7.5 Hz), 7.44-7.54(2H, m), 7.94(1H, d, J = 8.9 Hz), 8.01(1H, d, J = 8.9 Hz), 9.31(2H, s). |
| 39 | | 1 | NMR2; 4.55(2H, s), 6.86(1H, d, J = 9.2 Hz), 6.99-7.11(2H, m), 7.16-7.27(1H, m), 7.88(1H, d, J = 9.2 Hz), 9.12(2H, s). |

TABLE 2-5

| EX | STR | Prop | DATA |
|---|---|---|---|
| 40 | | 1 | NMR2; 4.87(2H, s), 6.87(1H, d, J = 9.2 Hz), 7.41-7.48(1H, m), 7.49-7.62(4H, m), 9.13(2H, s). |
| 41 | | 1 | NMR2; 4.87(2H, s), 6.75(1H, tt, J = 8.9, 2.3 Hz), 6.78-6.91(3H, m), 7.59(1H, d, J = 9.2 Hz), 9.14(2H, s). |

TABLE 2-5-continued

| EX | STR | Prop | DATA |
|---|---|---|---|
| 42 | | 1 | NMR2; 4.87(2H, s), 6.87(1H, d, J = 9.2 Hz), 7.11-7.24(3H, m), 7.42-7.52(1H, m), 7.59(1H, d, J = 9.2 Hz), 9.13(2H, s). |
| 43 | | 1 | NMR2; 4.61(2H, s), 6.62(1H, dd, J = 8.5, 0.8 Hz), 6.94-7.08(3H, m), 7.40(1H, td, J = 8.6, 6.5 Hz), 7.55-7.63(1H, m), 8.25(1H, d, J = 2.4 Hz), 8.68(2H, s). |
| 44 | | 1 | NMR2; 4.60(2H, s), 6.61(1H, dd, J = 8.5, 0.8 Hz), 7.07-7.15(2H, m), 7.15-7.25(2H, m), 7.58(1H, dd, J = 8.5, 2.5 Hz), 8.24(1H, dd, J = 2.5, 0.8 Hz), 8.67(2H, s). |
| 45 | | 1 | NMR2; 4.60(2H, s), 6.61(1H, dd, J = 8.5, 0.8 Hz), 7.17-7.36(4H, m), 7.59(1H, dd, J = 8.5, 2.5 Hz), 8.25(1H, dd, J = 2.5, 0.8 Hz), 8.67(2H, s). |
| 46 | | 1 | NMR2; 6.98-7.11(3H, m), 7.39-7.49(1H, m), 7.95(1H, d, J = 8.9 Hz), 8.03(1H, dd, J = 8.9, 0.8 Hz), 9.33(2H, s). |
| 47 | | 1 | NMR2; 2.55(3H, s), 6.96-7.07(2H, m), 7.04-7.11(1H, m), 7.26(1H, d, J = 12.6 Hz), 7.37-7.48(1H, m), 7.52(1H, dd, J = 7.7, 1.8 Hz), 8.56(2H, s), 8.59-8.60(1H, m). |
| 48 | | 1 | NMR2; 4.61(2H, s), 6.62(1H, dd, J = 8.5, 0.8 Hz), 7.10-7.23(3H, m), 7.42-7.51(1H, m), 7.60(1H, dd, J = 8.5, 2.5 Hz), 8.26(1H, dd, J = 2.5, 0.8 Hz), 8.69(2H, s). |
| 49 | | 1 | NMR2; 2.54(3H, s), 7.09-7.20(2H, m), 7.18-7.34(3H, m) 7.51(1H, dd, J = 7.7, 1.8 Hz), 8.58(2H, s), 8.59(1H, dd, J = 4.9, 1.8 Hz). |

TABLE 2-6
| EX | STR | Prop | DATA |
|---|---|---|---|
| 50 | 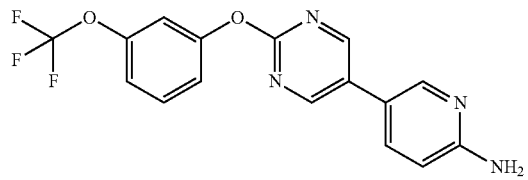 | 1 | NMR2; 4.62(2H, s), 6.62(1H, dd, J = 8.5, 0.9 Hz), 7.39-7.47(1H, m), 7.46-7.64(4H, m), 8.26(1H, dd, J = 2.5, 0.9 Hz), 8.68(2H, s). |
| 51 | 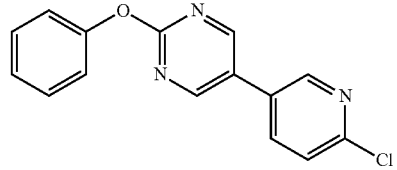 | 1 | NMR2; 7.19-7.27(2H, m), 7.26-7.36 (1H, m), 7.42-7.52(3H, m), 7.80(1H, dd, J = 8.3, 2.6 Hz), 8.57(1H, dd, J = 2.6, 0.8 Hz), 8.74(2H, s). |
| 52 | 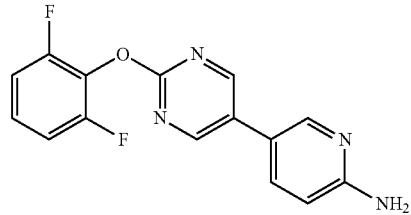 | 1 | NMR2; 4.61(2H, s), 6.61(1H, dd, J = 8.5, 0.8 Hz), 6.98-7.10(2H, m), 7.16-7.26(1H, m), 7.59(1H, dd, J = 8.5, 2.5 Hz), 8.26(1H, dd, J = 2.5, 0.9 Hz), 8.67(2H, s). |
| 53 | 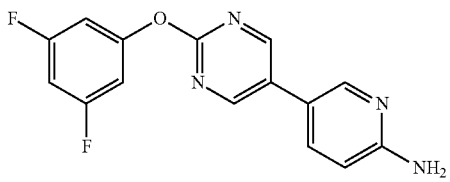 | 1 | NMR2; 4.63(2H, s), 6.62(1H, dd, J = 8.5, 0.8 Hz), 6.74(1H, tt, J = 8.9, 2.3 Hz), 6.76-6.87(2H, m), 7.60(1H, dd, J = 8.5, 2.5 Hz), 8.26(1H, dd, J = 2.6, 0.9 Hz), 8.70(2H, s). |
| 54 | 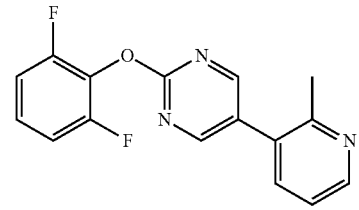 | 1 | NMR2; 2.55(3H, s), 7.00-7.12(2H, m), 7.18-7.30(2H, m), 7.53(1H, dd, J = 7.7, 1.8 Hz), 8.56(2H, s), 8.59(1H, dd, J = 4.9, 1.8 Hz). |
| 55 | 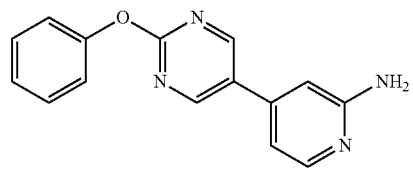 | 1 | NMR2; 4.59(2H, s), 6.61(1H, dd, J = 1.6, 0.8 Hz), 6.80(1H, dd, J = 5.3, 1.6 Hz), 7.19-7.27(2H, m), 7.25-7.34(1H, m), 7.42-7.52(2H, m), 8.17 (1H, dd, J = 5.4, 0.8 Hz), 8.75(2H, s). |
| 56 | 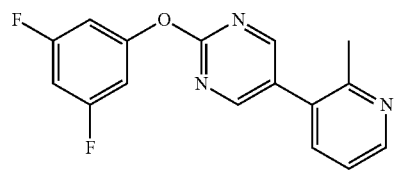 | 1 | NMR2; 2.55(3H, s), 6.76(1H, tt, J = 8.9, 2.3 Hz), 6.80-6.91(2H, m), 7.25-7.34(1H, m), 7.52(1H, dd, J = 7.7, 1.8 Hz), 8.58(2H, s), 8.60(1H, dd, J = 4.9, 1.8 Hz). |

TABLE 2-6-continued

| EX | STR | Prop | DATA |
|---|---|---|---|
| 57 | | 1 | NMR2; 7.11-7.27(4H, m), 7.91-8.06(2H, m), 9.31(2H, s). |
| 58 | | 1 | NMR2; 3.87(2H, s), 7.07(1H, dd, J = 2.7, 1.9 Hz), 7.20-7.34(3H, m), 7.41-7.52(2H, m), 8.16(2H, dd, J = 10.9, 2.3 Hz), 8.72(2H, s). |
| 59 | | 1 | NMR2; 2.36(3H, s), 4.51(2H, s), 5.44(1H, dd, J = 8.3, 0.7 Hz), 7.21-7.33(4H, m), 7.41-7.51(2H, m), 8.49(2H, s). |

TABLE 2-7

| EX | STR | Prop | DATA |
|---|---|---|---|
| 60 | | 60 | NMR2; 7.19-7.36(4H, m), 7.35-7.46(2H, m), 8.26(1H, td, J = 1.8, 5.5 Hz), 8.39-8.45 (1H, m), 8.74(2H, s). |
| 61 | | 60 | NMR2; 6.95-7.08(3H, m), 7.36-7.48(3H, m), 8.27(1H, td, J = 1.7, 5.8 Hz), 8.39-8.45(1H, m), 8.75(2H, s). |
| 62 | | 60 | NMR2; 7.09-7.25(4H, m), 7.35-7.46(2H, m), 8.26(1H, td, J = 1.7, 5.8 Hz), 8.38-5.44(1H, m), 8.74(2H, s). |
| 63 | | 63 | NMR2; 4.21(3H, s), 6.98(1H, ddt, J = 9.2, 7.7, 3.4 Hz), 7.04-7.16(2H, m), 7.19(1H, td, J = 9.4, 5.0 Hz), 7.74(1H, d, J = 9.3 Hz), 9.17(2H, s). |

TABLE 2-7-continued

| EX | STR | Prop | DATA |
|---|---|---|---|
| 64 | | 1 | NMR2; 2.36(3H, s), 4.52(2H, s), 6.44(1H, dd, J = 8.3, 0.7 Hz), 7.19-7.34(4H, m), 7.41-7.51 (2H, m), 8.49(2H, s). |
| 65 | | 63 | NMR2; 4.21(3H, s), 6.90-7.05(2H, m), 7.12(1H, d, J = 9.2 Hz), 7.25-7.34(1H, m), 7.74(1H, d, J = 9.2 Hz), 9.16(2H, s). |
| 66 | | 1 | NMR2; 4.28(2H, s), 4.34(2H, s), 5.02(1H, d, J = 8.0 Hz), 7.13(1H, d, J = 8.0 Hz), 7.19-7.32(3H, m), 7.40-7.51(2H, m), 8.80(2H, s). |
| 67 | | 1 | NMR2; 7.15-7.26(3H, m), 7.45-7.55(1H, m), 7.96(1H, d, J = 6.8 Hz), 8.03(1H, dd, J = 8.9, 0.6 Hz), 9.33(2H, s). |
| 68 | | 63 | NMR2; 4.21(3H, s), 7.06-7.22(4H, m), 7.74(1H, d, J = 9.2 Hz), 9.17(2H, s). |
| 69 | | 69 | NMR2; 1.70(6H, s), 3.75(1H, s), 7.22-7.36(3H, m), 7.41-7.53(2H, m), 7.77-7.88(2H, m), 9.24(2H, s). |

TABLE 2-8

| EX | STR | Prop | DATA |
|---|---|---|---|
| 70 | | 1 | NMR2; 2.50(3H, s), 2.59(3H, s), 7.07-7.14(1H, m), 7.22-7.34(3H, m), 7.40(1H, d, J = 7.6 Hz), 7.42-7.52(2H, m), 8.53(2H, s). |

TABLE 2-8-continued

| EX | STR | Prop | DATA |
|---|---|---|---|
| 71 | | 63 | NMR1; 4.09(3H, s), 7.28(1H, ddd, J = 8.2, 2.3, 1.0 Hz), 7.34-7.44(2H, m), 7.44-7.55(2H, m), 8.26(1H, d, J = 9.3 Hz), 9.29(2H, s). |
| 72 | | 72 | NMR2; 3.15(1H, t, J = 5.5 Hz), 5.07(2H, d, J = 5.5 Hz), 7.21-7.36(3H, m), 7.43-7.53(2H, m), 7.63-7.70(1H, m), 7.84(1H, d, J = 8.8 Hz), 9.24(2H, s). |
| 73 | | 63 | NMR2; 4.21(3H, s), 7.13(1H, d, J = 9.2 Hz), 7.47-7.63(4H, m), 7.75(1H, d, J = 9.2 Hz), 9.18(2H, s). |
| 74 | | 63 | NMR2; 4.21(3H, s), 7.13(1H, d, J = 9.2 Hz), 7.42(1H, ddd, J = 8.3, 4.8, 0.7 Hz), 7.63(1H, ddd, J = 8.3, 2.7, 1.4 Hz), 7.75(1H, d, J = 9.2 Hz), 8.55(1H, dd, J = 4.7, 1.4 Hz), 8.62(1H, d, J = 2.7 Hz), 9.17(2H, s). |
| 75 | | 1 | NMR1; 6.81(2H, s), 7.19(1H, d, J = 5.1 Hz), 7.22-7.34(3H, m), 7.42-7.52(2H, m), 8.36 (1H, d, J = 5.1 Hz), 9.22(2H, s.) |
| 76 | | 1 | NMR2; 2.55(2H, s), 7.23-7.31(1H, m), 7.47(1H, d, J = 7.5 Hz), 7.45-7.64(4H, m), 8.57(2H, s), 8.60(1H, dd, J = 4.9, 1.8 Hz). |
| 77 | | 1 | NMR2; 2.55(3H, s), 7.12-7.21(2H, m), 7.19-7.34(2H, m), 7.44-7.66(2H, m), 8.87(2H, s), 8.59(1H, m). |
| 78 | | 1 | NMR1; 6.08(2H, s), 6.70(1H, dd, J = 1.7, 0.8 Hz), 6.84(1H, dd, J = 5.3, 1.6 Hz), 7.14(2H, tdt, J = 8.1, 2.0, 0.9 Hz), 7.25(1H, dt, J = 10.1, 2.3 Hz), 7.50(1H, td, J = 8.3, 6.8 Hz), 8.01(1H, dd, J = 5.3, 0.7 Hz), 8.94(2H, s). |

TABLE 2-8-continued

| EX | STR | Prop | DATA |
|---|---|---|---|
| 79 | | 1 | NMR1; 6.07(2H, s), 6.70(1H, dd, J = 1.7, 0.8 Hz), 6.83 (1H, dd, J = 6.3, 1.6 Hz), 7.24-7.36(4H, m), 8.00(1H, dd, J = 6.3, 0.8 Hz), 6.92(2H, s). |

TABLE 2-9

| EX | STR | Prop | DATA |
|---|---|---|---|
| 80 | | 1 | NMR1; 6.08(2H, s), 6.70(1H, dd, J = 1.7, 0.8 Hz), 6.84(1H, dd, J = 5.4, 1.6 Hz), 7.25-7.40(2H, m), 7.36-7.49(2H, m), 8.01(1H, dd, J = 5.4, 0.7 Hz), 8.94(2H, s). |
| 81 | | 1 | NMR2: 4.60(2H, s), 6.62(1H, dd, J = 1.6, 0.8 Hz), 6.81(1H, dd, J = 5.4, 1.0 Hz), 7.40-7.47(1H, m), 7.49-7.63(3H, m), 8.19(1H, dd, J = 5.4, 0.8 Hz), 8.78(2H, s). |
| 82 | | 1 | NMR1; 6.09(2H, s), 6.71(1H, dd, J = 1.6, 0.8 Hz), 6.85(1H, dd, J = 5.3, 1.7 Hz), 7.13-7.26(3H, m), 8.02(1H, dd, J = 5.4, 0.7 Hz), 8.97(2H, s) |
| 83 | | 1 | NMR1; 6.08(2H, s), 6.71(1H, s), 6.84(1H, dd, J =5.3, 1.7 Hz), 7.33(2H, dddd, J = 13.9, 8.3, 2.3, 1.1 Hz), 7.40(1H, d, J = 2.8 Hz), 7.60(1H, t, J = 8.3 Hz), 8.01(1H, d, J = 5.2 Hz), 5.95(2H, s). |
| 84 | | 84 | NMR1; 6.23(2H, s), 6.54(1H, dd, J = 8.7, 0.8 Hz), 7.21(1H, ddt, J = 9.2, 6.0, 3.3 Hz), 7.41-7.54(2H, m), 7.76(1H, dd, J = 8.8, 2.6 Hz), 8.30(1H, dd, J = 2.6, 0.8 Hz), 8.90(2H, s). |
| 85 | | 84 | NMR1; 6.22(2H, s), 6.54(1H, dd, J = 8.7, 0.8 Hz), 7.13(1H, dddd, J = 9.2, 3.8, 2.8, 1.8 Hz), 7.46-7.58(2H, m), 7.76(1H, dd, J = 8.6, 2.6 Hz), 8.30(1H, dd, J = 2.6, 0.8 Hz), 8.88(2H, s). |

TABLE 2-9-continued

| EX | STR | Prop | DATA |
|---|---|---|---|
| 86 | | 84 | NMR1; 6.23(2H, s), 6.54 (1H, dd, J = 8.7, 0.8 Hz), 7.12-7.23(1H, m), 7.43-7.55(2H, m), 7.75(1H, dd, J = 8.6, 2.6 Hz), 8.29(1H, dd, J = 2.5, 0.8 Hz), 8.88(2H, s). |
| 87 | | 84 | NMR1; 6.24(2H, s), 6.54(1H, dd, J = 8.6, 0.9 Hz), 7.24-7.37(2H, m), 7.33-7.47(1H, m), 7.76(1H, dd, J = 8.6, 2.6 Hz), 8.30(1H, dd, J = 2.6, 0.8 Hz), 8.90(2H, s). |
| 88 | | 88 | NMR1; 2.33(3H, s), 6.20(2H, s), 6.54(1H, dd, J = 8.6, 0.8 Hz), 6.95-7.06(2H, m), 7.07(1H, ddt, J = 7.6, 1.7, 0.9 Hz), 7.32(1H, t, J = 7.8 Hz), 7.74(1H, dd, J = 8.8, 2.6 Hz), 8.28(1H, dd, J = 2.6, 0.8 Hz), 8.85(2H, s). |

TABLE 2-10

| EX | STR | Prop | DATA |
|---|---|---|---|
| 89 | | 84 | NMR1; 6.23(2H, s), 6.54(1H, dd, J = 8.6, 0.8 Hz), 7.59-7.71(2H, m), 7.76(2H, ddd, J = 6.7, 3.7, 2.1 Hz), 7.85(1H, ddd, J = 2.1, 1.5, 0.7 Hz), 8.30(1H, dd, J = 2.5, 0.8 Hz), 8.90(2H, s). |
| 90 | | 84 | NMR1; 6.23(2H, s), 6.54(1H, dd, J = 8.7, 0.8 Hz), 7.52(1H, ddd, J = 8.4, 4.7, 0.7 Hz), 7.71-7.80(2H, m), 8.30(1H, dd, J = 2.6, 0.8 Hz), 8.45-8.57(2H, m), 8.89(2H, s). |
| 91 | | 91 | NMR2; 7.13(1H, d, J = 9.9 Hz), 7.18-7.27(2H, m), 7.26-7.35(1H, m), 7.42-7.52(2H, m), 7.67(1H, d, J = 9.9 Hz), 8.96(2H, s), 11.60(1H, s) |
| 92 | | 92 | NMR2; 2.62-2.71(2H, m), 2.9-3.00(2H, m), 7.16-7.25(2H, m), 7.24-7.34(1H, m), 7.40-7.51(2H, m), 8.64(1H, s), 8.88(2H, s). |

TABLE 2-10-continued
| EX | STR | Prop | DATA |
|---|---|---|---|
| 93 | | 7 | NMR2; 6.95-7.08(3H, m), 7.15(1H, d, J = 9.9 Hz), 7.36-7.47(1H, m), 7.68(1H, d, J = 9.9 Hz), 8.98(2H, s), 11.81(1H, s). |
| 94 | | 94 | NMR2; 2.62-2.72(2H, m), 2.92-3.01(2H, m), 6.93-7.06(3H, m), 7.41(1H, dt, J = 6.5, 8.3 Hz), 8.61(1H, s), 8.89(2H, s). |
| 95 | | 7 | NMR2; 7.13(1H, d, J = 9.9 Hz), 7.18-7.36(4H, m), 7.66(1H, d, J = 9.9 Hz), 8.96(2H, s), 11.23(1H, s). |
| 96 | | 92 | NMR2; 2.62-2.71(2H, m), 2.91-3.00(2H, m), 7.16-7.34(4H, m), 8.63(1H, s), 8.88(2H, s). |
| 97 | | 7 | NMR2; 7.08-7.24(5H, m), 7.65(1H, d, J = 10.0 Hz), 8.95(2H, s), 10.68(1H, s). |
| 98 | | 92 | NMR2; 2.62-2.71(2H, m), 2.91-3.00(2H, m), 7.07-7.24(4H, m), 8.57 (1H, s), 8.87(2H, s) |
TABLE 2-11
| EX | STR | Prop | DATA |
|---|---|---|---|
| 99 | 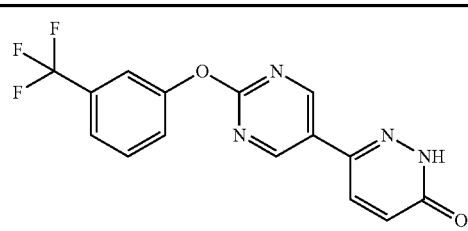 | 7 | NMR2; 7.15(1H, d, J = 9.9 Hz), 7.39-7.64(4H, m), 7.68(1H, d, J = 9.9 Hz), 6.98(2H, s), 11.71(1H, s). |

TABLE 2-11-continued

| EX | STR | Prop | DATA |
|---|---|---|---|
| 100 | | 92 | NMR2; 2.63-2.72(2H, m), 2.92-3.02(2H, m), 7.36-7.63(4H, m), 8.58(1H, s), 8.89(2H, s). |
| 101 | | 7 | NMR1; 7.07(1H, d, J = 9.9 Hz), 7.29-7.46(3H, m), 8.06(1H, d, J = 9.9 Hz), 9.12(2H, s), 13.39(1H, s). |
| 102 | | 7 | NMR1; 7.07(1H, d, J = 9.9 Hz), 7.14-7.25(3H, m), 8.07(1H, d, J = 9.9 Hz), 9.12(2H, s), 13.38(1H, s). |
| 103 | | 7 | NMR2; 6.75(1H, dd, J = 0.7, 9.4 Hz), 7.18-7.33(3H, m), 7.41-7.51(2H, m), 7.58(1H, d, J = 2.6 Hz), 7.67(1H, dd, J = 2.7, 9.6 Hz), 8.62(2H, s), 13.22(1H, s). |
| 104 | | 92 | NMR2; 2.67(2H, dd, J = 7.7 Hz, 8.8 Hz), 2.96(2H, dd, J = 7.7 Hz, 8.8 Hz), 6.99-7.08(2H, m), 7.18-7.26(1H, m), 8.62(1H, brs), 8.88(2Hs, s). |
| 105 | | 92 | NMR2; 2.68(2H, dd, J = 7.8 Hz, 8.9 Hz), 2.97(2H, dd, J = 7.7 Hz, 8.8 Hz), 6.72-6.84(3H, m), 8.66(1H, brs), 8.90(2H, s). |
| 106 | | 2 | NMR2; 2.40(3H, s), 6.75(1H, dd, J = 0.7, 9.4 Hz), 6.98-7.11(2H, m), 7.06-7.14(1H, m), 7.34(1H, t, J = 7.8 Hz), 7.56(1H, dd, J = 0.8, 2.7 Hz), 7.66(1H, dd, J = 2.7, 9.5 Hz), 8.62(2H, s), 12.86(1H, s). |
| 107 | | 2 | NMR2; 6.44(1H, t, J = 6.8 Hz), 7.20-7.33(3H, m), 7.37-7.53(3H, m), 7.64(1H, dd, J = 2.0, 7.0 Hz), 8.95(2H, s), 12.74(1H, s). |

TABLE 2-11-continued

| EX | STR | Prop | DATA |
|---|---|---|---|
| 108 | | 2 | NMR1; 7.06(1H, d, J = 9.9 Hz), 7.23(1H, ddd, J = 12.2, 8.5, 3.3 Hz), 7.43-7.55(2H, m), 8.05(1H, d, J = 10.0 Hz), 9.11(2H, s), 13.38(1H, s). |

TABLE 2-12

| EX | STR | Prop | DATA |
|---|---|---|---|
| 109 | | 2 | NMR1; 7.06(1H, d, J = 9.9 Hz), 7.14-7.25(1H, m), 7.45-7.58(2H, m), 8.05(1H, d, J = 9.9 Hz), 9.09(2H, s), 13.37(1H, s). |
| 110 | | 2 | NMR1; 7.06(1H, d, J = 9.9 Hz), 7.27-7.39(2H, m), 7.43(1H, tdd, J = 9.3, 7.8, 4.5 Hz), 8.06(1H, d, J = 9.9 Hz), 9.12(2H, s), 13.38(1H, s). |
| 111 | | 2 | NMR1; 7.06(1H, d, J = 9.8 Hz), 7.26(1H, ddd, J = 8.2, 2.3, 1.0 Hz), 7.37 (1H, ddd, J = 8.1, 2.0, 1.0 Hz), 7.42-7.54(2H, m), 8.08(1H, d, J = 9.9 Hz), 9.09(2H, s), 13.36(1H, s). |
| 112 | | 2 | NMR1; 7.07(1H, d, J = 9.9 Hz), 7.62-7.73(2H, m), 7.72-7.62(1H, m), 7.86-7.92(1H, m), 8.06(1H, d, J = 9.9 Hz), 9.10(2H, s), 13.37(1H, s). |
| 113 | | 2 | NMR1; 7.06(1H, d, J = 9.9 Hz), 7.53(1H, ddd, J = 8.3, 4.7, 0.7 Hz), 7.78(1H, ddd, J = 8.3, 2.8, 1.4 Hz), 8.06(1H, d, J = 9.9 Hz), 8.51(1H, dd, J = 4.7, 1.4 Hz), 8.57(1H, d, J = 2.5 Hz), 9.10(2H, s), 13.37(1H, s). |
| 114 | | 114 | NMR1; 7.20-7.33(3H, m), 7.42-7.52(2H, m), 7.78(1H, d, J = 4.2 Hz), 8.01(1H, d, J = 4.2 Hz), 9.13(2H, s), 13.39(1H, s). |

TABLE 2-12-continued

| EX | STR | Prop | DATA |
|---|---|---|---|
| 115 | | 114 | NMR1; 7.09-7.20(2H, m), 7.25(1H, td, J = 2.3, 10.1 Hz), 7.45-7.56(1H, m), 7.79(1H, d, J = 4.2 Hz), 8.02(1H, d, J = 4.2 Hz), 9.15(2H, s), 13.40(1H, s). |
| 116 | | 1 | NMR2; 7.08(1H, d, J = 2.2 Hz), 7.18-7.27(2H, m), 7.27-7.37(1H, m), 7.43-7.53(2H, m), 8.02(1H, d, J = 2.2 Hz), 8.79(2H, s), 10.86(1H, s). |
| 117 | | 114 | NMR2; 7.17-7.35(4H, m), 7.40(1H, d, J = 4.1 Hz), 7.91(1H, d, J = 4.1 Hz), 9.07(2H, s), 10.59(1H, s). |

TABLE 2-13

| EX | STR | Prop | DATA |
|---|---|---|---|
| 118 | | 118 | NMR3; 7.23-7.34(3H, m), 7.42-7.52(2H, m), 7.57(1H, d, J = 4.5 Hz), 7.68(1H, ddd, J = 1.3, 6.9 8.4 Hz), 7.86(1H, ddd, J = 1.4, 6.9, 8.4 Hz,), 7.91-7.98 (1H, m), 8.11-8.18(1H, m), 8.80(2, s), 8.94(1H, d, J = 4.5 Hz). |
| 119 | | 119 | NMR2; 7.20-7.35(4H, m), 7.42-7.52(2H, m), 7.66-7.79(3H, m), 8.30(1H, dd, J = 1.9, 1.0 Hz), 8.75(2H, s). |
| 120 | | 1 | NMR2; 7.10-7.18(2H, m), 7.18-7.25(2H, m), 7.31(1H, dd, J = 9.3, 1.9 Hz), 7.66-7.80(3H, m), 8.30(1H, dd, J = 1.9, 1.0 Hz), 8.75(2H, s). |
| 121 | | 1 | NMR2; 7.19-7.38(5H, m), 7.66-7.79(3H, m), 8.30(1H, dd, J = 1.9, 1.0 Hz), 8.75(2H, s). |

TABLE 2-13-continued

| EX | STR | Prop | DATA |
|---|---|---|---|
| 122 | | 1 | NMR2; 6.96-7.09(3H, m), 7.31(1H, dd, J = 9.3, 1.8 Hz), 7.37-7.48(1H, m), 7.67-7.80(3H, m), 8.31(1H, dd, J = 1.9, 1.0 Hz), 8.76(2H, s). |
| 123 | | 123 | NMR2; 7.22-7.35(3H, m), 7.39(1H, d, J = 9.5 Hz), 7.43-7.53(2H, m), 7.85(1H, d, J = 1.2 Hz), 8.03-8.12(2H, m), 9.13(2H, s). |
| 124 | | 1 | NMR2; 7.19-7.37(4H, m), 7.40(1H, d, J = 9.5 Hz), 7.85(1H, d, J = 1.2 Hz), 8.03-8.12(2H, m), 9.13(2H, s). |
| 125 | | 1 | NMR2; 6.97-7.10(3H, m), 7.37-7.49(2H, m), 7.86(1H, d, J = 1.2 Hz), 8.04-8.14(2H, m), 9.15(2H, s). |
| 126 | | 1 | NMR2; 7.12-7.19(2H, m), 7.19-7.25(2H, m), 7.39(1H, d, J = 9.4 Hz), 7.85(1H, d, J = 1.2 Hz), 8.03-8.13(2H, m), 9.13(2H, s). |
| 127 | | 1 | NMR2; 6.98(1H, dd, J = 7.1, 1.8 Hz), 7.20-7.35(3H, m), 7.42-7.62(2H, m), 7.62-7.68(1H, m), 7.72(1H, d, J = 1.2 Hz), 7.77-7.83(1H, m), 8.25(1H, dd, J = 7.1, 1.0 Hz), 8.53 (2H, s). |

TABLE 2-14

| EX | STR | Prop | DATA |
|---|---|---|---|
| 128 | | 1 | NMR2; 7.21-7.28(2H, m), 7.32(1H, ddt, J = 7.9, 7.0, 1.1 Hz), 7.43-7.54(2H, m), 7.67(1H, d, J = 1.4 Hz), 7.92(1H, d, J = 1.4 Hz), 8.61(1H, d, J = 2.5 Hz), 8.71(1H, d, J = 2.5 Hz), 8.78(2H, s). |

TABLE 2-14-continued

| EX | STR | Prop | DATA |
|---|---|---|---|
| 129 | | 1 | NMR2; 7.21-7.28(2H, m), 7.32(1H, ddt, J = 7.6, 5.9, 1.2 Hz), 7.39-7.53(3H, m), 7.95(1H, dt, J = 9.5, 1.0 Hz), 8.30(1H, dd, J = 1.6, 1.1 Hz), 8.77(2H, s), 8.94(1H, d, J = 0.9 Hz). |
| 130 | | 1 | NMR2; 6.99(1H, dd, J = 7.1, 1.9 Hz), 7.18-7.37(4H, m), 7.62-7.68(1H, m), 7.72(1H, d, J = 1.2 Hz), 7.77-7.83(1H, m), 8.25(1H, dd, J = 7.1, 1.0 Hz), 8.63(2H, s). |
| 131 | | 1 | NMR2; 6.95-7.10(4H, m), 7.37-7.45(1H, m), 7.63-7.68(1H, m), 7.73(1H, d, J = 1.2 Hz), 7.81(1H, dt, J = 1.7, 0.8 Hz), 8.26 (1H, dd, J = 7.1, 1.0 Hz), 8.84(2H, s). |
| 132 | | 1 | NMR2; 6.98(1H, dd, J = 7.1, 1.8 Hz), 7.10-7.25(4H, m), 7.63-7.68(1H, m), 7.72(1H, d, J = 1.2 Hz), 7.80(1H, dt, J = 1.9, 0.9 Hz), 8.26(1H, dd, J = 7.1, 1.0 Hz, 8.83(2H, s). |
| 133 | | 1 | NMR2; 7.20-7.35(3H, m), 7.43-7.53(2H, m), 8.21(1H, s), 8.24(1H, d, J = 2.1 Hz), 8.75(1H, d, J = 2.2 Hz), 8.81(2H, s), 11.25(1H, s). |
| 134 | | 1 | NMR2; 6.75(1H, dd, J = 2.4, 0.9 Hz), 7.18(1H, d, J = 7.4 Hz), 7.23-7.36(3H, m), 7.43-7.53(2H, m), 8.18(1H, d, J = 2.4 Hz), 8.77(1H, dd, J = 7.3, 0.9 Hz), 9.25(2H, s). |
| 135 | | 1 | NMR2; 7.18-7.36(4H, m), 7.43-7.53(2H, m), 7.93(1H, dd, J = 1.9, 0.9 Hz), 8.42(1H, s), 8.72(1H, dd, J = 7.1, 0.9 Hz), 8.87(2H, s). |
| 136 | | 1 | NMR2; 6.77(1H, dd, J = 6.9, 1.1 Hz), 7.23-7.37(4H, m), 7.44-7.54(2H, m), 7.55-7.60(1H, m), 7.67-7.75(2H, m), 8.84(2H, s). |

TABLE 2-14-continued

| EX | STR | Prop | DATA |
|---|---|---|---|
| 137 | | 137 | NMR2; 6.82(1H, ddd, J = 3.2, 2.0, 1.0 Hz), 7.21-7.34(3H, m), 7.42-7.52(2H, m), 7.55(1H, dd, J = 3.4, 2.7 Hz), 7.80(1H, dd, J = 2.0, 1.0 Hz), 8.65(1H, d, J = 2.0 Hz), 8.78(1H, d, J = 8.7 Hz), 8.80(2H, s). |

TABLE 2-15

| EX | STR | Prop | DATA |
|---|---|---|---|
| 138 | | 137 | NMR2; 6.66(1H, dd, J = 3.5, 1.8 Hz), 7.17(1H, d, J = 5.0 Hz), 7.24-7.35(3H, m), 7.44-7.54(3H, m), 8.44(1H, d, J = 5.0 Hz), 8.96(2H, s), 10.69(1H, s). |
| 139 | | 139 | NMR1; 7.26-7.35(3H, m), 7.45-7.55(2H, m), 7.66(1H, dd, J = 4.2, 8.4 Hz), 7.73(1H, d, J = 4.4 Hz), 8.40(1H, dd, J = 1.9, 8.4 Hz), 8.90(2H, s), 9.18(1H, dd, J = 1.9, 4.1 Hz), 9.19(1H, d, J = 4.4 Hz). |
| 140 | | 1 | NMR2; 3.99(2H, s), 7.00(1H, s), 7.19(1H, dd, J = 9.2, 1.9 Hz), 7.21-7.34(3H, m), 7.41-7.51(3H, m), 8.09(1H, dd, J = 1.9, 0.9 Hz), 8.71(2H, s). |
| 141 | | 1 | NMR2; 7.23-7.26(2H, m), 7.31(1H, ddt, J = 7.9, 7.0, 1.1 Hz), 7.43-7.53(2H, m), 7.68(1H, dd, J = 9.2, 1.8 Hz), 7.92(1H, dd, J = 9.2, 1.0 Hz), 8.42(1H, s), 8.76-8.81(3H, m). |
| 142 | | 1 | NMR2; 4.03(3H, s), 7.20-7.34(4H, m), 7.40-7.59(2H, m), 7.61-7.71(3H, m), 8.26-8.33(2H, m). |
| 143 | | 139 | NMR1; 7.35-7.36(3H, m), 7.44-7.55(2H, m), 7.84(1H, dd, J = 4.1, 8.5 Hz), 8.41-8.63(2H, m), 8.67(1H, d, J = 8.7 Hz), 9.02(1H, dd, J = 1.6, 4.1 Hz), 9.47(2H, s). |

TABLE 2-15-continued

| EX | STR | Prop | DATA |
|---|---|---|---|
| 144 | | 1 | NMR2; 7.19-7.38(4H, m), 7.89(1H, dd, J = 9.2, 1.8 Hz), 7.92(1H, dd, J = 9.2, 1.0 Hz), 8.42(1H, s), 8.77-8.83(3H, m). |
| 145 | | 1 | NMR2; 6.97-7.10(3H, m), 7.35-7.48(1H, m), 7.69(1H, dd, J = 9.2, 1.8 Hz), 7.93(1H, dd, J = 9.3, 1.0 Hz), 8.43(1H, s), 8.77-8.84(3H, m). |
| 146 | | 1 | NMR2; 7.10-7.25(4H, m), 7.68(1H, dd, J = 9.2, 1.5 Hz), 7.92(1H, dd, J = 9.3, 1.0 Hz), 8.43(1H, s), 8.77-8.81(3H, m). |
| 147 | | 1 | NMR2; 4.00(2H, s), 8.57(1H, dd, J = 6.9, 1.9 Hz), 6.95(1H, s), 7.20-7.34(3H, m), 7.41-7.53(3H, m), 8.00-8.06(1H, m), 8.80(2H, s). |
| 148 | | 1 | NMR2; 7.21-7.34(3H, m), 7.42-7.52(2H, m), 7.77-7.82(1H, m), 7.88(1H, d, J = 1.1 Hz), 8.45(1H, d, J = 1.5 Hz), 9.10(2H, s), 9.20(1H, dd, J = 1.6, 0.7 Hz). |

TABLE 2-16

| EX | STR | Prop | DATA |
|---|---|---|---|
| 149 | | 1 | NMR2; 7.18-7.38(4H, m), 7.77-7.83(1H, m), 7.88(1H, d, J = 1.1 Hz), 8.45(1H, d, J = 1.6 Hz), 9.10(2H, s), 9.20(1H, dd, J = 1.6, 0.7 Hz). |
| 150 | | 1 | NMR2; 6.96-7.10(3H, m), 7.37-7.48(1H, m), 7.81(1H, s), 7.89(1H, d, J = 1.1 Hz), 8.47 (1H, d, J = 1.5 Hz), 9.11(2H, s), 9.17-9.23(1H, m). |

TABLE 2-16-continued

| EX | STR | Prop | DATA |
|---|---|---|---|
| 151 | | 1 | NMR2; 6.60(1H, dd, J = 2.3, 0.9 Hz), 7.21-7.35(4H, m), 7.42-7.52(2H, m), 7.67(1H, dd, J = 9.2, 0.9 Hz), 8.02(1H, d, J = 2.3 Hz), 8.63-8.69(1H, m), 8.77(2H, s). |
| 152 | | 1 | NMR2; 6.60(1H, dd, J = 2.3, 0.9 Hz), 7.20-7.37(5H, m), 7.68(1H, dd, J = 9.2, 1.0 Hz), 8.02(1H, d, J = 2.3 Hz), 8.63-8.69(1H, m), 8.77(2H, s). |
| 153 | | 1 | NMR2; 6.51(1H, dd, J = 2.3, 0.9 Hz), 6.96-7.10(3H, m), 7.26(1H, dd, J = 9.1, 1.7 Hz), 7.37-7.48(1H, m), 7.68(1H, dd, J = 9.2, 1.0 Hz), 6.02(1H, d, J = 2.3 Hz), 8.64-8.70(1H, m), 8.79(2H, s). |
| 154 | | 1 | NMR2; 0.60(1H, dd, J = 2.3, 0.9 Hz), 7.10-7.18(2H, m), 7.18-7.29(3H, m), 7.68(1H, dd, J = 9.1, 1.0 Hz), 8.02(1H, d, J = 2.3 Hz), 8.63-8.89(1H, m), 8.77(2H, s). |
| 155 | | 1 | NMR2; 6.86(1H, dd, J = 9.4, 1.5 Hz), 7.21-7.27(2H, m), 7.27-7.34(1H, m), 7.42-7.53(3H, m), 7.54-7.62(1H, m), 8.05-8.11(1H, m), 8.19-8.24(1H, m), 6.74(2H, s). |
| 156 | | 1 | NMR2; 6.66(1H, dd, J = 9.3, 1.5 Hz), 7.18-7.37(4H, m), 7.48-7.53(1H, m), 7.55-7.62(1H, m), 8.05-8.11(1H, m), 8.19-8.24(1H, m), 8.74(2H, s). |
| 157 | | 1 | NMR2; 6.86(1H, dd, J = 9.4, 1.5 Hz), 6.98-7.09(3H, m), 7.42(1H, dtd, J = 8.8, 6.5, 1.6 Hz), 7.48-7.54(1H, m), 7.55-7.63(1H, m), 8.06-8.12(1H, m), 8.19-8.25(1H, m), 8.76(2H, s) |
| 158 | | 1 | NMR2; 6.85(1H, dd, J = 9.4, 1.5 Hz), 7.11-7.18(2H, m), 7.18-7.24(2H, m), 7.48-7.54(1H, m), 7.59(1H, dt, J = 9.4, 1.0 Hz), 8.05-8.11(1H, m), 8.19-8.24(1H, m), 8.74(2H, s). |

TABLE 2-17
| EX | STR | Prop | DATA |
|---|---|---|---|
| 159 | 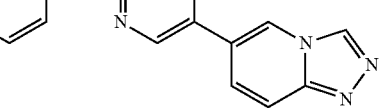 | 1 | NMR2; 4.04(3H, s), 7.20-7.34(3H, m), 7.37-7.51(3H, m), 7.80-7.88(1H, m), 8.29-8.33(1H, m), 6.33(1H, s), 8.85-8.90(1H, m). |
| 160 | 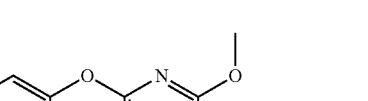 | 1 | NMR2; 4.05(3H, s), 7.22-7.33(3H, m), 7.42-7.48(2H, m), 7.51(1H, d, J = 9.5 Hz), 7.80(1H, d, J = 1.2 Hz), 7.97(1H, dd, J = 9.5, 0.7 Hz), 8.01(1H, dd, J = 1.3, 0.7 Hz), 8.74(1H, s). |
| 161 | 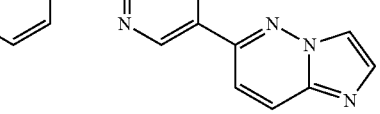 | 1 | NMR2; 2.41(3H, d, J = 0.8 Hz), 7.01-7.08(2H, m), 7.11(1H, ddt, J = 7.5, 1.6, 0.9 Hz), 7.28-7.39(2H, m), 7.67-7.70(1H, m), 7.72(1H, d, J = 1.2 Hz), 7.75(1H, dt, J = 9.4, 0.9 Hz), 8.29(1H, dd, J = 1.9, 1.0 Hz), 8.75(2H, s). |
| 162 | 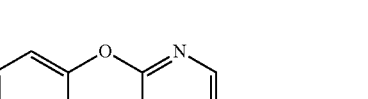 | 1 | NMR2; 3.83(3H, s), 6.78-6.82(1H, m), 6.84(2H, dddd, J = 8.0, 4.2, 2.4, 0.9 Hz), 7.31(1H, dd, J = 9.3, 1.8 Hz), 7.37(1H, t, J = 8.2 Hz), 7.67-7.70(1H, m), 7.72(1H, d, J = 1.3 Hz), 7.76(1H, dt, J = 9.4, 0.9 Hz), 8.30(1H, dd, J = 1.9, 1.0 Hz), 8.75(2H, s). |
| 163 | 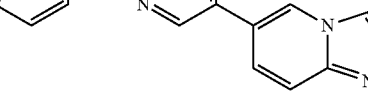 | 163 | NMR2; 7.16(1H, ddd, J = 8.1, 2.2, 1.1 Hz), 7.25-7.35(3H, m), 7.36-7.43(1H, m), 7.68-7.71(1H, m), 7.73(1H, d, J = 1.2 Hz), 7.77(1H, dt, J = 9.3, 0.9 Hz), 8.31(1H, dd, J = 1.9, 1.0 Hz), 8.76(2H, s). |
| 164 | 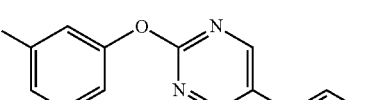 | 163 | NMR2; 7.06-7.23(3H, m), 7.31(1H, dd, J = 9.4, 1.9 Hz), 7.67-7.80(3H, m), 8.29-8.34(1H, m), 8.76(2H, s). |
| 165 |  | 163 | NMR2; 6.91-7.05(2H, m), 7.23-7.35(2H, m), 7.68-7.71(1H, m), 7.72(1H, d, J = 1.3 Hz), 7.76(1H, dt, J = 9.4, 0.9 Hz), 8.30(1H, dd, J = 1.9, 1.0 Hz), 8.74(2H, s). |

TABLE 2-17-continued

| EX | STR | Prop | DATA |
|---|---|---|---|
| 166 | | 163 | NMR2; 6.99(1H, ddt, J = 9.1, 7.7, 8.3 Hz), 7.08(1H, ddd, J = 8.3, 6.1, 3.1 Hz), 7.19(1H, td, J = 9.4, 5.0 Hz), 7.31(1, dd, J = 9.3, 1.9 Hz), 7.68-7.71(1H, m), 7.72(1H, d, J = 1.2 Hz), 7.76(1H, dt, J = 9.3, 0.9 Hz), 8.31(1H, dd, J = 1.9, 1.0 Hz), 8.75(2H, s). |
| 167 | | 163 | NMR2; 7.00-7.12(2H, m), 7.19-7.23(1H, m), 7.31(1H, dd, J = 9.3, 1.8 Hz), 7.68-7.71(1H, m), 7.72(1H, d, J = 1.3 Hz), 7.74-7.79(1H, m), 8.31(1H, dd, J = 1.9, 1.0 Hz), 8.75(2H, s). |

TABLE 2-18

| EX | STR | Prop | DATA |
|---|---|---|---|
| 168 | | 163 | NMR2; 7.00(1H, dddd, J = 9.0, 3.6, 2.8, 1.8 Hz), 7.13(1H, ddd, J = 10.7, 6.7, 2.8 Hz), 7.25(1H, dt, J = 9.6, 8.9 Hz), 7.31(1H, dd, J = 9.4, 1.6 Hz), 7.68-7.72(1H, m), 7.73(1H, d, J = 1.3 Hz), 7.74-7.80(1H, m), 8.31(1H, dd, J = 1.9, 1.0 Hz), 8.76(2H, s). |
| 169 | | 163 | NMR2; 6.76(1H, tt, J = 8.9, 2.3 Hz), 6.80-6.87(2H, m), 7.32(1H, dd, J = 9.3, 1.9 Hz), 7.69-7.72(1H, m), 7.73(1H, d, J = 1.3 Hz), 7.76-7.79(1H, m), 8.32(1H, dd, J = 1.8, 1.0 Hz), 8.78(2H, s). |
| 170 | | 163 | NMR2; 7.32(1H, dd, J = 9.3, 1.9 Hz), 7.41-7.48(1H, m), 7.50-7.64(3H, m), 7.68-7.71(1H, m), 7.73(1H, d, J = 1.3 Hz), 7.74-7.81(1H, m), 8.32(1H, dd, J = 1.8, 1.0 Hz), 8.77(2H, s). |
| 171 | | 163 | NMR2; 7.14-7.19(2H, m), 7.21(1H, ddd, J = 8.3, 2.1, 1.1 Hz), 7.32(1H, dd, J = 9.4, 1.9 Hz), 7.44-7.53(1H, m), 7.68-7.71(1H, m), 7.73(1H, d, J = 1.3 Hz), 7.74-7.79(1H, m), 8.31(1H, dd, J = 1.9, 1.0 Hz), 8.77(2H, s). |
| 172 | | 172 | NMR2; 3.74(2H, s), 7.19-7.33(4H, m), 7.41-7.54(3H, m), 6.12(1H, s), 9.07(2H, s). |

TABLE 2-18-continued

| EX | STR | Prop | DATA |
|---|---|---|---|
| 173 | | 173 | NMR2; 7.21-7.28(2H, m), 7.28-7.36(1H, m), 7.41(1H, dd, J = 9.1, 1.5 Hz), 7.45-7.51(2H, m), 7.88(1H, dd, J = 9.2, 1.0 Hz), 8.14(1H, d, J = 1.0 Hz), 8.82(2H, s), 8.88-8.94(1H, m). |
| 174 | | 1 | NMR2; 7.20-7.38(4H, m), 7.41(1H, dd, J = 9.2, 1.5 Hz), 7.88(1H, dd, J = 9.2, 1.1 Hz), 6.14(1H, d, J = 1.1 Hz), 8.82(2H, s), 8.92(1H, q, J = 1.1 Hz). |
| 175 | | 1 | NMR2; 6.97-7.10(3H, m), 7.38-7.49(2H, m), 7.89(1H, dd, J = 9.2, 1.1 Hz), 8.15(1H, d, J = 1.0 Hz), 8.83(2H, s), 8.93(1H, q, J = 1.1 Hz). |
| 176 | | 1 | NMR2; 7.10-7.27(4H, m), 7.41(1H, dd, J = 9.1, 1.5 Hz), 7.88(1H, dd, J = 9.2, 1.0 Hz), 8.15(1H, d, J = 1.0 Hz), 8.82(2H, s), 8.92(1H, q, J = 1.1 Hz). |
| 177 | | 1 | NMR2; 2.49(3H, d, J = 0.9 Hz), 7.20-7.34(4H, m), 7.41-7.52(3H, m), 7.63(1H, dt, J = 9.3, 0.9 Hz), 8.19(1H, dd, J = 1.9, 1.0 Hz), 8.73(2H, s). |

TABLE 2-19

| EX | STR | Prop | DATA |
|---|---|---|---|
| 178 | | 1 | NMR2; 2.49(3H, d, J = 0.9 Hz), 7.18-7.37(5H, m), 7.41-7.48(1H, m), 7.59-7.67(1H, m), 8.20(1H, dd, J = 1.9, 1.0 Hz), 8.73(2H, s). |
| 179 | | 1 | NMR2; 2.49(3H, d, J = 0.9 Hz), 6.96-7.09(3H, m), 7.26(1H, dd, J = 9.3, 1.8 Hz), 7.36-7.47(2H, m), 7.60-7.68(1H, m), 6.20(1H, dd, J = 1.9, 1.0 Hz), 8.74(2H, s). |

TABLE 2-19-continued
| EX | STR | Prop | DATA |
|---|---|---|---|
| 180 | 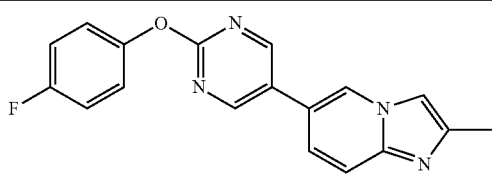 | 1 | NMR2; 2.49(3H, d, J = 0.9 Hz), 7.09-7.28(6H, m), 7.41-7.46(1H, m), 7.59-7.67(1H, m), 8.19(1H, dd, J = 1.8, 1.0 Hz), 8.73(2H, s). |
| 181 | 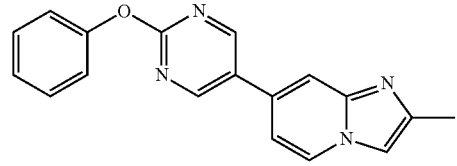 | 1 | NMR2; 2.49(3H, d, J = 0.9 Hz), 6.92(1H, dd, J = 7.0, 1.9 Hz), 7.20-7.33(3H, m), 7.37-7.42(1H, m), 7.43-7.51(2H, m), 7.64-7.70(1H, m), 8.14(1H, dd, J = 7.0, 0.9 Hz), 8.81(2H, s). |
| 182 | 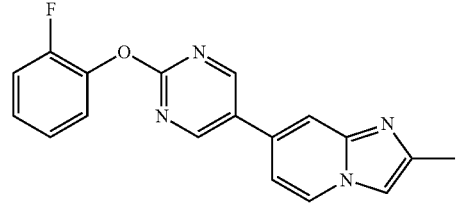 | 1 | NMR2; 2.49(3H, d, J = 0.9 Hz), 6.92(1H, dd, J = 7.0, 1.8 Hz), 7.18-7.37(4H, m), 7.37-7.42(1H, m), 7.64-7.70(1H, m), 8.14(1H, dd, J = 7.0, 0.9 Hz), 8.81(2H, s). |
| 183 | 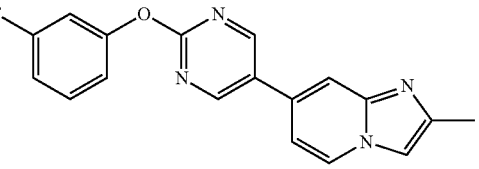 | 1 | NMR2; 2.49(3H, d, J = 0.9 Hz), 6.92(1H, dd, J = 7.0, 1.9 Hz), 6.95-7.09(3H, m), 7.36-7.47(2H, m), 7.65-7.70(1H, m), 8.15(1H, dd, J = 7.0, 1.0 Hz), 8.62(2H, s). |
| 184 | 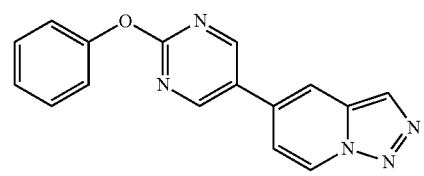 | 1 | NMR2; 7.15(1H, dd, J = 7.3, 1.9 Hz), 7.20-7.29(2H, m), 7.31(1H, ddt, J = 7.8, 6.9, 1.1 Hz), 7.43-7.53(2H, m), 7.87(1H, dd, J = 1.9, 1.0 Hz), 8.17(1H, d, J = 1.0 Hz), 8.82-8.90(3H, m). |
| 185 | 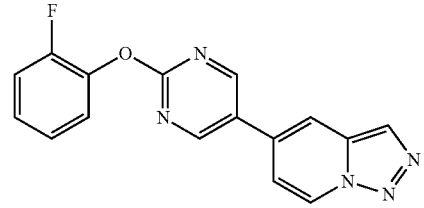 | 1 | NMR2; 7.16(1H, dd, J = 7.3, 1.9 Hz), 7.19-7.37(4H, m), 7.88(1H, dd, J = 1.9, 1.0 Hz), 8.17(1H, d, J = 1.0 Hz), 6.84(2H, s), 8.86(1H, dt, J = 7.3, 1.0 Hz). |
| 186 | 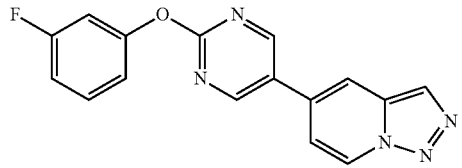 | 1 | NMR2; 6.97-7.10(3H, m), 7.16(1H, dd, J = 7.3, 1.9 Hz), 7.43(1H, tdd, J = 8.2, 6.5, 0.6 Hz), 7.89(1H, dd, J = 1.9, 1.0 Hz), 8.18(1H, d, J = 1.0 Hz), 8.53-8.91(3H, m). |
| 187 | 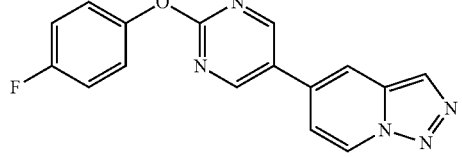 | 1 | NMR2; 7.10-7.26(5H, m), 7.88(1H, dd, J = 1.9, 1.0 Hz), 8.17(1H, d, J = 1.0 Hz), 8.81-8.90(3H, m). |

TABLE 2-20

| EX | STR | Prop | DATA |
|---|---|---|---|
| 188 | | 1 | NMR2; 7.21-7.28(2H, m), 7.33(1H, ddt, J = 7.9, 7.0, 1.1 Hz), 7.44-7.54(2H, m), 8.61(1H, s), 8.82(2H, s), 8.98-9.05(2H, m). |
| 189 | | 1 | NMR2; 6.97-7.10(3H, m), 7.44(1H, td, J = 8.2, 6.5 Hz), 8.61(1H, s), 8.83(2H, s), 9.00-9.05(2H, m). |
| 190 | | 1 | NMR2; 2.54(3H, d, J = 1.0 Hz), 7.21-7.35(4H, m), 7.42-7.52(3H, m), 7.73(1H, dd, J = 9.3, 1.0 Hz), 7.99(1H, dd, J = 1.9, 1.0 Hz), 8.77(2H, s). |
| 191 | | 1 | NMR2; 2.54(3H, d, J = 0.9 Hz), 7.19-7.37(6H, m), 7.47-7.52(1H, m), 7.73(1H, dd, J = 9.3, 1.0 Hz), 7.99(1H, dd, J = 1.8, 1.0 Hz), 8.77(2H, s). |
| 192 | | 1 | NMR2; 2.54(3H, s), 6.96-7.09(3H, m), 7.29(1H, dd, J = 9.3, 1.7 Hz), 7.42(1H, dddd, J = 9.4, 6.0, 6.2, 1.6 Hz), 7.50(1H, s), 7.74(1H, d, J = 9.4 Hz), 7.97-8.03(1H, m), 8.76-8.81(2H, m). |
| 193 | | 1 | NMR2; 2.54(3H, d, J = 1.0 Hz), 7.10-7.18(2H, m), 7.18-7.25(2H, m), 7.29(1H, dd, J = 9.3, 1.8 Hz), 7.50(1H, s), 7.73(1H, dd, J = 9.3, 1.0 Hz), 7.99(1H, dd, J = 1.8, 1.0 Hz), 8.77(2H, s). |
| 194 | | 1 | NMR2; 6.63(1H, dd, J = 2.3, 0.9 Hz), 6.91(1H, dd, J = 7.3, 2.0 Hz), 7.22-7.27(2H, m), 7.28-7.35(1H, m), 7.42-7.52(2H, m), 7.69(1H, dd, J = 2.0, 1.0 Hz), 8.02(1H, d, J = 2.3 Hz), 8.58(1H, dt, J = 7.3, 1.0 Hz), 8.82(2H, s). |
| 195 | | 1 | NMR2; 6.63(1H, dd, J = 2.3, 0.9 Hz), 6.91(1H, dd, J = 7.3, 2.0 Hz), 7.18-7.37(4H, m), 7.70(1H, dd, J = 2.1, 0.9 Hz), 8.02(1H, d, J = 2.3 Hz), 8.58(1H, dt, J = 7.3, 0.9 Hz), 8.81(2H, s). |

TABLE 2-20-continued

| EX | STR | Prop | DATA |
|---|---|---|---|
| 196 | | 1 | NMR2; 6.64(1H, dd, J = 2.3, 0.9 Hz), 6.92(1H, dd, J = 7.3, 2.1 Hz), 6.95-7.10(3H, m), 7.37-7.46(1H, m), 7.70(1H, dd, J = 2.1, 1.0 Hz), 8.02(1H, d, J = 2.3 Hz), 8.59(1H, dt, J = 7.3, 0.9 Hz), 8.83(2H, s). |
| 197 | | 1 | NMR2; 6.63(1H, dd, J = 2.3, 0.9 Hz), 6.91(1H, dd, J = 7.3, 2.0 Hz), 7.10-7.18(2H, m), 7.18-7.25(2H, m), 7.69(1H, dd, J = 2.1, 1.0 Hz), 8.02(1H, d, J = 2.3 Hz), 8.58(1H, dt, J = 7.3, 0.9 Hz), 8.82(2H, s). |

TABLE 2-21

| EX | STR | Prop | DATA |
|---|---|---|---|
| 198 | HCl | 198 | NMR1; 2.75(3H, s), 7.24-7.35(3H, m), 7.44-7.54(2H, m), 7.97-8.06(2H, m), 8.41(1H, d, J = 2.2 Hz), 8.52(1H, dd, J = 2.3, 0.7 Hz), 8.85(2H, s), 15.13(1H, s). |
| 199 | HCl | 198 | NMR1; 2.73(3H, s), 7.27-7.52(4H, m), 5.01(2H, s), 8.35-8.41(1H, m), 8.51(1H, d, J = 2.2 Hz), 5.84(2H, s), 14.98(1H, s). |
| 200 | HCl | 198 | NMR1; 2.75(3H, s), 7.12-7.22(2H, m), 7.28(1H, dt, J = 10.1, 2.3 Hz), 7.53(1H, td, J = 8.3, 6.8 Hz), 7.93-8.08(2H, m), 8.41(1H, d, J = 2.2 Hz), 8.50-8.56(1H, m), 8.83(2H, s), 15.14(1H, s). |
| 201 | | 1 | NMR2; 2.58(3H, s), 7.08-7.19(3H, m), 7.20-7.28(2H, m), 7.55-7.61(1H, m), 7.63-7.70(1H, m), 7.78(1H, d, J = 1.3 Hz), 8.58(2H, s). |
| 202 | HCl | 198 | NMR1; 2.49(3H, s), 2.57(3H, d, J = 0.9 Hz), 7.28-7.51(4H, m), 8.04(1H, dd, J = 9.3, 0.9 Hz), 8.27(1H, dd, J = 9.3, 1.7 Hz), 9.08-9.12(1H, m), 9.18(2H, s), 14.92(1H, s). |

TABLE 2-21-continued
| EX | STR | Prop | DATA |
|---|---|---|---|
| 203 | 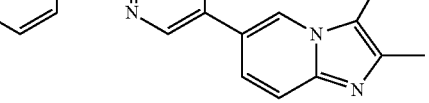 | 1 | NMR2; 2.458(3H, s), 2.463(3H, s), 7.09-7.27(5H, m), 7.63(1H, dd, J = 9.2, 1.0 Hz), 7.90(1H, dd, J = 1.8, 1.0 Hz), 8.76(2H, s). |
| 204 | 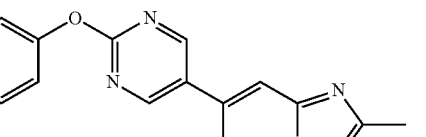 | 1 | NMR2; 2.45(3H, s), 2.46(3H, s), 6.98(1H, dd, J = 7.1, 1.9 Hz), 7.20-7.34(3H, m), 7.41-7.52(2H, m), 7.67(1H, dd, J = 1.9, 0.9 Hz), 7.90(1H, dd, J = 7.1, 0.9 Hz), 8.82(2H, s). |
| 205 | 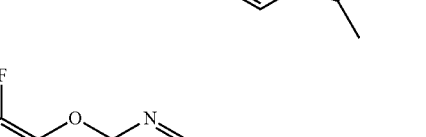 | 1 | NMR2; 2.45(3H, s), 2.46(3H, s), 6.98(1H, dd, J = 7.1, 1.9 Hz), 7.19-7.37(4H, m), 7.67(1H, dd, J = 1.9, 0.9 Hz), 7.90(1H, dd, J = 7.1, 0.9 Hz), 8.82(2H, s). |
| 206 | 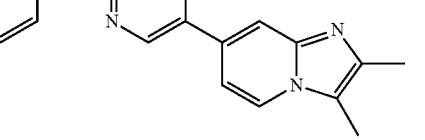 | 1 | NMR2; 2.45(3H, s), 2.46(3H, s), 6.95-7.09(4H, m), 7.36-7.47(1H, m), 7.88(1H, dd, J = 1.9, 0.9 Hz), 7.91(1H, dd, J = 7.1, 1.0 Hz), 8.83(2H, s). |
| 207 | 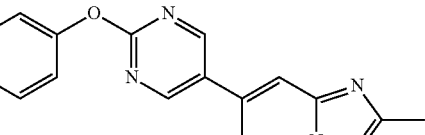 | 1 | NMR2; 2.45(3H, s), 2.46(3H, s), 6.95(1H, dd, J = 7.1, 1.9 Hz), 7.10-7.18(2H, m), 7.18-7.26(2H, m), 7.67(1H, dd, J = 1.9, 0.9 Hz), 7.91(1H, dd, J = 7.2, 1.0 Hz), 5.81(2H, s). |
TABLE 2-22
| EX | STR | Prop | DATA |
|---|---|---|---|
| 208 | 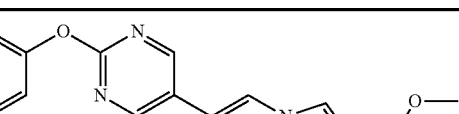 | 1 | NMR2; 3.51(3H, s), 4.68(2H, d, J = 0.8 Hz), 7.20-7.34(4H, m), 7.42-7.52(2H, m), 7.63-7.73(2H, m), 8.24(1H, dd, J = 1.8, 1.0 Hz), 8.74(2H, s). |
| 209 | 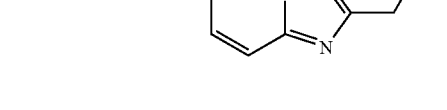 | 1 | NMR2; 3.51(3H, s), 4.68(2H, s), 7.18-7.37(5H, m), 7.64-7.73(2H, m), 8.25(1H, dd, J = 1.9, 1.0 Hz), 8.74(2H, s). |

TABLE 2-22-continued
| EX | STR | Prop | DATA |
|---|---|---|---|
| 210 | 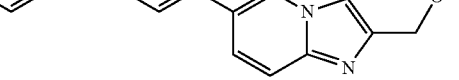 | 1 | NMR2; 3.51(3H, s), 4.68(2H, d, J = 0.8 Hz), 6.96-7.09(3H, m), 7.30(1H, dd, J = 9.3, 1.8 Hz), 7.38-7.48(1H, m), 7.64-7.74(2H, m), 8.26(1H, dd, J = 1.9, 1.0 Hz), 8.76(2H, s). |
| 211 | 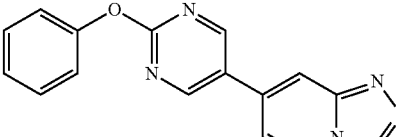 | 1 | NMR2; 7.07(1H, dd, J = 7.2, 1.7 Hz), 7.20-7.28(2H, m), 7.31(1H, ddt, J = 7.9, 7.0, 1.1 Hz), 7.43-7.53(2H, m), 7.95(1H, dt, J = 1.8, 1.0 Hz), 8.25(1H, dd, J = 7.2, 1.1 Hz), 6.85(2H, s), 8.89(1H, d, J = 0.9 Hz). |
| 212 | 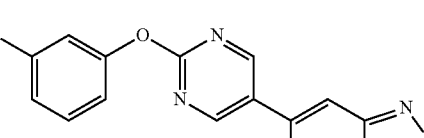 | 1 | NMR2; 6.96-7.11(4H, m), 7.43(1H, tdd, J = 8.2, 6.5, 0.6 Hz), 7.97(1H, dt, J = 1.9, 1.0 Hz), 8.28(1H, dd, J = 7.2, 1.1 Hz), 8.87(2H, s), 8.89(1H, d, J = 0.9 Hz). |
| 213 | 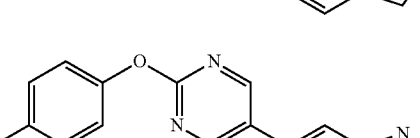 | 1 | NMR2; 7.07(1H, dd, J = 7.2, 1.7 Hz), 7.10-7.25(4H, m), 7.96(1H, dt, J = 1.9, 1.0 Hz), 8.27(1H, dd, J = 7.2, 1.1 Hz), 8.85(2H, s), 8.89(1H, d, J = 0.9 Hz). |
| 214 | 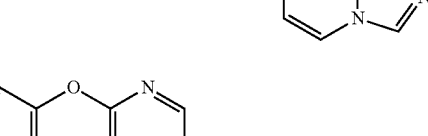 | 1 | NMR2; 7.21-7.28(2H, m), 7.28-7.35(1H, m), 7.41-7.54(3H, m), 7.78-7.86(1H, m), 7.96-8.02(1H, m), 8.30(1H, dd, J = 1.8, 1.0 Hz), 8.75(2H, s). |
| 215 | 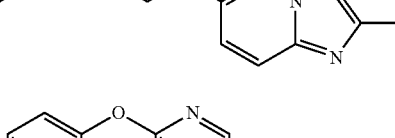 | 1 | NMR2; 3.93(3H, s), 6.48(1H, d, J = 3.4 Hz), 7.21-7.33(4H, m), 7.41-7.51(3H, m), 7.98(1H, d, J = 8.1 Hz), 9.25(2H, s). |
| 216 | 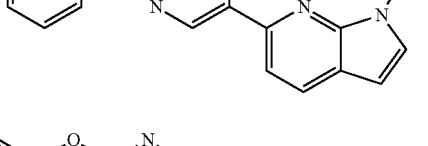 | 1 | NMR2; 7.12(1H, dd, J = 7.1, 1.8 Hz), 7.21-7.27(2H, m), 7.31(1H, ddt, J = 7.9, 7.0, 1.2 Hz), 7.43-7.53(2H, m), 7.81-7.87(1H, m), 7.92-7.98(1H, m), 8.28(1H, dd, J = 7.1, 1.0 Hz), 8.83(2H, s). |
| 217 | 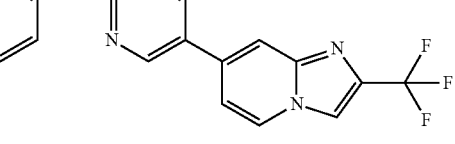 | 1 | NMR2; 7.12(1H, dd, J = 7.2, 1.9 Hz), 7.19-7.37(4H, m), 7.82-7.87(1H, m), 7.92-7.96(1H, m), 8.28(1H, dd, J = 7.2, 1.0 Hz), 8.83(2H, s). |

TABLE 2-23
| EX | STR | Prop | DATA |
|---|---|---|---|
| 218 | 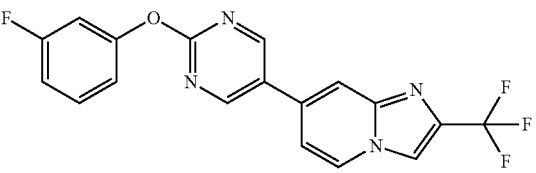 | 1 | NMR2; 6.96-7.09 (3H, m), 7.12 (1H, dd, J = 7.1, 1.8 Hz), 7.43 (1H, tdd, J = 8.2, 6.5, 0.7 Hz), 7.82-7.88 (1H, m), 7.93-7.99 (1H, m), 8.29 (1H, dd, J = 7.1, 1.0 Hz), 8.84 (2H, s). |
| 219 | 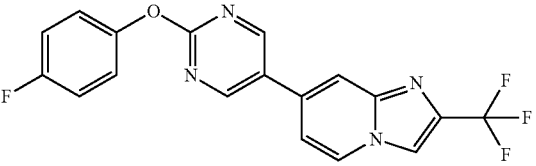 | 1 | NMR2; 7.08-7.26 (5H, m), 7.81-7.87 (1H, m), 7.92-7.98 (1H, m), 8.28 (1H, dd, J = 7.1, 1.0 Hz), 8.83 (2H, s). |
| 220 | 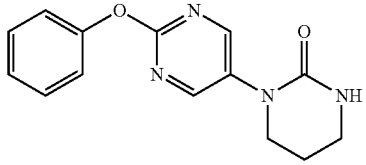 | 220 | NMR2; 2.09-2.20 (2H, m), 3.43-3.51 (2H, m), 3.66-3.74 (2H, m), 5.03 (1H, s), 7.15-7.30 (3H, m), 7.38-7.48 (2H, m), 8.55 (2H, s). |
| 221 | 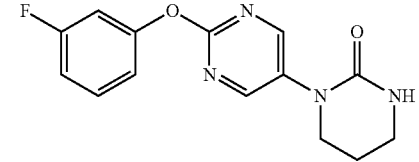 | 221 | NMR2; 2.10-2.21 (2H, m), 3.43-3.51 (2H, m), 3.68-3.75 (2H, m), 5.15 (1H, s), 6.91-7.04 (3H, m), 7.32-7.43 (1H, m), 8.57 (2H, s). |
| 222 | 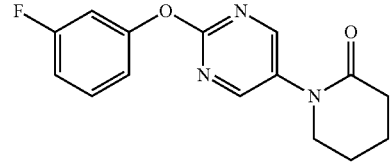 | 220 | NMR2; 1.92-2.07 (4H, m), 2.55-2.64 (2H, m), 3.63-3.72 (2H, m), 6.92-7.05 (3H, m), 7.33-7.44 (1H, m), 8.53 (2H, s). |
| 223 | 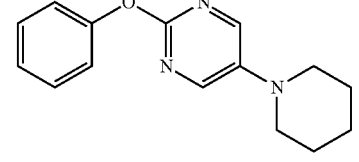 | 223 | NMR2; 1.55-1.63 (2H, m), 1.69-1.78 (4H, m), 3.05-3.13 (4H, m), 7.13-7.25 (3H, m), 7.35-7.45 (2H, m), 8.21 (2H, s). |
| 224 | 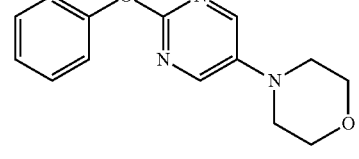 | 223 | NMR2; 3.07-3.15 (4H, m), 3.84-3.91 (4H, m), 7.14-7.27 (3H, m), 7.36-7.46 (2H, m), 8.21 (2H, s). |
| 225 | 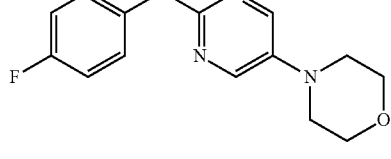 | 223 | NMR2; 3.08-3.15 (4H, m), 3.84-3.91 (4H, m), 7.03-7.19 (4H, m), 8.20 (2H, s). |
| 226 | 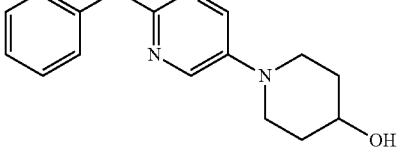 | 226 | NMR2; 1.54-1.64 (1H, m), 1.73 (2H, dtd, J = 12.8, 8.9, 3.9 Hz), 1.97-2.09 (2H, m), 2.94 (2H, ddd, J = 12.4, 9.3, 3.3 Hz), 3.38-3.49 (2H, m), 3.83-3.95 (1H, m), 7.13-7.26 (3H, m), 7.36-7.46 (2H, m), 8.23 (2H, s). |

TABLE 2-23-continued

| EX | STR | Prop | DATA |
|---|---|---|---|
| 227 | | 226 | NMR2; 1.53 (1H, d, J = 4.2 Hz), 1.73 (2H, dtd, J = 12.8, 8.8, 3.9 Hz), 1.98-2.09 (2H, m), 2.96 (2H, ddd, J = 12.4, 9.2, 3.3 Hz), 3.40-3.51 (2H, m), 3.85-3.97 (1H, m), 6.87-7.01 (3H, m), 7.29-7.41 (1H, m), 8.24 (2H, s). |

TABLE 2-24

| EX | STR | Prop | DATA |
|---|---|---|---|
| 228 | | 226 | NMR2; 1.54 (1H, d, J = 4.2 Hz), 1.66-1.80 (2H, m), 1.97-2.09 (2H, m), 2.94 (2H, ddd, J = 12.4, 9.2, 3.3 Hz), 3.38-3.49 (2H, m), 3.84-3.96 (1H, m), 7.03-7.19 (4H, m), 8.22 (2H, s). |
| 229 | | 229 | NMR2; 3.75-3.83 (2H, m), 4.03-4.11 (2H, m), 4.37 (2H, s), 7.16-7.24 (2H, m), 7.24-7.32 (1H, m), 7.39-7.50 (2H, m), 8.61 (2H, s). |
| 230 | | 229 | NMR2; 3.76-3.84 (2H, m), 4.04-4.12 (2H, m), 4.37 (2H, s), 6.92-7.05 (3H, m), 7.34-7.45 (1H, m), 8.63 (2H, s). |
| 231 | | 229 | NMR2; 3.75-3.83 (2H, m), 4.04-4.11 (2H, m), 4.37 (2H, s), 7.06-7.22 (4H, m), 8.61 (2H, s). |
| 232 | | 229 | NMR2; 2.92-3.00 (2H, m), 3.83-3.89 (2H, m), 3.89-3.97 (4H, m), 7.17-7.23 (2H, m), 7.23-7.30 (1H, m), 7.39-7.48 (2H, m), 8.43 (2H, s). |
| 233 | | 229 | NMR2; 2.93-3.00 (2H, m), 3.84-3.97 (6H, m), 6.92-7.05 (3H, m), 7.34-7.44 (1H, m), 8.45 (2H, s). |

TABLE 2-24-continued

| EX | STR | Prop | DATA |
|---|---|---|---|
| 234 | | 229 | NMR2; 2.92-3.00 (2H, m), 3.83-3.90 (2H, m), 3.90-3.97 (4H, m), 7.06-7.21 (4H, m), 8.43 (2H, s). |
| 235 | (chiral) | 226 | NMR2; 1.76-1.82 (1H, m), 2.02-2.24 (2H, m), 2.63 (1H, ddd, J = 17.7, 5.3, 1.6 Hz), 2.86 (1H, ddd, J = 17.7, 4.6, 1.1 Hz), 3.58 (1H, dt, J = 11.5, 5.5 Hz), 3.94 (1H, ddd, J = 11.7, 8.7, 4.8 Hz), 4.36-4.45 (1H, m), 7.16-7.31 (3H, m), 7.39-7.49 (2H, m), 8.52 (2H, s). |
| 236 | | 7 | NMR2; 6.03 (2H, s), 6.89-6.94 (1H, m), 6.95-6.99 (2H, m), 7.19-7.32 (3H, m), 7.40-7.50 (2H, m), 8.67 (2H, s). |
| 237 | | 7 | NMR2; 7.21-7.35 (3H, m), 7.43-7.51 (2H, m), 7.60-7.66 (1H, m), 7.70-7.78 (2H, m), 7.78-7.82 (1H, m), 8.75 (2H, s). |

TABLE 2-25

| EX | STR | Prop | DATA |
|---|---|---|---|
| 238 | | 1 | NMR2; 2.87 (3H, s), 7.21-7.33 (3H, m), 7.42-7.54 (3H, m), 7.91-7.96 (1H, m), 8.06-8.12 (1H, m), 8.82 (2H, s). |
| 239 | | 239 | NMR2; 3.86 (2H, s), 6.77-6.85 (2H, m), 7.22-7.39 (5H, m), 7.43-7.52 (2H, m), 8.71 (2H, s). |
| 240 | | 240 | NMR2; 3.98 (2H, s), 6.84 (1H, dd, J = 8.6, 0.8 Hz), 7.00 (1H, dd, J = 8.5, 0.7 Hz), 7.05-7.19 (4H, m), 7.72 (1H, dd, J = 8.6, 2.6 Hz), 7.83 (1H, dd, J = 8.5, 2.6 Hz), 8.30-8.35 (2H, m). |

TABLE 2-25-continued

| EX | STR | Prop | DATA |
|---|---|---|---|
| 241 | | 1 | NMR2; 7.22-7.34 (3H, m), 7.42-7.53 (2H, m), 7.57-7.65 (1H, m), 8.09 (1H, dd, J = 8.3, 0.6 Hz), 8.30 (1H, dd, J = 1.8, 0.6 Hz), 8.85 (2H, s), 9.08 (1H, s). |
| 242 | | 1 | NMR2; 7.19-7.34 (3H, m), 7.42-7.52 (2H, m), 7.67 (1H, dd, J = 8.5, 1.9 Hz), 8.10 (1H, dd, J = 1.8, 0.6 Hz), 8.25 (1H, dd, J = 8.5, 0.6 Hz), 8.82 (2H, s), 9.06 (1H, s). |
| 243 | | 7 | NMR1; 7.21-7.33 (3H, m), 7.42-7.52 (3H, m), 7.81-7.88 (2H, m), 7.95-8.03 (2H, m), 8.06 (1H, s), 9.04 (2H, s). |
| 244 | | 1 | NMR2; 7.24-7.35 (3H, m), 7.43-7.53 (3H, m), 7.73 (1H, dd, J = 1.9, 8.4 Hz), 7.96 (1H, d, J = 8.4 Hz), 8.18-8.26 (1H, m), 8.26-8.31 (1H, m), 8.93 (2H, s), 8.98 (1H, dd, J = 1.8, 4.3 Hz). |
| 245 | | 7 | NMR2; 2.65-2.74 (2H, m), 3.01-3.10 (2H, m), 6.86 (1H, d, J = 8.7 Hz), 7.22-7.35 (5H, m), 7.41-7.51 (2H, m), 7.62 (1H, s), 8.71 (2H, s). |
| 246 | | 7 | NMR2; 2.64-2.73 (2H, m), 3.03 (2H, t, J = 7.5 Hz), 6.86 (1H, s), 7.13 (1H, dd, J = 1.8, 7.7 Hz), 7.19-7.34 (3H, m), 7.41-7.51 (2H, m), 7.83-7.96 (1H, m), 8.71 (2H, s). |
| 247 | | 7 | NMR2; 3.09 (2H, t, J = 6.6 Hz), 3.63 (2H, td, J = 2.9, 6.5 Hz), 5.93 (1H, s), 7.19-7.34 (3H, m), 7.34-7.40 (1H, m), 7.42-7.55 (3H, m). 8.19 (1H, d, J = 8.0 Hz), 8.78 (2H, s). |

TABLE 2-26
| EX | STR | Prop | DATA |
|---|---|---|---|
| 248 | 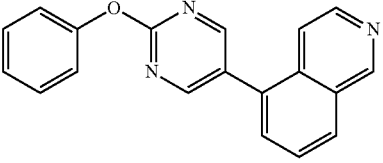 | 1 | NMR2; 7.26-7.36 (3H, m), 7.44-7.54 (2H, m), 7.61 (1H, dt, J = 1.0, 6.0 Hz), 7.66 (1H, dd, J = 1.3, 7.1 Hz), 7.72 (1H, dd, J = 7.1, 8.1 Hz), 8.09 (1H, dt, J = 1.2, 8.1 Hz), 8.57 (1H, d, J = 6.0 Hz), 8.70 (2H, s), 9.36 (1H, d, J = 1.0 Hz). |
| 249 | 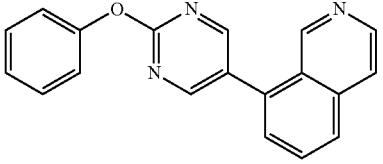 | 1 | NMR2; 7.27-7.36 (3H, m), 7.44-7.55 (3H, m), 7.72-7.83 (2H, m), 7.93 (1H, dt, J = 1.1, 8.4 Hz), 8.63 (1H, d, J = 5.7 Hz), 8.73 (2H, s), 9.21-9.27 (1H, m). |
| 250 | 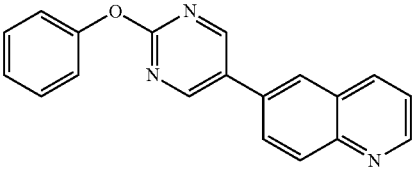 | 1 | NMR2; 7.23-7.35 (3H, m), 7.43-7.53 (3H, m), 7.88 (1H, dd, J = 2.1, 8.7 Hz), 7.96 (1H, d, J = 2.2 Hz), 8.21-8.31 (2H, m), 8.89 (2H, s), 8.97 (1H, dd, J = 1.7, 4.2 Hz). |
| 251 | 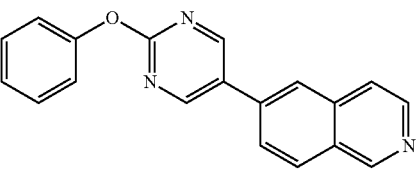 | 1 | NMR2; 7.22-7.35 (3H, m), 7.43-7.56 (2H, m), 7.73 (1H, dt, J = 1.0, 5.9 Hz), 7.77 (1H, dd, J = 1.8, 8.5 Hz), 7.94-7.99 (1H, m), 8.12 (1H, dt, J = 0.8, 8.5 Hz), 8.61 (1H, d, J = 5.8 Hz), 8.89 (2H, s), 9.29-9.35 (1H, m). |
| 252 | 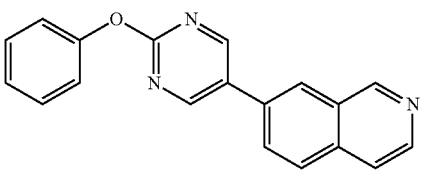 | 1 | NMR2; 7.22-7.35 (3H, m), 7.43-7.55 (2H, m), 7.71 (1H, dt, J = 1.0, 5.8 Hz), 7.86 (1H, dd, J = 1.9, 8.5 Hz), 7.97 (1H, d, J = 8.4 Hz), 8.09-8.14 (1H, m), 8.59 (1H, d, J = 5.7 Hz), 8.89 (2H, s), 9.32-9.38 (1H, m). |
| 253 | 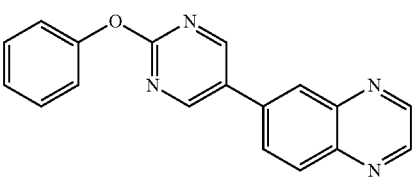 | 1 | NMR2; 7.23-7.36 (3H, m), 7.44-7.54 (2H, m), 7.96 (1H, dd, J = 2.1, 8.7 Hz), 8.22-8.31 (2H, m), 8.89-8.92 (2H, m), 8.94 (2H, s). |
| 254 | 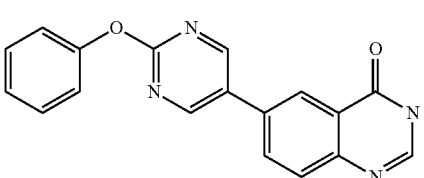 | 1 | NMR2; 7.22-7.35 (3H, m), 7.43-7.53 (2H, m), 7.91 (1H, d, J = 8.5 Hz), 7.97 (1H, dd, J = 2.2, 8.5 Hz), 8.14 (1H, s), 8.45-8.51 (1H, m), 8.88 (2H, s), 11.11 (1H, s). |
| 255 | 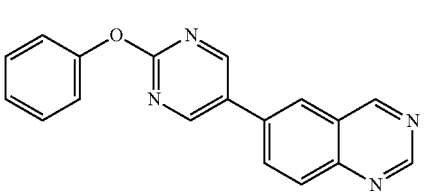 | 1 | NMR2; 7.24-7.35 (3H, m), 7.44-7.53 (2H, m), 8.06-8.13 (2H, m), 8.18-8.24 (1H, m), 8.89 (2H, s), 9.39 (1H, s), 9.49-9.53 (1H, m). |

TABLE 2-26-continued

| EX | STR | Prop | DATA |
|---|---|---|---|
| 256 | | 139 | NMR1; 7.22-7.32 (3H, m), 7.41 (1H, d, J = 8.5 Hz), 7.44-7.50 (2H, m), 7.95 (1H, dd, J = 2.1, 8.5 Hz), 8.20 (1H, d, J = 2.1 Hz), 8.23 (1H, s), 9.05 (2H, s), 12.54 (1H, s). |
| 257 | | 257 | NMR1; 7.22-7.32 (3H, m), 7.42-7.52 (2H, m), 7.58 (1H, dd, J = 8.4, 1.7 Hz), 7.73 (1H, d, J = 8.3 Hz), 7.97 (1H, d. J = 1.9 Hz), 8.39 (1H, s), 9.00 (2H, s) (NH and oxalic acid protons were not found). |

TABLE 2-27

| EX | STR | Prop | DATA |
|---|---|---|---|
| 258 | | 1 | NMR2; 7.22-7.34 (3H, m), 7.43-7.51 (2H, m), 7.55 (1H, dd, J = 8.7, 1.7 Hz), 7.64 (1H, dt, J = 8.7, 1.0 Hz), 7.90 (1H, dd, J = 1.6, 0.9 Hz), 8.17 (1H, d, J = 1.1 Hz), 8.80 (2H, s), 10.24 (1H, s). |
| 259 | | 1 | NMR2; 3.63 (2H, d, J = 1.0 Hz), 6.96-7.03 (1H, m). 7.20-7.33 (3H, m), 7.33-7.42 (2H, m), 7.42-7.50 (2H, m), 8.31 (1H, s), 8.70 (2H, s). |
| 260 | | 1 | NMR2; 3.84 (3H, s), 6.56 (1H, dd, J = 3.1, 0.9 Hz), 7.13 (1H, d, J = 3.1 Hz), 7.21-7.31 (3H, m), 7.35 (1H, dd, J = 8.5, 1.8 Hz), 7.39-7.51 (3H, m), 7.76 (1H, dd, J = 1.8, 0.7 Hz), 8.79 (2H, s). |
| 261 | | 139 | NMR1; 6.68-6.75 (1H, m), 6.94 (2H, s), 7.24-7.37 (3H, m), 7.43-7.53 (2H, m), 7.57 (1H, dd, J = 7.2, 8.3 Hz), 7.64 (1H, dd, J = 1.2, 7.2 Hz), 7.82 (1H, d, J = 6.0 Hz), 8.30 (1H, dt, J = 1.2, 8.3 Hz), 8.74 (2H, s). |
| 262 | | 262 | NMR2; 6.64 (1H, ddd, J = 3.1, 2.0, 1.0 Hz), 7.22-7.37 (5H, m), 7.41-7.55 (3H, m), 7.75-7.81 (1H, m), 8.30 (1H, s), 8.80 (2H, s). |

TABLE 2-27-continued
| EX | STR | Prop | DATA |
|---|---|---|---|
| 263 | 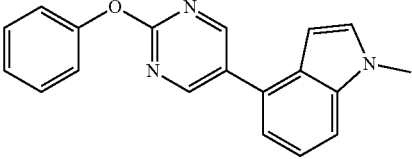 | 1 | NMR2; 3.85 (3H, s), 6.56 (1H, dd, J = 3.2, 0.9 Hz), 7.10-7.19 (2H, m), 7.24-7.37 (4H, m), 7.40 (1H, dt, J = 8.3, 1.0 Hz), 7.43-7.52 (2H, m), 8.87 (2H, s). |
| 264 | 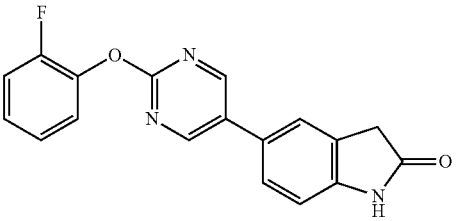 | 1 | NMR2; 3.62 (2H, d, J = 1.0 Hz), 6.95-7.02 (1H, m), 7.17-7.44 (6H, m), 7.92 (1H, s), 8.70 (2H, s). |
| 265 | 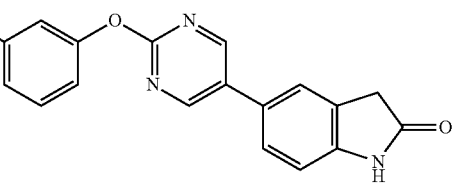 |  | NMR2; 3.63 (2H, d, J = 1.0 Hz), 6.94-7.09 (4H, m), 7.34-7.47 (3H, m), 7.87 (1H, s), 8.71 (2H, s). |
| 266 | 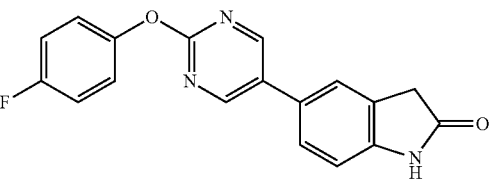 | 1 | NMR2; 3.62 (2H, s), 6.95-7.02 (1H, m), 7.08-7.25 (4H, m), 7.33-7.41 (2H, m), 7.77 (1H, s), 8.70 (2H, s). |
| 267 | 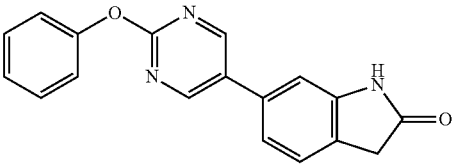 | 1 | NMR2; 3.58-3.63 (2H, m), 6.98-7.03 (1H, m), 7.16 (1H, dd, J = 7.7, 1.7 Hz), 7.20-7.32 (3H, m), 7.32-7.38 (1H, m), 7.41-7.51 (2H, m), 8.14 (1H, brs), 8.72 (2H, s). |
TABLE 2-28
| EX | STR | Prop | DATA |
|---|---|---|---|
| 268 | 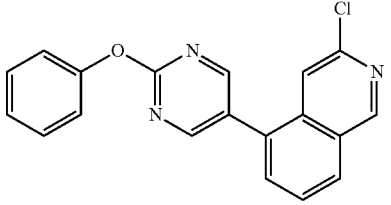 | 1 | NMR1; 7.25-7.36 (3H, m), 7.45-7.54 (2H, m), 7.75-7.81 (1H, m), 7.79-7.92 (2H, m), 8.30 (1H, d, J = 8.0 Hz), 8.82 (2H, s), 9.31-9.36 (1H, m). |
| 269 | 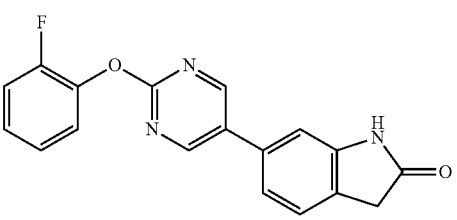 | 1 | NMR2; 3.58-3.68 (2H, m), 6.99-7.04 (1H, m), 7.16 (1H, dd, J = 7.7, 1.7 Hz), 7.18-7.38 (5H, m), 8.30 (1H, s), 8.72 (2H, s). |

TABLE 2-28-continued

| EX | STR | Prop | DATA |
|---|---|---|---|
| 270 | | 139 | NMR1; 2.94 (2H, t, J = 7.5 Hz), 3.31-3.44 (2H, m), 6.96 (1H, d, J = 8.2 Hz), 7.24-7.39 (2H, m), 7.35-7.47 (2H, m), 7.52 (1H, dd, J = 2.2, 8.2 Hz), 7.59 (1H, d, J = 2.0 Hz), 8.92 (2H, s), 10.21 (1H, s). |
| 271 | | 1 | NMR2; 7.08 (1H, dd, J = 0.6, 8.2 Hz), 7.19-7.34 (3H, m), 7.42-7.52 (2H, m), 7.68-7.80 (2H, m), 8.21 (1H, s), 8.71 (2H, s). |
| 272 | | 1 | NMR2; 3.58 (2H, s), 6.94 (1H, d, J = 8.0 Hz), 7.03 (1H, dd, J = 7.9, 1.0 Hz), 7.21-7.40 (4H, m), 7.43-7.52 (2H, m), 8.08-8.23 (1H, m), 8.66 (2H, s). |
| 273 | | 1. | NMR2; 3.44 (2H, s), 3.99 (3H, s), 6.87-6.98 (2H, m), 7.22-7.35 (4H, m), 7.40-7.50 (2H, m), 7.93 (1H, s), 8.20 (1H, s). |
| 274 | | 1 | NMR2; 3.60 (2H, s), 3.99 (3H, s), 6.89-6.96 (1H, m), 7.20-7.29 (3H, m), 7.29-7.39 (2H, m), 7.40-7.49 (2H, m), 7.85 (1H, s), 8.21 (1H, s). |
| 275 | | 1 | NMR2; 4.19 (3H, s), 7.22-7.35 (3H, m), 7.42-7.54 (3H, m), 8.04 (1H, s), 8.15 (1H, d, J = 8.3 Hz), 9.28 (2H, s). |
| 276 | | 1 | NMR2; 4.19 (3H, s), 7.19-7.39 (4H, m), 7.51 (1H, d, J = 8.3 Hz), 8.04 (1H, s), 8.16 (1H, d, J = 8.3 Hz), 9.28 (2H, s). |

TABLE 2-28-continued

| EX | STR | Prop | DATA |
|---|---|---|---|
| 277 | | 1 | NMR2; 4.20 (3H, s), 6.96-7.11 (3H, m), 7.37-7.48 (1H, m), 7.52 (1H, d, J = 8.3 Hz), 8.04 (1H, s), 8.17 (1H, d, J = 8.3 Hz), 9.29 (2H, s). |

TABLE 2-29

| EX | STR | Prop | DATA |
|---|---|---|---|
| 278 | | 1 | NMR2; 4.19 (3H, s), 7.09-7.23 (2H, m), 7.19-7.27 (2H, m), 7.51 (1H, d, J = 8.3 Hz), 8.04 (1H, s), 8.16 (1H, d, J = 8.3 Hz), 9.28 (2H, s). |
| 279 | | 1 | NMR2; 7.20-7.28 (2H, m), 7.28-7.36 (1H, m), 7.43-7.53 (2H, m), 7.60 (1H, dd, J = 9.5, 1.6 Hz), 8.07 (1H, dd, J = 9.5, 1.1 Hz), 8.28-8.34 (1H, m), 8.78 (2H, s). |
| 280 | | 1 | NMR2; 7.19-7.37 (4H, m), 7.61 (1H, dd, J = 9.5, 1.6 Hz), 8.08 (1H, dd, J = 9.6, 1.2 Hz), 8.30-8.35 (1H, m), 8.78 (2H, s). |
| 281 | | 1 | NMR2; 7.19-7.37 (4H, m), 7.61 (1H, dd, J = 9.5, 1.6 Hz), 8.08 (1H, dd, J = 9.6, 1.2 Hz), 8.30-8.35 (1H, m), 8.78 (2H, s). |
| 282 | | 1 | NMR2; 6.96-7.09 (3H, m), 7.44 (1H, td, J = 8.3, 6.5 Hz), 7.61 (1H, dd, J = 9.5, 1.6 Hz), 8.08 (1H, dd, J = 9.6, 1.1 Hz), 8.29-8.35 (1H, m), 8.80 (2H, s). |
| 283 | | 1 | NMR2; 6.75 (1H, dd, J = 7.4, 1.8 Hz), 7.20-7.34 (3H, m), 7.42-7.52 (2H, m), 7.55 (1H, s), 7.58-7.64 (1H, m), 8.05 (1H, dt, J = 7.3, 1.1 Hz), 8.17 (1H, s), 8.78 (2H, s). |

TABLE 2-29-continued

| EX | STR | Prop | DATA |
|---|---|---|---|
| 284 | | 1 | NMR2; 6.76 (1H, dd, J = 7,3, 1.8 Hz), 6.96-7.09 (3H, m), 7.36-7.47 (1H, m), 7.56 (1H, s), 7.60-7.66 (1H, m), 8.06 (1H, dt, J = 7.3, 1.1 Hz), 8.18 (1H, s), 8.79 (2H, s). |
| 285 | | 1 | NMR2; 7.09 (1H, dd, J = 9.4, 1.4 Hz), 7.20-7.28 (2H, m), 7.28-7.34 (1H, m), 7.43-7.53 (2H, m), 7.62 (1H, d, J = 1.0 Hz), 7.72 (1H, dd, J = 9.4, 1.1 Hz), 8.23 (1H, s), 8.76 (2H, s). |
| 286 | | 1 | NMR2; 7.10 (1H, dd, J = 9.4, 1.5 Hz), 7.18-7.37 (4H, m), 7.62 (1H, d, J = 1.0 Hz), 7.73 (1H, dd, J = 9.4, 1.2 Hz), 8.24 (1H, s), 8.76 (2H, s). |
| 287 | | 1 | NMR2; 6.97-7.08 (3H, m), 7.10 (1H, dd, J = 9.4, 1.5 Hz), 7.43 (1H, tdd, J = 8.2, 6.5, 0.7 Hz), 7.62 (1H, d, J = 0.9 Hz), 7.74 (1H, dd, J = 9.4, 1.2 Hz), 8.25 (1H, s), 8.78 (2H, s). |
| 288 | | 1 | NMR2; 7.09 (1H, dd, J = 9.4, 1.5 Hz), 7.10-7.26 (4H, m), 7.62 (1H, d, J = 0.9 Hz), 7.73 (1H, dd, J = 9.4, 1.2 Hz), 8.24 (1H, s), 8.76 (2H, s). |

TABLE 2-30

| EX | STR | Prop | DATA |
|---|---|---|---|
| 289 | | 1 | NMR2; 7.21-7.29 (2H, m), 7.29-7.37 (1H, m), 7.43-7.55 (3H, m), 8.29 (1H, dd, J = 9.7, 0.8 Hz), 9.16 (2H, s), 9.19 (1H, d, J = 0.8 Hz). |
| 290 | | 1 | NMR2; 7.20-7.38 (4H, m), 7.53 (1H, d, J = 9.7 Hz), 8.29 (1H, dd, J = 9.7, 0.8 Hz), 9.16 (2H, s), 9.20 (1H, d, J = 0.8 Hz). |

TABLE 2-30-continued
| EX | STR | Prop | DATA |
|---|---|---|---|
| 291 | 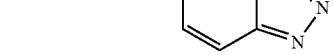 | 1 | NMR2; 6.97-7.10 (3H, m), 7.40-7.48 (1H, m), 7.52 (1H, d, J = 9.7 Hz), 8.30 (1H, dd, J = 9.7, 0.8 Hz), 9.17 (2H, s), 9.20 (1H, d, J = 0.8 Hz). |
| 292 | 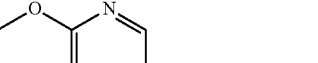 | 1 | NMR2; 7.11-7.26 (4H, m), 7.51 (1H, d, J = 9.7 Hz), 8.29 (1H, dd, J = 9.7, 0.8 Hz), 9.16 (2H, s), 9.20 (1H, d, J = 0.8 Hz). |
| 293 | 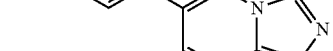 | 1 | NMR2; 7.21-7.29 (2H, m), 7.29-7.37 (1H, m), 7.44-7.54 (2H, m), 8.60 (1H, s), 8.82 (2H, s), 8.98-9.05 (2H, m). |
| 294 |  | 1 | NMR2; 7.32 (1H, dd, J = 9.3, 1.8 Hz), 7.38-7.47 (1H, m), 7.62 (1H, ddd, J = 8.3, 2.8, 1.4 Hz), 7.67-7.81 (3H, m), 8.32 (1H, dd, J = 1.9, 1.0 Hz), 8.55 (1H, dd, J = 4.7, 1.4 Hz), 8.62 (1H, d, J = 2.7 Hz), 8.76 (2H, s). |
| 295 | 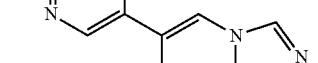 | 1 | NMR2; 6.56 (1H, t, J = 73.5 Hz), 7.03-7.09 (2H, m), 7.12 (1H, ddd, J = 8.3, 2.1, 1.1 Hz), 7.31 (1H, dd, J = 9.3, 1.9 Hz), 7.41-7.50 (1H, m), 7.67-7.80 (3H, m), 8.31 (1H, dd, J = 1.9, 1.0 Hz), 8.76 (2H, s). |
| 296 |  | 1 | NMR2; 7.20-7.28 (2H, m), 7.29-7.36 (1H, m), 7.42-7.53 (2H, m), 7.83 (1H, dd, J = 5.3, 0.5 Hz), 8.98 (1H, d, J = 5.3 Hz), 9.30 (2H, s). |
| 297 |  | 1 | NMR2; 7.19-7.28 (2H, m), 7.32 (1H, ddt, J = 7.9, 7.0, 1.1 Hz), 7.43-7.53 (2H, m), 7.68 (1H, dd, J = 5.2, 1.8 Hz), 7.86 (1H, dd, J = 1.8, 0.8 Hz), 8.80-8.86 (3H, m). |
| 298 | 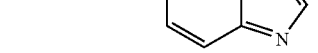 | 1 | NMR2; 4.60 (2H, s), 7.18-7.37 (3H, m), 7.42-7.58 (4H, m), 8.47-8.52 (1H, m), 8.76 (2H, s). |

TABLE 2-31

| EX | STR | Prop | DATA |
|---|---|---|---|
| 299 | | 1 | NMR; 7.20-7.28(2H, m), 7.28-7.35(1H, m), 7.43-7.53(2H, m), 7.62-7.69(1H, m), 7.81-7.87(1H, m), 8.85(3H, s) |
| 300 | | 1 | NMR2; 7.21-7.35(3H, m), 7.42-7.52(2H, m), 7.58(1H, d, J = 5.0 Hz), 9.05(1H, d, J = 5.0 Hz), 9.57(2H, s). |
| 301 | | 1 | NMR2; 7.20-7.34(3H, m), 7.41-7.53(2H, m), 7.65-7.72(1H, m), 7.86(1H, d, J = 8.0 Hz), 7.94-8.04(1H, m), 9.21(2H, s). |

TABLE 2-32

| EX | STR | Prop | DATA |
|---|---|---|---|
| 302 | | 302 | NMR2; 2.85 (2H, t, J = 6.7 Hz), 3.87 (2H, t, J = 6.7 Hz), 6.71-6.75 (1H, m), 6.60-6.85 (2H, m), 7.04-7.08 (2H, m), 7.27-7.32 (3H, m), 7.57 (1H, br). |
| 303 | | 302 | NMR2; 2.84 (2H, t, J = 6.7 Hz), 3.86 (2H, t, J = 6.7 Hz), 7.00-7.06 (4H, m), 7.11-7.17 (1H, m), 7.22-7.28 (2H, m), 7.32-7.39 (2H, m), 7.56 (1H, s). |
| 304 | | 302 | NMR1; 2.68 (2H, t, J = 6.7 Hz), 3.67 (2H, t, J = 6.7 Hz), 3.93 (2H, s), 7.16-7.20 (1H, m), 7.23-7.31 (8H, m), 10.33 (1H, s). |
| 305 | | 305 | NMR2; 2.83 (2H, t, J = 6.7 Hz), 3.86 (2H, t, J = 6.7 Hz), 3.97 (2H, s), 6.86-6.99 (3H, m), 7.20-7.28 (5H, m), 7.42 (1H, br). |
| 306 | | 302 | NMR2; 2.85 (2H, t, J = 6.7 Hz), 3.87 (2H, t, J = 6.7 Hz), 6.89-6.90 (1H, m), 6.93-6.99 (2H, m), 7.04-7.08 (2H, m), 7.28-7.37 (3H, m), 7.74 (1H, br). |

TABLE 2-32-continued

| EX | STR | Prop | DATA |
|---|---|---|---|
| 307 | | 302 | NMR2; 2.85 (2H, t, J = 6.7 Hz), 3.88 (2H, t, J = 6.7 Hz), 7.04-7.08 (2H, m), 7.18-7.21 (1H, m), 7.28-7.38 (3H, m), 7.38 (1H, d, J = 7.8 Hz), 7.46 (1H, t, J = 7.9 Hz), 7.73 (1H, br). |
| 308 | | 308 | NMR2; 2.89 (2H, t, J = 6.7 Hz), 3.24 (3H, s), 3.80 (2H, t, J = 6.7 Hz), 6.69-6.75 (1H, m), 6.79-6.84 (2H, m), 7.04-7.08 (2H, m), 7.25-7.31 (3H, m). |
| 309 | | 302 | NMR2; 2.84 (2H, t, J = 6.7 Hz), 3.85 (2H, t, J = 6.7 Hz), 6.95-7.05 (2H, m), 7.07-7.29 (6H, m), 7.47 (1H, s). |
| 310 | | 302 | NMR1; 2.70 (2H, t, J = 6.9 Hz), 3.76 (2H, t, J = 6.7 Hz), 6.97-7.03 (2H, m), 7.05-7.12 (2H, m), 7.20-7.28 (2H, m), 7.30-7.36 (2H, m), 10.37 (1H, s). |
| 311 | | 302 | NMR2; 2.84 (2H, t, J = 6.7 Hz), 3.79 (3H, s), 3.86 (2H, t, J = 6.7 Hz), 6.58-6.64 (2H, m), 6.66-6.72 (1H, m), 7.01-7.07 (2H, m), 7.21-7.28 (3H, m), 7.56 (1H, br). |

TABLE 2-33

| EX | STR | Prop | DATA |
|---|---|---|---|
| 312 | | 302 | NMR2; 2.85 (2H, t, J = 6.6 Hz), 3.89 (2H, t, J = 6.8 Hz), 6.90-6.96 (1H, m), 6.96-7.02 (1H, m), 7.09 (1H, ddd, J = 1.0, 1.6, 7.9 Hz), 7.23-7.32 (3H, m), 7.40-7.45 (2H, m), 7.52 (1H, br). |
| 313 | | 302 | NMR2; 2.83 (2H, t, J = 6.7 Hz), 3.86 (2H, t, J = 6.7 Hz), 7.20-7.25 (2H, m), 7.25-7.36 (5H, m), 7.36-7.41 (2H, m), 7.49 (1H, br). |

TABLE 2-33-continued

| EX | STR | Prop | DATA |
|---|---|---|---|
| 314 | | 314 | NMR2; 2.85 (2H, t, J = 6.7 Hz), 3.87 (2H, t, J = 6.7 Hz), 6.51 (1H, t, J = 73.6 Hz), 6.80 (1H, dd, J = 2.2, 2.2 Hz), 6.84-6.91 (2H, m), 7.03-7.09 (2H, m), 7.27-7.35 (3H, m), 7.51 (1H, br). |
| 315 | | 302 | NMR2; 2.82 (2H, t, J = 6.7 Hz), 3.85 (2H, t, J = 6.7 Hz), 6.86 (1H, ddd, J = 0.8, 2.4, 8.3 Hz), 6.93 (1H, dd, J = 2.2, 2.2 Hz), 6.98-7.09 (5H, m), 7.34 (1H, dd, J = 8.1, 8.1 Hz), 7.56 (1H, br). |
| 316 | | 302 | NMR2; 2.84 (2H, t, J = 6.7 Hz), 3.89 (2H, t, J = 6.7 Hz), 6.95 (1H, ddd, J = 0.8, 0.8, 8.3 Hz), 7.02 (1H, ddd, J = 0.9, 5.0, 7.2 Hz), 7.15-7.22 (2H, m), 7.30-7.36 (2H, m), 7.59 (1H, br), 7.71 (1H, ddd, J = 2.0, 7.2, 8.3 Hz), 8.20 (1H, ddd, J = 0.7, 2.0, 5.0 Hz). |
| 317 | | 302 | NMR2; 2.86 (2H, t, J = 6.7 Hz), 3.89 (2H, t, J = 6.7 Hz), 7.00-7.06 (2H, m), 7.07-7.13 (2H, m), 7.30-7.37 (2H, m), 7.53 (1H, br), 7.69-7.75 (2H, m). |
| 318 | | 302 | NMR1; 2.71 (2H, t, J = 6.7 Hz), 3.78 (2H, t, J = 6.7 Hz), 7.07-7.12 (2H, m), 7.35-7.40 (2H, m), 7.43-7.46 (2H, m), 8.36-8.42 (2H, m), 10.39 (1H, s). |
| 319 | | 302 | NMR2; 2.83 (2H, t, J = 6.6 Hz), 3.87 (2H, t, J = 6.7 Hz), 7.21-7.30 (2H, m), 7.30-7.39 (2H, m), 8.16 (1H, s). |
| 320 | | 302 | NMR2; 2.86 (2H, t, J = 6.7 Hz), 3.85 (2H, t. J = 6.7 Hz), 6.95 (1H, dd, J = 8.8, 0.6 Hz), 7.11-7.18 (2H, m), 7.19-7.25 (1H, m), 7.36-7.47 (2H, m), 7.69 (1H, dd, J = 8.8, 2.8 Hz), 7.78 (1H, s), 8.11 (1H, dd, J = 2.8, 0.7 Hz). |
| 321 | | 321 | NMR2; 2.85 (2H, t, J = 6.7 Hz), 3.90 (2H, t, J = 6.7 Hz), 6.61-6.66 (1H, m), 6.76-6.81 (1H, m), 7.17-7.22 (2H, m), 7.31-7.36 (2H, m), 7.46 (1H, br), 7.78 (1H, dd, J = 8.0 Hz, 16.0 Hz). |

TABLE 2-34
| EX | STR | Prop | DATA |
|---|---|---|---|
| 322 | 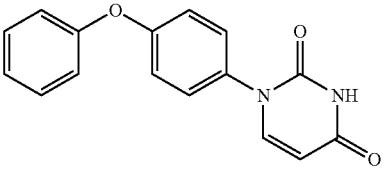 | 322 | NMR1; 5.69 (1H, d, J = 7.6 Hz), 6.99-7.13 (4H, m), 7.15-7.26 (3H, m), 7.39-7.49 (2H, m), 7.52 (1H, d, J = 7.7 Hz), 11.25 (1H, s). |
| 323 | 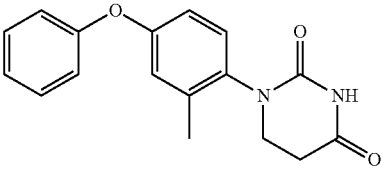 | 302 | NMR2; 2.23 (3H, s), 2.75-2.93 (2H, m), 3.58-3.69 (1H, m), 3.80 (1H, ddd, J = 12.7, 8.2, 6.4 Hz), 6.83-6.88 (1H, m), 6.91 (1H, d, J = 2.8 Hz), 7.00-7.09 (2H, m), 7.09-7.19 (2H, m), 7.31-7.42 (2H, m), 7.58 (1H, s). |
| 324 | 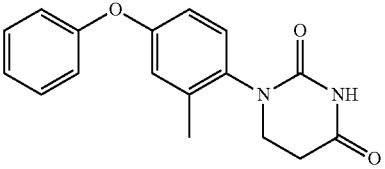 | 302 | NMR2; 2.81 (2H, t, J = 6.7 Hz), 3.69 (2H, s), 3.80 (3H, s), 6.54 (1H, dd, J = 8.6, 2.6 Hz), 6.67 (1H, d, J = 2.5 Hz), 7.02-7.10 (2H, m), 7.11-7.21 (2H, m), 7.32-7.42 (2H, m), 7.68 (1H, s). |
| 325 | 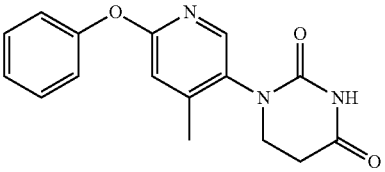 | 302 | NMR2; 2.27 (3H, d, J = 0.7 Hz), 2.81-2.90 (2H, m), 3.65 (1H, dt, J = 12.6, 6.3 Hz), 3.81 (1H, ddd, J = 12.6, 7.9, 6.3 Hz), 6.82 (1H, t, J = 0.7 Hz), 7.09-7.18 (2H, m), 7.19-7.25 (1H, m), 7.36-7.46 (2H, m), 7.78 (1H, s), 8.01 (1H, s). |
| 326 | 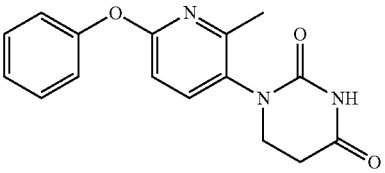 | 302 | NMR2; 2.39 (3H, s), 2.82-2.91 (2H, m), 3.66 (1H, t, J = 6.2 Hz), 3.71-3.83 (1H, m), 6.69 (1H, d, J = 8.5 Hz), 7.12-7.18 (2H, m), 7.18-7.25 (1H, m), 7.36-7.43 (2H, m), 7.47 (2H, d, J = 8.5 Hz). |
| 327 | 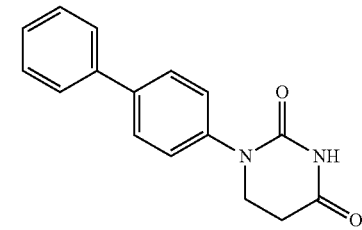 | 327 | NMR1; 2.73 (2H, t, J = 6.7 Hz), 3.84 (2H, t, J = 6.7 Hz), 7.34-7.40 (1H, m), 7.40-7.45 (2H, m), 7.45-7.51 (2H, m), 7.65-7.72 (4H, m), 10.41 (1H, br). |
| 328 | 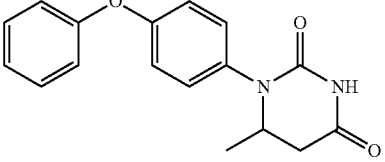 | 328 | NMR2; 1.32 (3H, d, J = 6.6 Hz), 2.61 (1H, ddd, J = 0.8 Hz, 3.6 Hz, 16.6 Hz), 3.05 (1H, dd, J = 6.0 Hz, 16.6 Hz), 3.98-4.07 (1H, m), 7.01-7.08 (4H, m), 7.12-7.18 (1H, m), 7.19-7.25 (2H, m), 7.33-7.40 (2H, m), 7.48 (1H, br). |
| 329 | 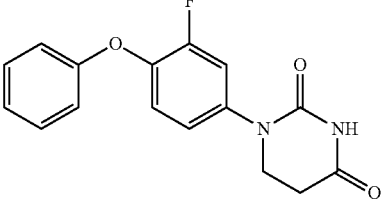 | 302 | NMR1; 2.72 (2H, t, J = 6.6 Hz), 3.82 (2H, t, J = 6.6 Hz), 6.94-7.03 (2H, m), 7.09-7.16 (1H, m), 7.16-7.25 (2H, m), 7.34-7.42 (2H, m), 7.42-7.50 (1H, m), 10.47 (1H, s). |

TABLE 2-34-continued

| EX | STR | Prop | DATA |
|---|---|---|---|
| 330 | | 302 | NMR1; 2.68-2.77 (2H, m), 3.85 (2H, t, J = 6.6 Hz), 6.92-7.01 (2H, m), 7.07-7.16 (1H, m), 7.32-7.44 (4H, m), 10.56 (1H, s). |

TABLE 2-35

| EX | STR | Prop | DATA |
|---|---|---|---|
| 331 | | 302 | NMR1; 2.72 (2H, t, J = 6.7 Hz), 3.78 (2H, t, J = 6.7 Hz), 7.17 (1H, dd, J = 8.7, 0.7 Hz), 7.21-7.42 (4H, m), 7.87 (1H, dd, J = 8.8, 2.7 Hz), 8.08 (1H, dd, J = 2.8, 0.7 Hz), 10.48 (1H, s). |
| 332 | | 302 | NMR1; 2.73 (2H, t, J = 6.7 Hz), 3.80 (2H, t, J = 6.7 Hz), 6.99 (1H, ddd, J = 8.2, 2.1, 0.9 Hz), 7.04-7.11 (2H, m), 7.13 (1H, dd, J = 8.7, 0.6 Hz), 7.40-7.51 (1H, m), 7.88 (1H, dd, J = 8.7, 2.8 Hz), 8.16 (1H, dd, J = 2.8, 0.7 Hz), 10.49 (1H, s). |
| 333 | | 302 | NMR1; 2.72 (2H, t, J = 6.6 Hz), 3.79 (2H, t, J = 6.7 Hz), 7.18 (1H, dd, J = 8.7, 0.6 Hz), 7.44-7.51 (1H, m), 7.51-7.56 (1H, m), 7.57-7.63 (1H, m), 7.63-7.72 (1H, m), 7.90 (1H, dd, J = 8.8, 2.8 Hz), 8.15 (1H, dd, J = 2.8, 0.6 Hz), 10.49 (1H, s). |
| 334 | | 302 | NMR2; 2.25 (3H, s), 2.76-2.94 (2H, m), 3.65 (1H, dt, J = 12.6, 6.1 Hz), 3.81 (1H, ddd, J = 12.7, 8.2, 6.4 Hz), 6.74 (1H, dt, J = 10.1, 2.4 Hz), 6,79-6.86 (2H, m), 6.87-6.92 (1H, m), 6.92-6.97 (1H, m), 7.16 (1H, d, J = 8.5 Hz), 7.30 (1H, td, J = 8.3, 6.6 Hz), 7.56 (1H, s). |
| 335 | | 302 | NMR2; 2.26 (3H, s), 2.77-2.94 (2H, m), 3.66 (1H, dt, J = 12.5, 6.1 Hz), 3.82 (1H, ddd, J = 12.7, 8.3, 6.4 Hz), 6.89 (1H, ddd, J = 8.6, 2.9, 0.6 Hz), 6.94 (1H, dd, J = 2.7, 0.7 Hz), 7.14-7.23 (2H, m), 7.27-7.32 (1H, m), 7.35-7.42 (1H, m), 7.42-7.50 (1H, m), 7.62 (1H, s). |
| 336 | | 302 | NMR2; 2.26 (3H, s), 2.76-2.92 (2H, m), 3.65 (1H, dt, J = 12.5, 6.1 Hz), 3.82 (1H, ddd, J = 12.7, 8.3, 6.3 Hz), 6.85-7.03 (5H, m), 7.17 (1H, d, J = 8.5 Hz), 7.35 (1H, t, J = 8.2 Hz), 7.73 (1H, s). |

TABLE 2-35-continued

| EX | STR | Prop | DATA |
|---|---|---|---|
| 337 | | 337 | NMR2; 1.31 (6H, s), 2.74 (2H, s), 6.99-7.05 (2H, m), 7.05-7.10 (2H, m), 7.11-7.20 (3H, m), 7.34-7.42 (2H, m), 7.52 (1H, br). |
| 338 | | 305 | NMR2; 2.82 (2H, t, J = 6.7 Hz), 3.85 (2H, t, J = 6.7 Hz), 3.95 (2H, s), 6.94-7.01 (2H, m), 7.10-7.17 (2H, m), 7.18-7.24 (4H, m), 7.43 (1H, br). |
| 339 | | 305 | NMR2; 2.83 (2H, t, J = 6.7 Hz), 3.86 (2H, t, J = 6.7 Hz), 4.00 (2H, s), 7.02-7.14 (3H, m), 7.19-7.28 (4H, m), 7.31 (1H, dd, J = 7.9, 7.9 Hz), 7.43 (1H, br). |

TABLE 2-36

| EX | STR | Prop | DATA |
|---|---|---|---|
| 340 | | 305 | NMR2; 2.82(2H, t, J = 6.7 Hz), 3.86(2H, t, J = 6.7 Hz), 3.98(2H, s), 7.11-7.16(2H, m), 7.17-7.25(6H, m), 7.47(1H, br). |
| 341 | | 305 | NMR2; 2.83(2H, t, J = 6.7 Hz), 3.86(2H, t, J = 6.7 Hz), 4.04(2H, s), 7.19-7.27(4H, m), 7.34-7.51(5H, m). |
| 342 | | 305 | NMR2; 2.83(2H, t, J = 6.7 Hz), 3.86(2H, t, J = 6.7 Hz), 4.04(2H, s), 7.18-7.27(4H, m), 7.30(2H, d, J = 7.9 Hz), 7.49(1H, br), 7.55(2H, d, J = 8.0 Hz). |
| 343 | | 343 | NMR2; 0.91(3H, t, J = 7.5 Hz), 1.60-1.73(1H, m), 1.74-1.87(1H, m), 2.76(1H, ddd, J = 0.9, 2.8, 16.7 Hz), 3.01(1H, ddd, J = 0.5, 6.4, 16.7 Hz), 3.75-3.83(1H, m), 7.00-7.08(4H, m), 7.12-7.18(1H, m), 7.21-7.28(2H, m), 7.33-7.41(2H, m), 7.46(1H, br). |

TABLE 2-36-continued
| EX | STR | Prop | DATA |
|---|---|---|---|
| 344 | 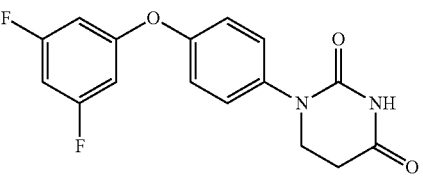 | 344 | NMR2; 2.88(2H, t, J = 6.7 Hz), 3.89(2H, t, J = 6.7 Hz), 6.48-6.60(3H, m), 7.06-7.13(2H, m), 7.30-7.36(2H, m), 7.51(1H, br). |
| 345 | 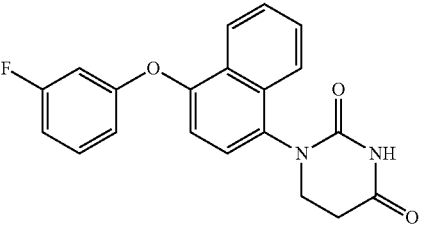 | 302 | NMR2; 2.87-3.08(2H, m), 3.79-3.97(2H, m), 6.78-6.90(3H, m), 6.98(1H, d, J = 8.1 Hz), 7.32(1H, ddd, J = 6.6 Hz, 8.3 Hz, 8.3 Hz), 7.37 (1H, d, J = 8.0 Hz), 7.54-7.67(3H, m), 7.78-7.83(1H, m), 8.23-8.29(1H, m). |
| 346 | 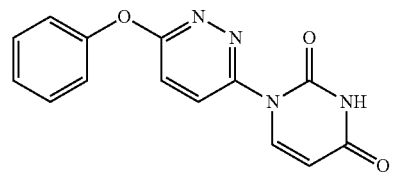 | 346 | NMR2; 5.82(1H, d, J = 8.0 Hz), 7.20-7.34(3H, m), 7.43-7.53(2H, m), 7.93(1H, d, J = 8.0 Hz), 8.49-8.55(2H, m), 11.65(1H, s). |
| 347 | 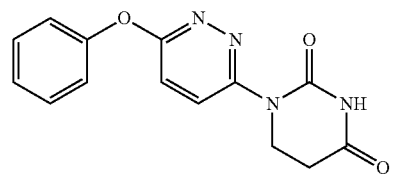 | 347 | NMR2; 2.84(2H, t, J = 6.7 Hz), 4.32(2H, t, J = 6.7 Hz), 7.16-7.35(4H, m), 7.38-7.50(2H, m), 7.54(1H, s), 8.13(1H, d, J = 9.5 Hz). |
TABLE 2-37
| EX | STR | Prop | DATA |
|---|---|---|---|
| 348 | 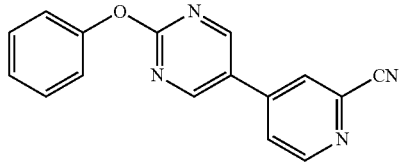 | 1 | NMR2; 7.21-7.26(2H, m), 7.29-7.35(1H, m), 7.45-7.52(2H, m), 7.68(1H, dd, J = 5.1, 1.8 Hz), 7.86(1H, dd, J = 1.8, 0.7 Hz), 8.80-8.85(3H, m). |
| 349 | 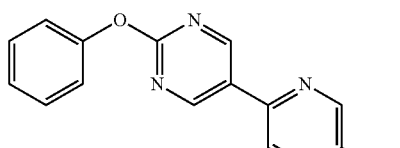 | 1 | NMR2; 7.22-7.27(2H, m), 7.28-7.34(1H, m), 7.45-7.51(2H, m), 7.80(1H, dd, J = 8.3, 0.8 Hz), 8.06(1H, dd, J = 8.3, 2.2 Hz), 8.96(1H, d, J = 2.2, 0.8 Hz), 9.21(2H, s). |
| 350 | 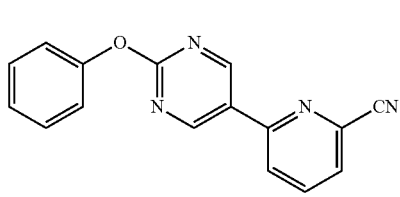 | 1 | NMR2; 7.22-7.28(2H, m), 7.28-7.34(1H, m), 7.43-7.51(2H, m), 7.70(1H, dd, J = 7.5, 1.0 Hz), 7.89(1H, dd, J = 8.2, 1.0 Hz), 7.96(1H, dd, J = 8.2, 7.5 Hz), 9.18(2H, s). |

Test Examples

Pharmacological test results for typical compounds of the present invention are given below and the pharmacological actions of these compounds are explained, but the present invention is not limited by these test examples.

[Test Example 1] Audiogenic Seizure Model

The animal model used in this test is a phenotype model for partial seizure (including secondary generalized seizure) and generalized tonic-clonic seizure, and has high clinical predictability. This test was performed in accordance with the report of De Sarro et al (Br J Pharmacol. 1988 February; 93 (2): 247-56. Anticonvulsant effects of some calcium entry blockers in DBA/2 mice. De Sarro G B, Meldrum B S, Nistico G.).

In this test example, the example compounds shown in Tables 3-1 to 3-3 below were used as test compounds.

The test compounds were suspended in 5% gum arabic/ distilled water (w/v), and administered by forced oral administration to male and female DBA/2 mice (Japan SLC, Inc., 3 weeks old, 8 per group) at a dose of 30 mg/kg. After one hour of the oral administration of the test compound, each mouse was placed in a transparent acrylic cylinder 30 cm high and 23 cm in diameter, and 30 seconds were allowed for habituation. Then, they were exposed to auditory stimulation (12.6 kHz, 100-110 dB) for 1 minute or until a tonic seizure occurred.

The seizure response was assessed using the following scale, 0: no seizure, 1: wild running, 2: clonic seizure, 3: tonic seizure and 4: respiratory arrest. The maximum response was recorded as the seizure severity score.

The seizure suppression rate for each compound administration group was calculated according to the following formula.

$$\text{seizure suppression rate (\%)} = \left(1 - \frac{\text{seizure severity score of compound administration group}}{\text{seizure severity score of solvent administration group}}\right) \times 100 \quad [\text{Math.1}]$$

The results are shown in Tables 3-1 to 3-3.

Here, a rate of seizure suppression of 90% or more was expressed as "A", a rate of seizure suppression of 70% or more and less than 90% was expressed as "B", and a rate of seizure suppression of 50% or more and less than 70% was expressed as "C".

TABLE 3-1

| EX | Dose (mg/kg) | Seizure suppression |
|---|---|---|
| 1 | 5 | A |
| 2 | 30 | A |
| 3 | 5 | A |
| 4 | 5 | A |
| 5 | 5 | A |
| 6 | 5 | A |
| 7 | 5 | A |
| 8 | 10 | A |
| 9 | 5 | A |
| 10 | 30 | A |
| 11 | 5 | A |
| 12 | 3 | A |
| 13 | 3 | A |
| 14 | 30 | A |
| 15 | 30 | A |
| 16 | 30 | A |
| 17 | 30 | A |
| 18 | 30 | A |
| 19 | 30 | A |
| 20 | 30 | A |
| 21 | 30 | A |
| 22 | 5 | A |
| 23 | 30 | A |
| 24 | 5 | A |
| 25 | 30 | A |
| 26 | 5 | A |
| 27 | 30 | A |
| 28 | 30 | A |
| 29 | 30 | A |
| 30 | 5 | A |
| 31 | 5 | A |
| 32 | 30 | A |
| 33 | 5 | A |
| 34 | 30 | A |
| 35 | 30 | A |
| 36 | 5 | A |
| 37 | 30 | A |
| 38 | 10 | A |
| 39 | 30 | A |
| 40 | 3 | A |
| 41 | 30 | A |
| 42 | 5 | A |
| 43 | 30 | A |
| 44 | 30 | A |
| 45 | 5 | A |
| 46 | 30 | A |
| 47 | 30 | A |
| 48 | 30 | A |
| 49 | 30 | A |
| 50 | 30 | A |
| 51 | 30 | A |
| 52 | 30 | A |
| 53 | 30 | A |
| 54 | 30 | A |
| 55 | 30 | A |
| 56 | 30 | A |
| 57 | 30 | A |
| 58 | 30 | A |
| 59 | 3 | A |
| 60 | 30 | A |
| 61 | 30 | A |
| 62 | 30 | A |
| 63 | 30 | A |
| 64 | 3 | A |
| 65 | 30 | A |
| 66 | 30 | A |
| 67 | 30 | A |
| 68 | 30 | A |
| 69 | 30 | A |
| 70 | 30 | A |
| 71 | 30 | A |
| 72 | 30 | A |
| 73 | 30 | A |
| 74 | 5 | A |
| 75 | 30 | A |
| 76 | 30 | A |
| 77 | 30 | A |
| 78 | 30 | A |
| 79 | 30 | A |
| 80 | 30 | A |
| 81 | 30 | A |
| 82 | 30 | A |
| 83 | 30 | A |
| 84 | 30 | A |
| 85 | 30 | A |
| 86 | 30 | A |
| 87 | 30 | A |
| 88 | 30 | A |
| 89 | 30 | A |

TABLE 3-1-continued

| EX | Dose (mg/kg) | Seizure suppression |
|---|---|---|
| 90 | 5 | B |
| 91 | 5 | A |
| 92 | 5 | A |
| 93 | 30 | A |
| 94 | 30 | A |
| 95 | 3 | A |
| 96 | 30 | A |
| 97 | 3 | A |
| 98 | 3 | A |
| 99 | 10 | A |
| 100 | 30 | A |
| 101 | 3 | A |
| 102 | 10 | A |
| 103 | 30 | A |
| 104 | 30 | A |
| 105 | 30 | A |
| 106 | 5 | A |
| 107 | 30 | A |
| 108 | 30 | A |
| 109 | 30 | A |
| 110 | 30 | A |
| 111 | 30 | A |
| 112 | 30 | A |
| 113 | 10 | A |
| 114 | 5 | A |
| 115 | 30 | A |
| 116 | 30 | A |
| 117 | 30 | A |
| 118 | 5 | B |
| 119 | 5 | A |
| 120 | 5 | A |

TABLE 3-2

| EX | Dose (mg/kg) | Seizure suppression |
|---|---|---|
| 121 | 5 | A |
| 122 | 5 | A |
| 123 | 5 | A |
| 124 | 30 | A |
| 125 | 30 | A |
| 126 | 30 | A |
| 127 | 5 | A |
| 128 | 30 | A |
| 129 | 5 | A |
| 130 | 30 | A |
| 131 | 30 | A |
| 132 | 30 | A |
| 133 | 30 | A |
| 134 | 5 | A |
| 135 | 30 | A |
| 136 | 30 | A |
| 137 | 30 | A |
| 138 | 30 | A |
| 139 | 30 | A |
| 140 | 30 | A |
| 141 | 5 | A |
| 142 | 30 | A |
| 143 | 30 | A |
| 144 | 30 | A |
| 145 | 30 | A |
| 146 | 30 | A |
| 147 | 30 | A |
| 148 | 30 | A |
| 149 | 30 | A |
| 150 | 30 | A |
| 151 | 5 | A |
| 152 | 30 | A |
| 153 | 30 | A |
| 154 | 30 | A |
| 155 | 5 | A |
| 156 | 30 | A |
| 157 | 30 | A |

TABLE 3-2-continued

| EX | Dose (mg/kg) | Seizure suppression |
|---|---|---|
| 158 | 30 | A |
| 159 | 30 | A |
| 160 | 30 | A |
| 161 | 5 | A |
| 162 | 5 | A |
| 163 | 5 | A |
| 164 | 5 | A |
| 165 | 5 | A |
| 166 | 5 | A |
| 167 | 5 | A |
| 168 | 5 | A |
| 169 | 5 | A |
| 170 | 5 | A |
| 171 | 5 | A |
| 172 | 5 | A |
| 173 | 5 | A |
| 174 | 30 | A |
| 175 | 30 | A |
| 176 | 30 | A |
| 177 | 5 | B |
| 178 | 30 | A |
| 179 | 30 | A |
| 180 | 30 | A |
| 181 | 5 | B |
| 182 | 30 | A |
| 183 | 30 | A |
| 184 | 5 | A |
| 185 | 30 | A |
| 186 | 30 | A |
| 187 | 30 | A |
| 188 | 30 | A |
| 189 | 30 | A |
| 190 | 5 | A |
| 191 | 30 | A |
| 192 | 30 | A |
| 193 | 30 | A |
| 194 | 5 | A |
| 195 | 30 | A |
| 196 | 30 | A |
| 197 | 30 | A |
| 198 | 5 | A |
| 199 | 30 | A |
| 200 | 30 | A |
| 201 | 30 | A |
| 202 | 30 | A |
| 203 | 30 | A |
| 204 | 30 | A |
| 205 | 30 | A |
| 206 | 30 | A |
| 207 | 30 | A |
| 208 | 30 | A |
| 209 | 30 | A |
| 210 | 30 | A |
| 211 | 30 | A |
| 212 | 30 | A |
| 213 | 30 | A |
| 214 | 30 | A |
| 215 | 30 | A |
| 216 | 5 | A |
| 217 | 30 | A |
| 218 | 30 | A |
| 219 | 30 | A |
| 220 | 30 | A |
| 221 | 30 | A |
| 222 | 30 | A |
| 223 | 30 | A |
| 224 | 30 | A |
| 225 | 30 | A |
| 226 | 5 | A |
| 227 | 30 | A |
| 228 | 30 | A |
| 229 | 30 | A |
| 230 | 30 | A |
| 231 | 30 | A |
| 232 | 30 | A |
| 233 | 30 | A |
| 234 | 30 | A |

TABLE 3-2-continued

| EX | Dose (mg/kg) | Seizure suppression |
|---|---|---|
| 235 | 30 | A |
| 236 | 30 | A |
| 237 | 30 | A |
| 238 | 30 | A |
| 239 | 30 | A |
| 240 | 30 | A |

TABLE 3-3

| EX | Dose (mg/kg) | Seizure suppression |
|---|---|---|
| 241 | 30 | A |
| 242 | 30 | A |
| 243 | 5 | A |
| 244 | 30 | A |
| 245 | 30 | A |
| 246 | 30 | A |
| 247 | 30 | A |
| 248 | 5 | A |
| 249 | 30 | A |
| 250 | 30 | A |
| 251 | 30 | A |
| 252 | 30 | A |
| 253 | 30 | A |
| 254 | 30 | A |
| 255 | 30 | A |
| 256 | 5 | B |
| 257 | 30 | A |
| 258 | 5 | A |
| 259 | 5 | A |
| 260 | 30 | A |
| 261 | 30 | A |
| 262 | 5 | A |
| 263 | 30 | A |
| 264 | 30 | A |
| 265 | 30 | A |
| 266 | 30 | A |
| 267 | 5 | A |
| 268 | 30 | A |
| 269 | 30 | A |
| 270 | 30 | A |
| 271 | 30 | A |
| 272 | 30 | A |
| 273 | 30 | A |
| 274 | 30 | A |
| 275 | 30 | A |
| 276 | 30 | A |
| 277 | 30 | A |
| 278 | 30 | A |
| 279 | 1 | A |
| 280 | 30 | A |
| 281 | 30 | A |
| 282 | 30 | A |
| 283 | 5 | A |
| 264 | 5 | A |
| 285 | 5 | A |
| 286 | 30 | A |
| 287 | 30 | A |
| 288 | 30 | A |
| 289 | 1 | A |
| 290 | 30 | A |
| 291 | 30 | A |
| 292 | 30 | A |
| 293 | 30 | A |
| 294 | 5 | A |
| 295 | 5 | A |
| 296 | 30 | A |
| 297 | 1 | A |
| 298 | 1 | A |
| 299 | 5 | A |
| 300 | 30 | A |
| 301 | 30 | A |
| 302 | 30 | A |

TABLE 3-3-continued

| EX | Dose (mg/kg) | Seizure suppression |
|---|---|---|
| 303 | 30 | A |
| 304 | 30 | A |
| 305 | 30 | A |
| 806 | 30 | A |
| 307 | 30 | B |
| 308 | 30 | C |
| 309 | 30 | A |
| 310 | 30 | C |
| 311 | 30 | B |
| 312 | 30 | C |
| 313 | 30 | C |
| 314 | 30 | A |
| 315 | 30 | B |
| 316 | 30 | A |
| 317 | 30 | C |
| 318 | 30 | C |
| 319 | 30 | C |
| 320 | 30 | A |
| 321 | 30 | C |
| 322 | 30 | C |
| 323 | 39 | B |
| 324 | 30 | C |
| 325 | 30 | B |
| 326 | 30 | C |
| 327 | 30 | C |
| 328 | 30 | A |
| 329 | 30 | B |
| 330 | 30 | C |
| 331 | 30 | B |
| 332 | 30 | B |
| 333 | 30 | C |
| 334 | 30 | C |
| 335 | 30 | B |
| 336 | 30 | B |
| 337 | 30 | A |
| 338 | 30 | C |
| 339 | 30 | B |
| 340 | 30 | B |
| 341 | 30 | C |
| 342 | 30 | C |
| 343 | 30 | A |
| 344 | 30 | C |
| 345 | 30 | C |
| 346 | 30 | C |
| 347 | 30 | A |
| 348 | 1 | A |
| 349 | 3 | A |
| 350 | 10 | A |

[Test Example 2] Rotarod Test

This test is performed to evaluate the effect of the compound on the motor coordination.

In this test example, the example compounds shown in Table 4 below were used as test compounds.

Male ICR mice (Japan SLC, Inc., 5-6 weeks, 8 per group) were trained to remain on a fixed speed (15 rpm) rotating rod of rotarod apparatus (Muromachi Kikai Co., Ltd.) for 2 minutes. The test compound was suspended in 5% gum arabic/distilled water (w/v), and administered by forced oral administration at a dose of 30 mg/kg. After 1 hour of oral administration, the mice were again placed on the rod accelerated from 4 rpm to 40 rpm over 5 minutes and the latency to fall off the rod was recorded for 200 seconds. The falling latency of the compound administration group was calculated as a relative value relative to the average value of the falling latency in the solvent administration group.

The results are shown in Tables 4-1 and 4-2.

Here, a coordination disorder of 25% or less was expressed as "A", and a coordination disorder of more than 25% and 50% or less was expressed as "B".

TABLE 4-1

| EX | Dose (mg/kg) | Motor dysfunction |
|---|---|---|
| 1 | 5 | A |
| 2 | 10 | A |
| 3 | 10 | A |
| 4 | 5 | A |
| 5 | 5 | A |
| 6 | 5 | A |
| 7 | 5 | A |
| 8 | 10 | A |
| 10 | 30 | A |
| 11 | 5 | A |
| 22 | 5 | A |
| 24 | 5 | A |
| 26 | 5 | A |
| 27 | 30 | A |
| 30 | 5 | A |
| 31 | 5 | A |
| 33 | 30 | A |
| 34 | 30 | A |
| 36 | 5 | A |
| 38 | 10 | A |
| 40 | 3 | A |
| 42 | 5 | A |
| 55 | 30 | A |
| 58 | 30 | A |
| 59 | 3 | A |
| 64 | 3 | A |
| 66 | 30 | A |
| 74 | 5 | A |
| 90 | 5 | A |
| 91 | 5 | A |
| 92 | 5 | A |
| 93 | 30 | A |
| 95 | 10 | A |
| 97 | 3 | A |
| 98 | 3 | A |
| 99 | 10 | A |
| 101 | 3 | A |
| 102 | 10 | A |
| 103 | 30 | A |
| 107 | 30 | A |
| 113 | 10 | A |
| 114 | 5 | A |
| 118 | 5 | A |
| 119 | 5 | A |
| 120 | 5 | B |
| 121 | 5 | A |
| 122 | 5 | A |
| 123 | 5 | A |
| 127 | 5 | B |
| 129 | 5 | A |
| 134 | 5 | B |
| 137 | 30 | A |
| 141 | 5 | B |
| 143 | 30 | A |
| 148 | 30 | A |
| 151 | 5 | A |
| 155 | 5 | A |
| 161 | 5 | A |
| 162 | 5 | A |
| 163 | 5 | A |
| 170 | 5 | A |
| 171 | 5 | A |
| 172 | 5 | A |
| 173 | 5 | A |
| 177 | 5 | A |
| 181 | 5 | A |
| 184 | 5 | A |
| 188 | 30 | A |
| 190 | 5 | A |
| 194 | 5 | A |
| 198 | 5 | A |
| 204 | 5 | A |
| 211 | 30 | B |
| 214 | 30 | A |
| 216 | 5 | A |
| 220 | 30 | A |
| 222 | 30 | A |
| 223 | 30 | A |
| 224 | 30 | A |
| 226 | 5 | B |
| 229 | 30 | A |
| 235 | 30 | A |
| 236 | 30 | A |
| 237 | 30 | A |
| 239 | 30 | A |
| 243 | 5 | A |
| 245 | 30 | A |
| 248 | 5 | A |
| 256 | 5 | A |
| 258 | 5 | A |
| 259 | 5 | A |
| 262 | 5 | A |
| 267 | 5 | A |
| 275 | 30 | A |
| 279 | 1 | A |
| 283 | 5 | A |
| 285 | 5 | A |
| 289 | 1 | A |
| 293 | 30 | A |
| 294 | 5 | A |
| 295 | 5 | A |
| 296 | 30 | A |
| 297 | 1 | A |
| 298 | 1 | A |
| 299 | 5 | A |
| 300 | 30 | A |
| 302 | 30 | A |
| 303 | 30 | A |
| 304 | 30 | A |
| 305 | 30 | A |
| 306 | 30 | A |

TABLE 4-2

| EX | Dose (mg/kg) | Motor dysfunction |
|---|---|---|
| 307 | 30 | A |
| 309 | 30 | A |
| 311 | 30 | A |
| 314 | 30 | A |
| 316 | 30 | A |
| 320 | 30 | B |
| 323 | 30 | B |
| 325 | 30 | A |
| 328 | 30 | A |
| 329 | 30 | A |
| 331 | 30 | A |
| 332 | 30 | A |
| 336 | 30 | A |
| 337 | 30 | A |
| 340 | 30 | A |
| 343 | 30 | A |
| 347 | 30 | A |
| 348 | 1 | A |
| 349 | 3 | A |
| 350 | 10 | A |

[Test Example 3] Maximal Electroshock Seizure (MES) Model

This test is performed to evaluate the anticonvulsant activity of the compound. The mouse model used in this test is a phenotype model of generalized tonic-clonic seizure and secondary generalized partial seizure. This test was performed in accordance with the report of AJ Hill et al (Br J Pharmacol. 2012 December; 167 (8): 1629-42. Cannabidivarin is anticonvulsant in mouse and rat, Hill A J, et al.).

The test compound is suspended in 5% gum arabic/distilled water (w/v), and administers by forced oral administration to male ICR mice (Japan SLC, Inc., 5 to 6 weeks old, 8 per group) at a dose of 30 mg/kg. After one hour of the oral administration of the test compound, the mice are stimulated by an application of electrical current (30 mA, 100 Hz, 0.2 second) through auricular electrodes using an electroconvulsive device (UGO BASILE SRL). Then, the incidence of tonic hindlimb extension seizure is recorded.

In the above test, it is confirmed that, in the solvent administration group, tonic hindlimb extension seizure is induced in all examples, but in the test compound administration group, expression of seizure is suppressed.

[Test Example 4] Subcutaneous Pentylenetetrazole (scPTZ) Model

This test is performed to evaluate the anticonvulsant activity of the compound as in Test Example 3. Unlike the phenotype of Test Example 3, the animal model used in this test is a phenotype model of generalized absence seizure and myoclonic seizure.

The test compound is suspended in 5% gum arabic/distilled water (w/v), and administers by forced oral administration to male ICR mice (Japan SLC, Inc., 5 to 6 weeks old, 10 per group) at a dose of 30 mg/kg. After 1 hour, 85 mg/kg of pentylenetetrazole dissolved in saline is administered subcutaneously, and the occurrence of clonic convulsions is evaluated for 30 minutes.

In the above test, it is confirmed that, in the solvent administration group, clonic convulsion is induced in all examples, but in the test compound administration group, expression of convulsion is suppressed.

Thus, since the compound of the present invention exhibits anticonvulsive action in all cases in multiple animal models used to evaluate antiepileptic drugs, it is useful as an antiepileptic drug with a wide treatment spectrum (compound for preventing and/or treating seizure in disease involving epileptic seizure or convulsive seizure (including multiple drug resistant seizure, refractory seizure, acute symptomatic seizure, febrile seizure and status epilepticus)). Moreover, the compound of the present invention is useful as a diagnostic compound for disease involving epileptic seizure or convulsive seizure (including multiple drug resistant seizure, refractory seizure, acute symptomatic seizure, febrile seizure and status epilepticus).

EXAMPLES

Example 1

Synthesis of 3-Methoxy-6-(2-Phenoxypyrimidin-5-Yl)Pyridazine

A mixture containing 2-phenoxy-5-(4,4,5,5-tetramethyl-1,3,2-dioxaborolan-2-yl)pyrimidine (5.00 g), 3-chloro-6-methoxypyridazine (3.64 g), PdCl$_2$ (dppf) DCM (0.137 g), K$_3$PO$_4$ (7.12 g), 1,4-dioxane (50 mL), and water (25 mL) was heated to reflux under a nitrogen atmosphere for 2 hours. The reaction solution was poured into water, and the product was extracted with AcOEt. The organic layer was washed with water and brine and dried with anhydrous sodium sulfate and then concentrated. The residue was purified through silica gel column chromatography (DCM/AcOEt) to obtain the object compound (4.42 g).

Example 4

Synthesis of 3-(2-(3-Fluorophenoxy)Pyrimidin-5-Yl)-6-Methoxypyridazine

A mixture containing 5-bromo-2-(3-fluorophenoxy)pyrimidine (2.234 g), (BPin)$_2$ (2.63 g), PdCl$_2$ (dppf) DCM (0.282 g), AcOK (1.358 g), and 1,4-dioxane (20 mL) was heated to reflux under a nitrogen atmosphere for 2 hours. 3-Chloro-6-methoxypyridazine (1.00 g), PdCl$_2$ (dppf) DCM (0.282 g), K$_3$PO$_4$ (2.94 g), and water (5 mL) were added to the reaction solution and the mixture was heated to reflux under a nitrogen atmosphere overnight. Water and AcOEt were added to the

The invention claimed is:

1. A compound represented by Formula I:

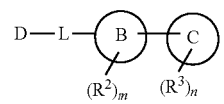

[Formula I]

wherein
D is

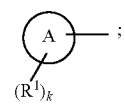

ring A is benzene;
ring B is pyrimidine;
ring C is the following unsaturated rings, oxides thereof, dioxides thereof, provided that pyrimidine-2,4-dione and dihydropyrimidine-2,4-dione are excluded, or those in which a part or all of unsaturated bonds in the unsaturated rings are reduced with hydrogen:
pyridazine,
pyrimidine,
indole,
pyrrolopyridine,
indazole,
pyrazolopyridine,
imidazopyridine,
imidazopyrazine,
imidazopyridazine,
triazolopyridine,
pyrazolopyrimidine,
imidazopyrimidine,
triazolopyrimidine,
isoquinoline,
naphthyridine,
quinazoline,
quinoxaline,
benzodioxole,
oxazine,
oxazepine,
benzothiazole, and
triazolopyridazine;
wherein ring C is bonded to a 5-position of ring B,
R$^1$ is halogen, C$_{1-6}$ alkyl optionally substituted with halogen, —O—C$_{1-6}$ alkyl optionally substituted with halogen or —CN;
R$^2$ is —O—C$_{1-6}$ alkyl;

$R^3$ is halogen, $C_{1-6}$ alkyl optionally substituted with halogen or —O—$C_{1-6}$ alkyl, —O— $C_{1-6}$ alkyl optionally substituted with halogen, —$C_{1-6}$ alkyl-OH, —OH, —CN, —CONH$_2$ or —NH$_2$;

L is —O—, which is bonded at a 2-position of ring B; and k is 0, 1 or 2, and when k is 2, each $R^1$ independently represents the same or different substituent;

m is 0 or 1;

n is 0, 1 or 2, and when n is 2, each $R^3$ independently represents the same or different substituent;

or a salt thereof.

2. The compound according to claim 1, wherein, in Formula I, ring C is the following unsaturated rings, oxides thereof, or those in which a part or all of unsaturated bonds in the unsaturated rings are reduced with hydrogen:
pyridazine,
pyrrolopyridine,
indazole,
pyrazolopyridine,
imidazopyridine,
imidazopyrazine,
imidazopyridazine,
pyrazolopyrimidine,
triazolopyrimidine,
isoquinoline,
naphthyridine,
quinoxaline,
triazolopyridine, and
triazolopyridazine;

$R^1$ is halogen or $C_{1-6}$ alkyl optionally substituted with halogen;

$R^3$ is $C_1$-6 alkyl optionally substituted with halogen, —O—$C_{1-6}$ alkyl optionally substituted with halogen, —OH, —CONH$_2$ or —NH$_2$;

k and n are 0 or 1; and m is 0;

or a salt thereof.

3. The compound according to claim 2, wherein, in Formula I, ring C is the following unsaturated rings, oxides thereof, or those in which a part or all of unsaturated bonds in the unsaturated rings are reduced with hydrogen:
pyridazine,
pyrazolopyridine, and
imidazopyridine;

$R^3$ is —OH or —NH$_2$;

L is —O—;

k and m are 0; and n is 0 or 1;

or a salt thereof.

4. A compound selected from the group consisting of the following compounds:

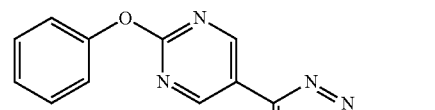

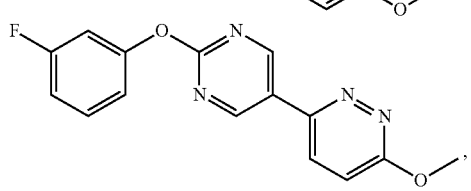

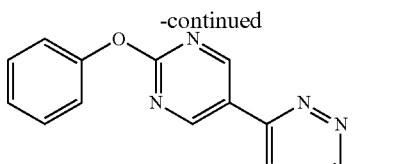

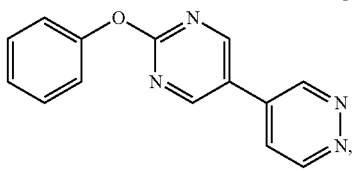

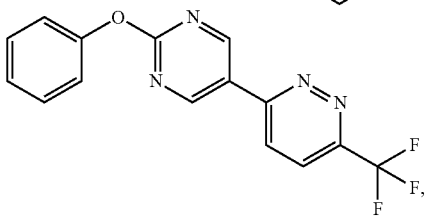

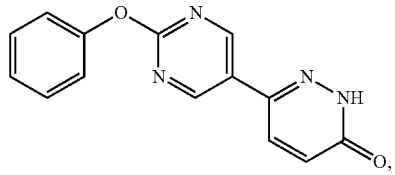

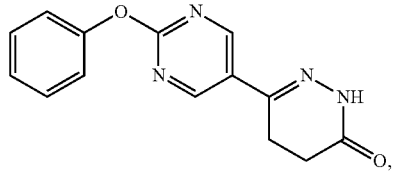

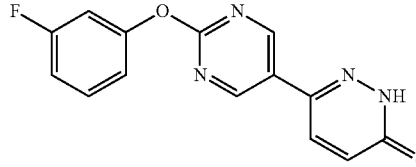

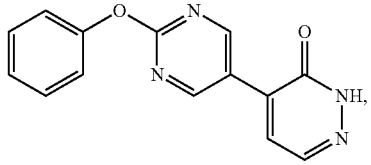

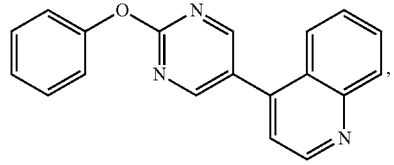

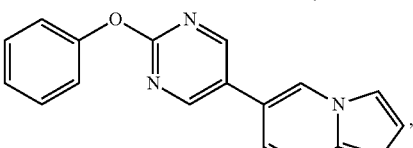

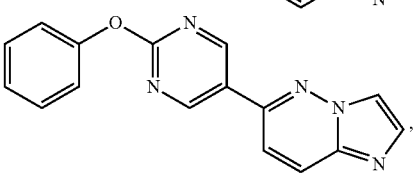

-continued
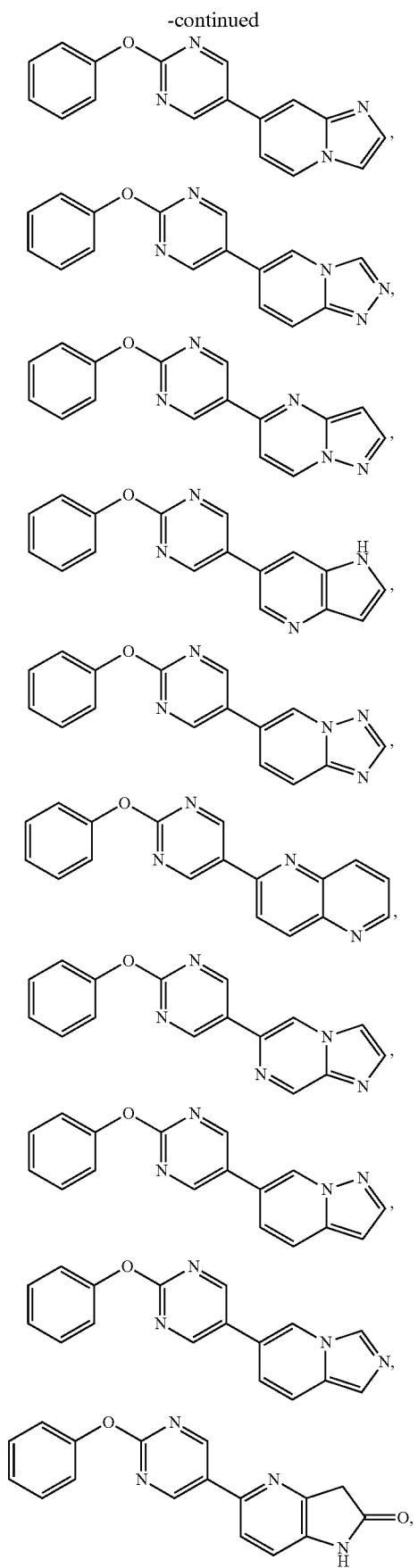
-continued
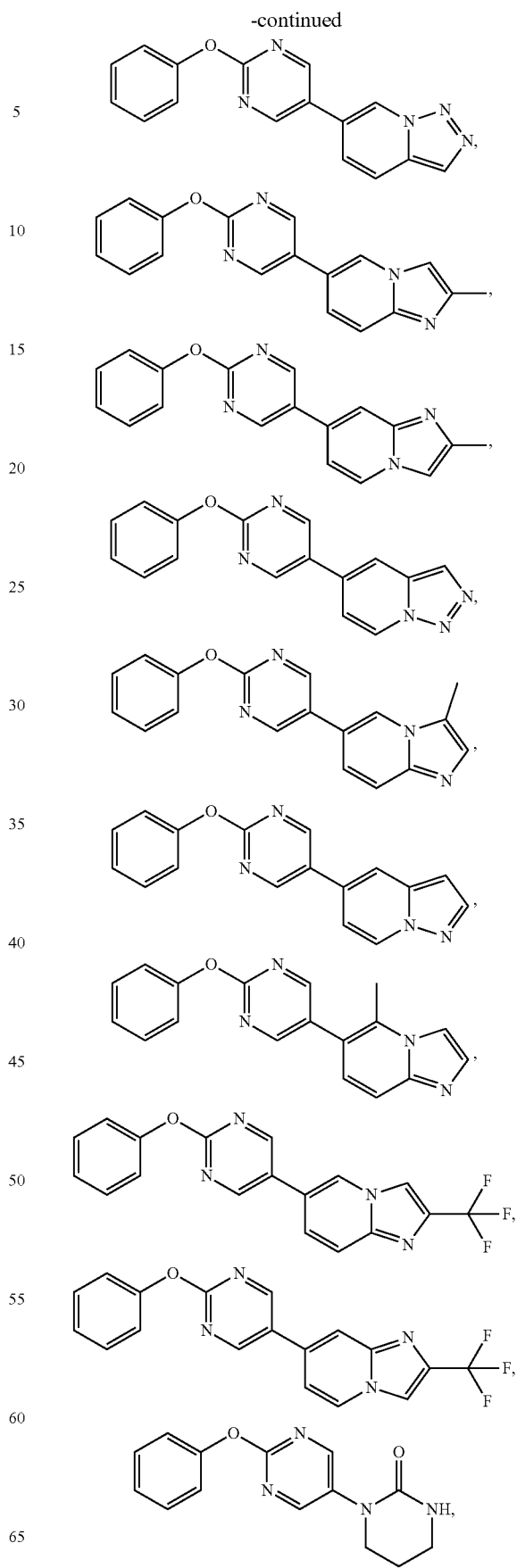

197
-continued
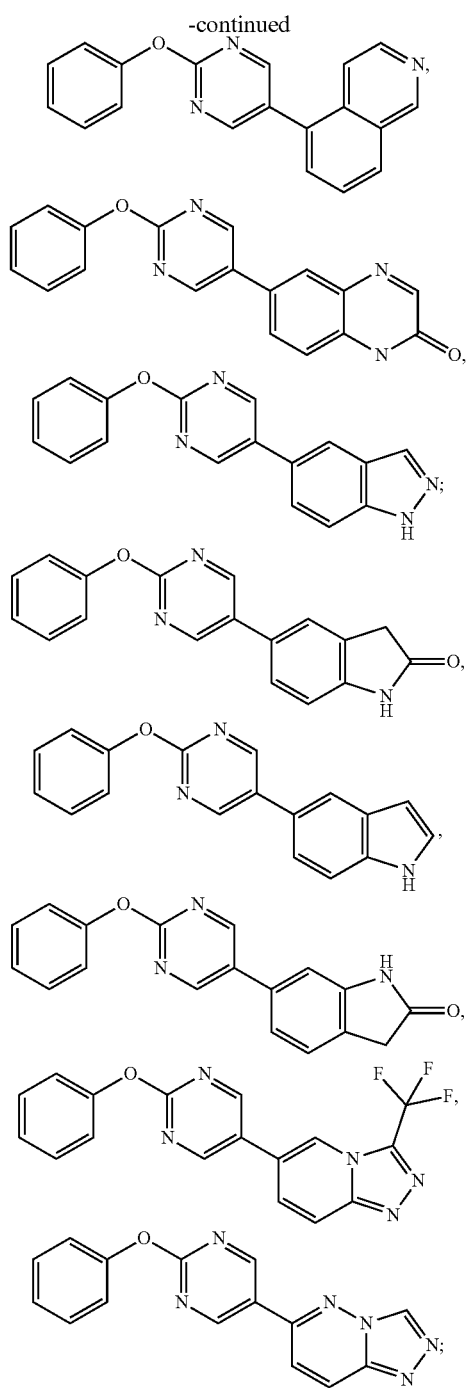
or a salt thereof.
5. The compound according to claim 4 selected from the group consisting of the following compounds:
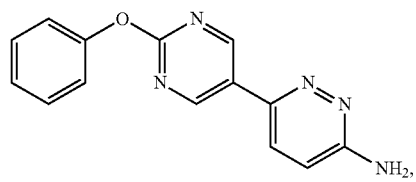
198
-continued
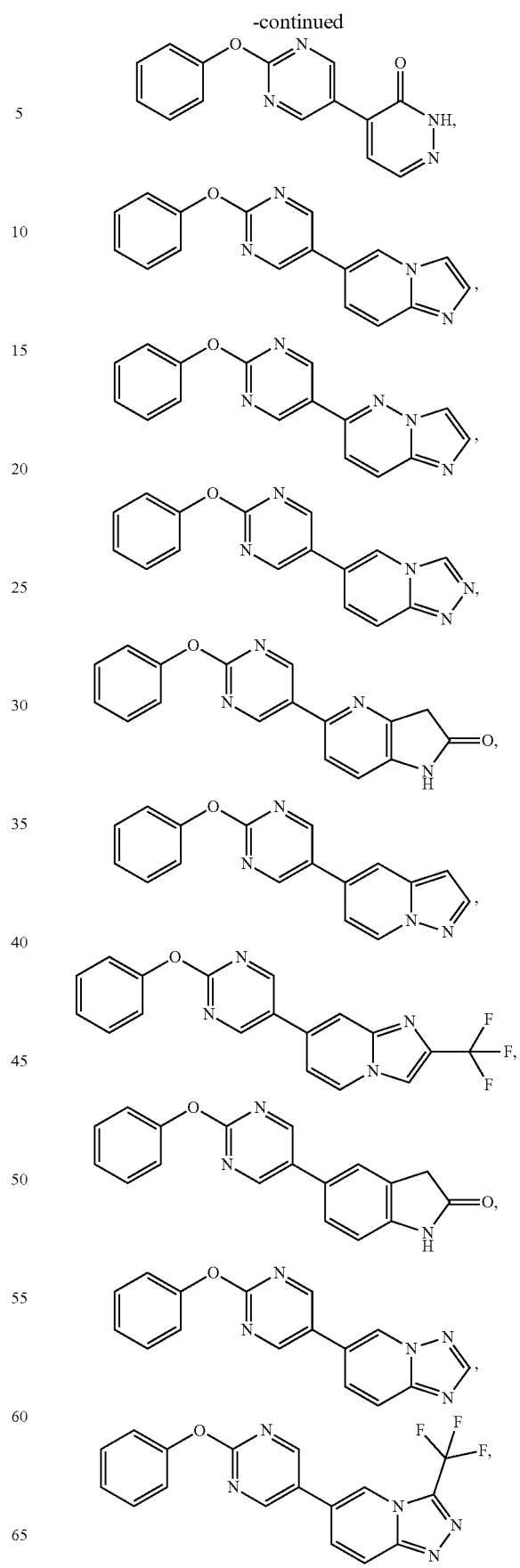

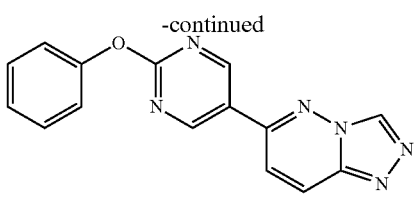

or a salt thereof.

6. A compound represented by the following formula:

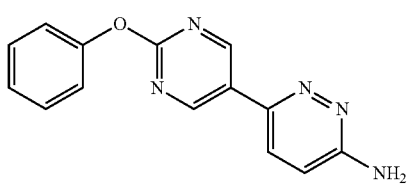 [SMILES: Nc1ccc(-c2cnc(Oc3ccccc3)nc2)nn1]

or a salt thereof.

7. A compound represented by the following formula:

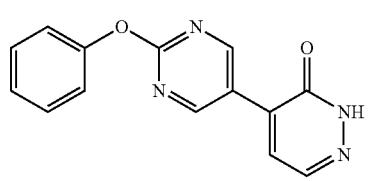 [SMILES: O=c1[nH]nccc1-c1cnc(Oc2ccccc2)nc1]

or a salt thereof.

8. A compound represented by the following formula:

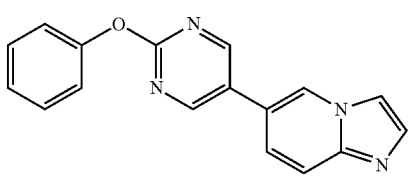 [SMILES: c1ccc(Oc2ncc(-c3ccc4nccn4c3)cn2)cc1]

or a salt thereof.

9. A compound represented by the following formula:

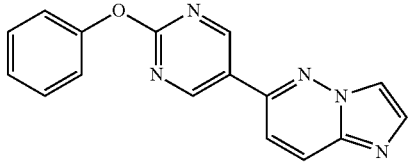 [SMILES: c1ccc(Oc2ncc(-c3ccc4nccn4n3)cn2)cc1]

or a salt thereof.

10. A compound represented by the following formula:

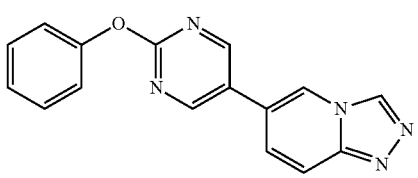

or a salt thereof.

11. A compound represented by the following formula:

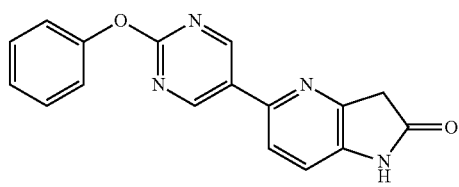

or a salt thereof.

12. A compound represented by the following formula:

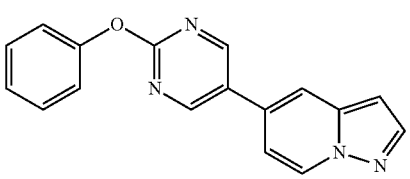 [SMILES: c1ccc(Oc2ncc(-c3ccn4nccc4c3)cn2)cc1]

or a salt thereof.

13. A compound represented by the following formula:

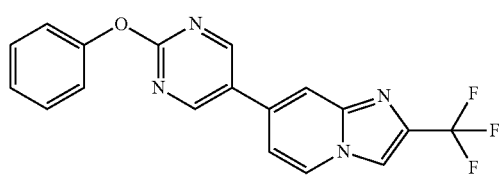 [SMILES: FC(F)(F)c1cn2ccc(-c3cnc(Oc4ccccc4)nc3)cc2n1]

or a salt thereof.

14. A compound represented by the following formula:

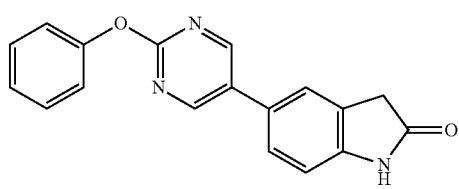

or a salt thereof.

15. A compound represented by the following formula:

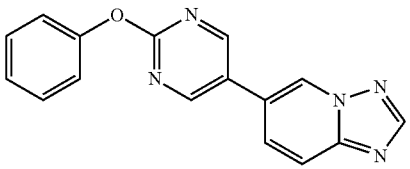 [SMILES: c1ccc(Oc2ncc(-c3ccc4ncnn4c3)cn2)cc1]

or a salt thereof.

16. A compound represented by the following formula:
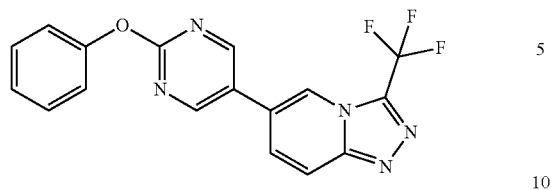
or a salt thereof.
17. A compound represented by the following formula:
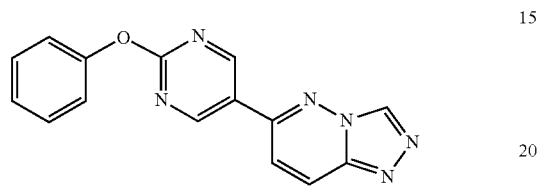
or a salt thereof.
* * * * *